(12) United States Patent
Koizumi et al.

(10) Patent No.: US 10,908,161 B2
(45) Date of Patent: Feb. 2, 2021

(54) CORNEAL ENDOTHELIAL CELL MARKER

(71) Applicants: KYOTO PREFECTURAL PUBLIC UNIVERSITY CORPORATION, Kyoto (JP); ACTUALEYES INC., Kyotanabe (JP); CORNEAGEN, INC., Seattle, WA (US)

(72) Inventors: Noriko Koizumi, Kyotanabe (JP); Naoki Okumura, Kyotanabe (JP); Hiroatsu Hirano, Kyotanabe (JP); Shigeru Kinoshita, Kyoto (JP); Morio Ueno, Kyoto (JP)

(73) Assignees: KYOTO PREFECTURAL PUBLIC UNIVERSITY CORPORATION, Kyoto (JP); ACTUALEYES INC., Kyotanabe (JP); CORNEAGEN. INC., Seattle, WA (US)

( * ) Notice: Subject to any disclaimer, the term of this patent is extended or adjusted under 35 U.S.C. 154(b) by 621 days.

(21) Appl. No.: 14/908,036

(22) PCT Filed: Jul. 28, 2014

(86) PCT No.: PCT/JP2014/070412
§ 371 (c)(1),
(2) Date: Jan. 27, 2016

(87) PCT Pub. No.: WO2015/016371
PCT Pub. Date: Feb. 5, 2015

(65) Prior Publication Data
US 2016/0266114 A1 Sep. 15, 2016

(30) Foreign Application Priority Data

Jul. 30, 2013 (JP) .................................. 2013-157597

(51) Int. Cl.
*G01N 33/569* (2006.01)
*A61K 35/30* (2015.01)
*C12N 5/079* (2010.01)

(52) U.S. Cl.
CPC ....... *G01N 33/56966* (2013.01); *A61K 35/30* (2013.01); *C12N 5/0621* (2013.01); *G01N 2333/705* (2013.01); *G01N 2333/70596* (2013.01)

(58) Field of Classification Search
CPC ....... G01N 33/56966; G01N 2333/705; G01N 2333/70596; C12N 5/0621; A61K 35/30; A61P 27/02
See application file for complete search history.

(56) References Cited

U.S. PATENT DOCUMENTS

| 4,678,783 A | 7/1987 | Hidaka et al. |
| 5,514,554 A | 5/1996 | Bacus |
| 5,876,949 A | 3/1999 | Dreyfuss et al. |
| 2006/0216821 A1* | 9/2006 | Totey ................ C12N 5/0607 435/368 |
| 2014/0370007 A1* | 12/2014 | McCabe ............. A61K 35/30 424/133.1 |

FOREIGN PATENT DOCUMENTS

| JP | 10113187 A | 5/1998 |
| JP | 2013-157597 A | 8/2013 |
| WO | 95/28387 A1 | 10/1995 |
| WO | 99/20620 A1 | 4/1999 |
| WO | 99/61403 A1 | 12/1999 |
| WO | 02/076976 A2 | 10/2002 |
| WO | 02/076977 A2 | 10/2002 |
| WO | 2002/083175 A1 | 10/2002 |
| WO | 02/100833 A1 | 12/2002 |
| WO | 03/059913 A1 | 7/2003 |
| WO | 03/062227 A1 | 7/2003 |
| WO | 2004/009555 A1 | 1/2004 |
| WO | 2004/022541 A1 | 3/2004 |
| WO | 2004/108724 A1 | 12/2004 |

(Continued)

OTHER PUBLICATIONS

Pei et al. "Thy-1 distinguishes human corneal fibroblasts and myofibroblasts from keratocytes." Exp Eye Res. Nov. 2004;79(5):705-12. (Year: 2004).*
Peh et al. "Optimization of Human Corneal Endothelial Cells for Culture: The Removal of Corneal Stromal Fibroblast Contamination Using Magnetic Cell Separation." Int J Biomater. 2012; 2012 (Year: 2012).*
Chen et al. "Identification of novel molecular markers through transcriptomic analysis in human fetal and adult corneal endothelial cells." Hunn Mol Genet. Apr. 1, 2013;22(7):1271-9. (Year: 2013).*
Choong et al. "Mesenchymal stromal cell-like characteristics of corneal keratocytes." Cytotherapy. 2007;9(3):252-8. (Year: 2007).*

(Continued)

*Primary Examiner* — Titilayo Moloye
(74) *Attorney, Agent, or Firm* — Foley & Lardner LLP

(57) ABSTRACT

The purpose of the present invention is to provide a method of purification and preparation of cultured corneal endothelial cells, and in particular, to provide cell surface markers for use in corneal endothelial cells not including transformed cells. Provided are cell markers for distinguishing normal cells and transformed cells, in particular normal and transformed corneal endothelium cells. These cell markers relate to specific cell surface markers, for example, to a normal corneal endothelial surface marker such as CD166, and a transformed cell surface marker such as CD73. By using the transformed cell surface marker such as CD73 to remove transformed cells by sorting, it becomes possible to improve purity of a normal cultured corneal endothelium. By using normal corneal endothelial surface marker such as CD166, or by combined use with the transformed cell surface marker, it becomes possible to provide a means for verifying the purity of a prepared corneal endothelium.

10 Claims, 11 Drawing Sheets

Specification includes a Sequence Listing.

(56) References Cited

FOREIGN PATENT DOCUMENTS

| | | |
|---|---|---|
| WO | 2005/034866 A2 | 4/2005 |
| WO | 2005/035501 A1 | 4/2005 |
| WO | 2005/035503 A1 | 4/2005 |
| WO | 2005/035506 A1 | 4/2005 |
| WO | 2005/037197 A2 | 4/2005 |
| WO | 2005/037198 A2 | 4/2005 |
| WO | 2005/080394 A1 | 9/2005 |
| WO | 2005/103050 A2 | 11/2005 |
| WO | 2006/057270 A1 | 6/2006 |
| WO | 2007/026664 A1 | 3/2007 |
| WO | 2013012087 | 1/2013 |
| WO | 2013051722 A1 | 4/2013 |
| WO | 2013086236 A2 | 6/2013 |
| WO | 2013100208 A1 | 7/2013 |
| WO | 2015016371 A1 | 2/2015 |

OTHER PUBLICATIONS

Okumura et al. "Inhibition of TGF-β signaling enables human corneal endothelial cell expansion in vitro for use in regenerative nnedicine." PLoS One. 2013;8(2):e58000. Epub Feb. 25, 2013. (Year: 2013).*

Supplementary Partial European Search Report Issued in corresponding European Application No. EP14831264 dated Feb. 20, 2017.

Yuen Kuen Cheong et al: "Identification of Cell Surface Markers Glypican-4 and CD200 That Differentiate Human Corneal Endothelium From Stromal Fibroblasts", Investigative Opthalmology & Visual Science, vol. 54, No. 7, Jul. 8, 2013 (Jul. 8, 2013), p. 4538.

Hayashi Ryuhei et al: "Enrichment of corneal epithelial stem/progenitor cells using cell surface markers, integrin [alpha] 6and", Biochemical and Biophysical Research Communications, vol. 367, No. 2, 2008, pp. 256-263.

Kim H-S et al: "Phenotypic characterization of human corneal epithelial cells expanded ex vivo from limbal explant and single cell cultures", Experimental Eye Research, Academic Press LTD, London, vol. 79, No. I, Jul. 1, 2004 (Jul. 1, 2004) pp. 41-49.

Y. Chen et al: "Identification of novel molecular markers through transcriptomic analysis in human fetal and adult corneal endothelial cells" Human Molecular Genetics, vol. 22, No. 7, Apr. 1, 2013 (Apr. 1, 2013), pp. 1271-1279.

Bian F et al: "Molecular signatures and biological pathway profiles of human corneal epithelial progenitor cells", International Journal of Biochemistry and Cell Biology, Pergamon, GB, vol. 42, No. 7, Jul. 1, 2010 (Jul. 1, 2010), pp. 1142-1153.

Dua H S et al: "Stem cell differentiation and the effects of deficiency" Eye, Royal College of Ophtalmologists, London, GB, vol. 17, No. 81 Nov. 2003 (Nov. 1, 2003), pp. 877-885.

Claudia Auw-Haedrich et al: "Immunohistochemical expression of epithelial cell markers in corneas with congenital aniridia and ocular cicatrizing pemphigoid", Acta Ophthalmologica: The Ophthalmological Journal of the Nordic Countries, vol. 89, No. 1, Feb. 24, 2011 (Feb. 24, 2011), pp. 47-53.

Schlotzer-Schrehardt et al: "Identification and characterization of Limbal stem cells", Experimental Eye Research, Academic Press Ltd, London, vol. 81, No. 3, Sep. 1, 2005 (Sep. 1, 2005), pp. 247-264.

S.-N. Zhu et al: "Expression of adhesion molecule CD44 on human corneas", British Journal of Ophthalmology, vol. 81, No. 1, Jan. 1, 1997 (Jan. 1, 1997), pp. 80-84.

Reka Albert et al: "Cultivation and Characterization of Cornea Limbal Epithelial Stem Cells on Lens Capsule in Animal Material-Free Medium", Plos One, vol. 7, No. 10, Oct. 9, 2012 (Oct. 9, 2012), p. e47187.

International Search Report and Written Opinion issued in corresponding International Application No. PCT/JP2014/070412 dated Nov. 4, 2014.

The Proceedings of the General Meeting of the Japan Cornea Society/Keratoplasty Society of Japan Program: vol. 35th-27th, p. 75 (2011).

Yamamizu et al., Identification of corneal endothelial cell-specific cell surface marker, Regenerative Medicine, 2010, vol. 9, Suppl. p. 283.

Matsuzaki et al., Examination of corneal endothelial cell surface marker, Regenerative Medicine, 2011, vol. 10, Suppl., p. 201.

Extended European Search Report issued in corresponding European application No. 14831264.8 dated May 31, 2017.

Nakagawa et al., "Search for a marker gene of corneal endothelia by comprehensive expression analysis using a next-generation sequencer," Japanese Journal of Ophthalmology, vol. 117, Extra edition, p. 378 (Apr. 2013).

Kagaya et al., "Comparison of measurement values of corneal thickness by three types of methods," Japanese Journal of Ophthalmology, vol. 105, Extra edition, p. 195 (Mar. 2001).

EGFR P00533, Uniprot [online], (Jan. 2013), [retrieved on 04.26. 219], URL, https://www.uniprot.org/uniprot/P00533.txt?version=190.

Katagiri et al., "Functional Significance of Stage-specific Embryonic Antigens in the Development of Preimplantation Embryos," Trends in Glycoscience and Glycotechnology, 2009, vol. 20, pp. 131-139.

Mica/B Q4W316, Uniprot [online], Mar. 2013 [retrieved on Apr. 26, 2019], URL, https:www.uniprot.org/uniport/Q4W316.txt?version=34.

Office Action dated May 14, 2019 in Japanese Application No. 2018-114955.

Tada, "T Cell Receptors and MHC Molecules," Immunology illustrated, (Feb. 2000), Original 5th Edition, pp. 83-92.

Partial Translation of Office Action dated May 14, 2019 in Japanese Application No. 2018-114955 citing TADA, "T Cell Receptors and MHC Molecules," Immunology illustrated, (Feb. 2000), Original 5th Edition, pp. 83-92.

"Human and Mouse CD Marker Handbook," BD Biosciences (Nov. 2011), pp. 1-46. [retrieved on Jun. 23, 2020], https://web.archive.org/web/20111125071113/https://www.bdbiosciences.com/documents/cd_marker_handbook.pdf.

* cited by examiner

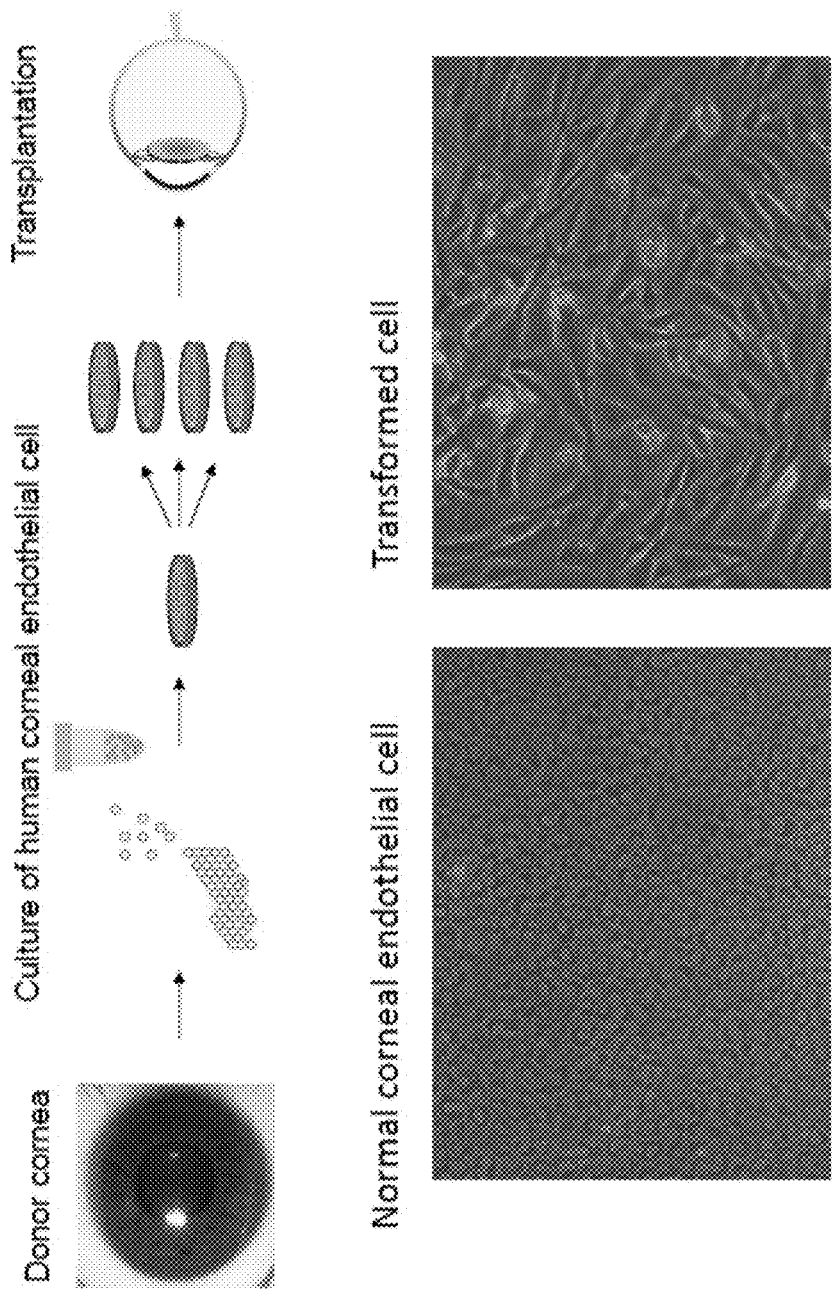

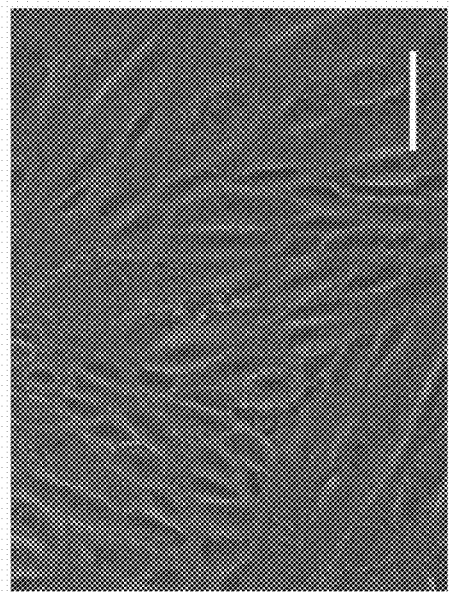
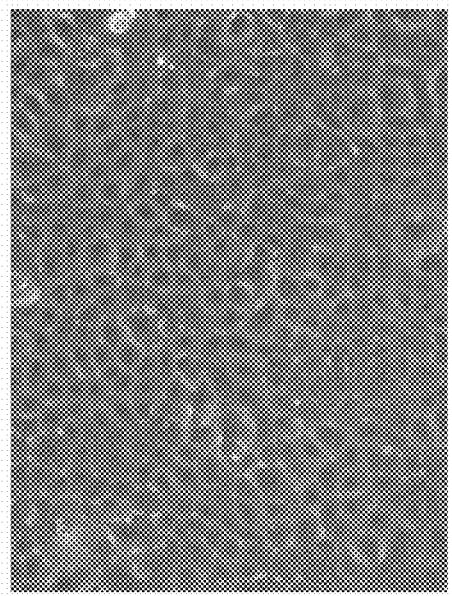
Fig.2. Images of cultured monkey corneal endothelial cells from a phase difference microscope

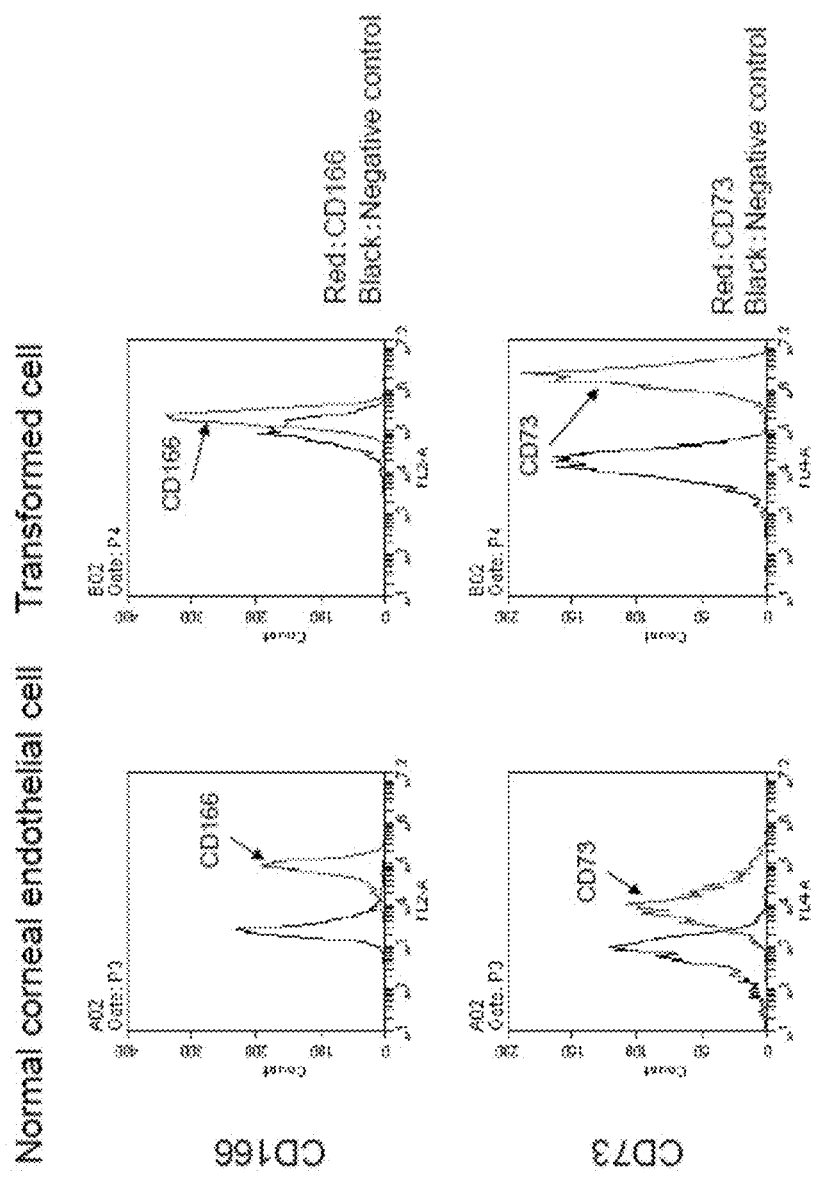

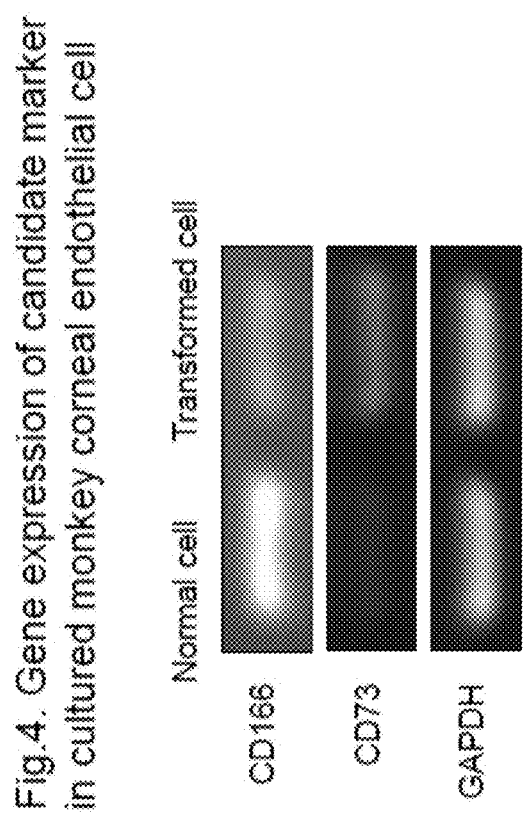

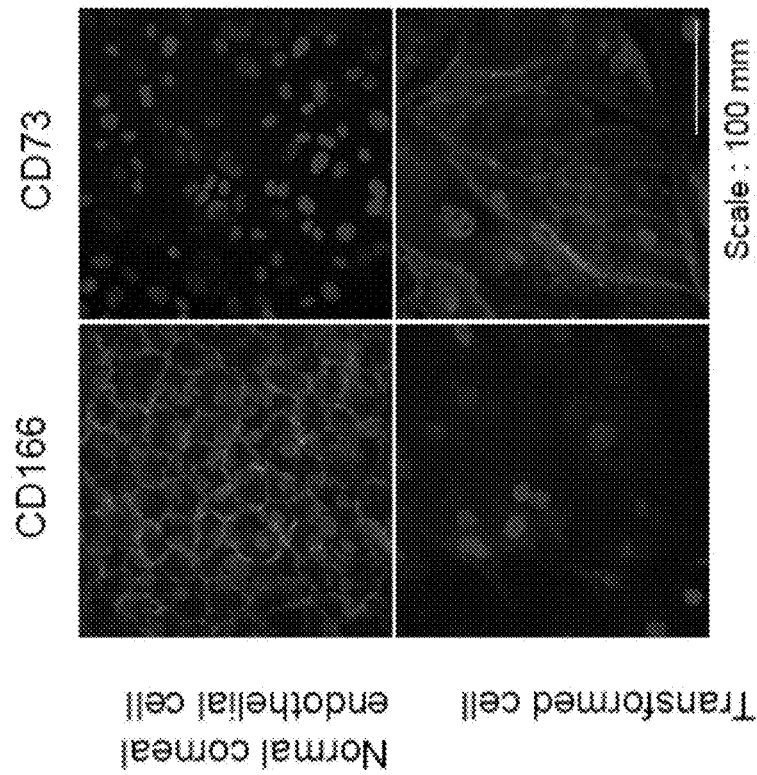
Fig.5. Images of candidate marker immunostaining in cultured monkey corneal endothelial cell

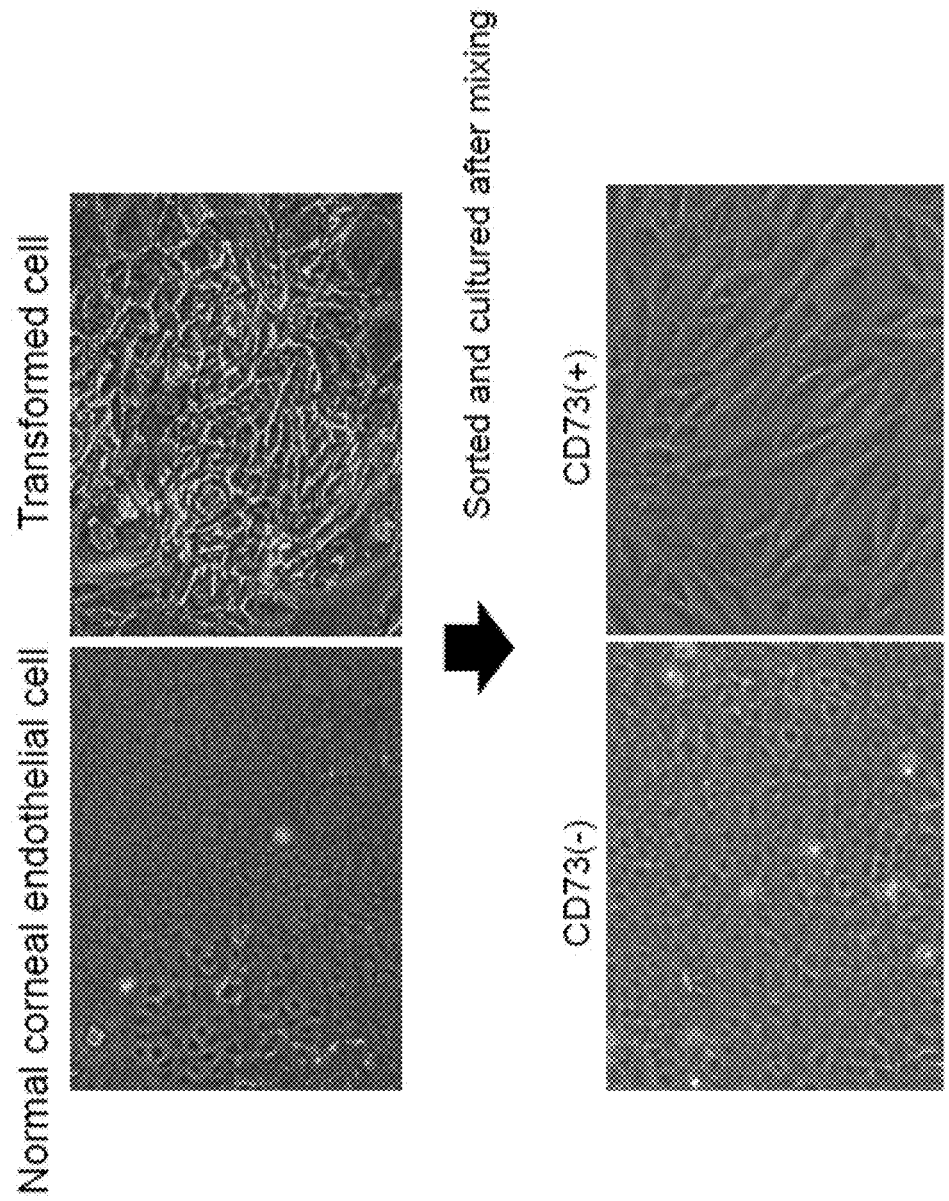

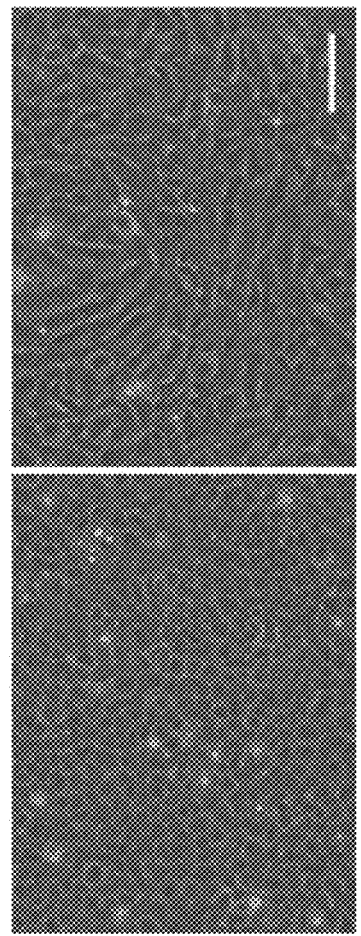
Fig.7. Images of immortalized human corneal endothelial cells from a phase difference microscope

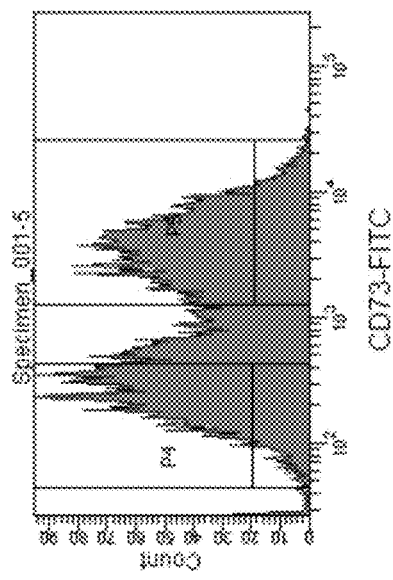
Fig.8. Flow cytometry analysis of mixed culture cells of normal form and transformed immortalized human corneal endothelial cells

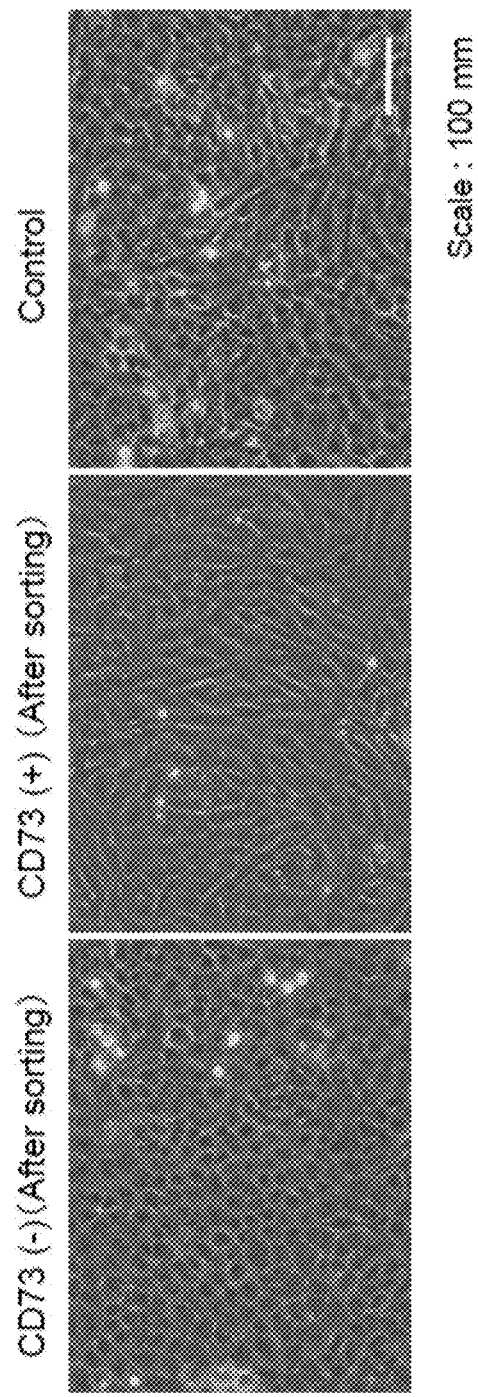

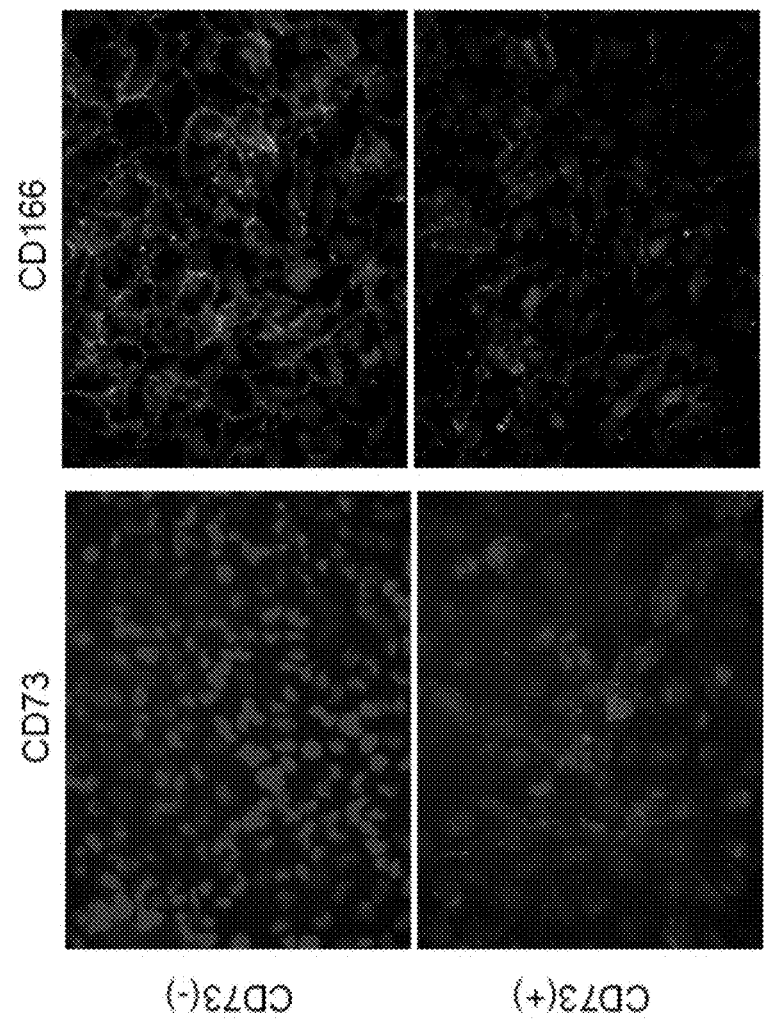
Fig. 10. Analysis of expression of candidate markers after sorting by CD73

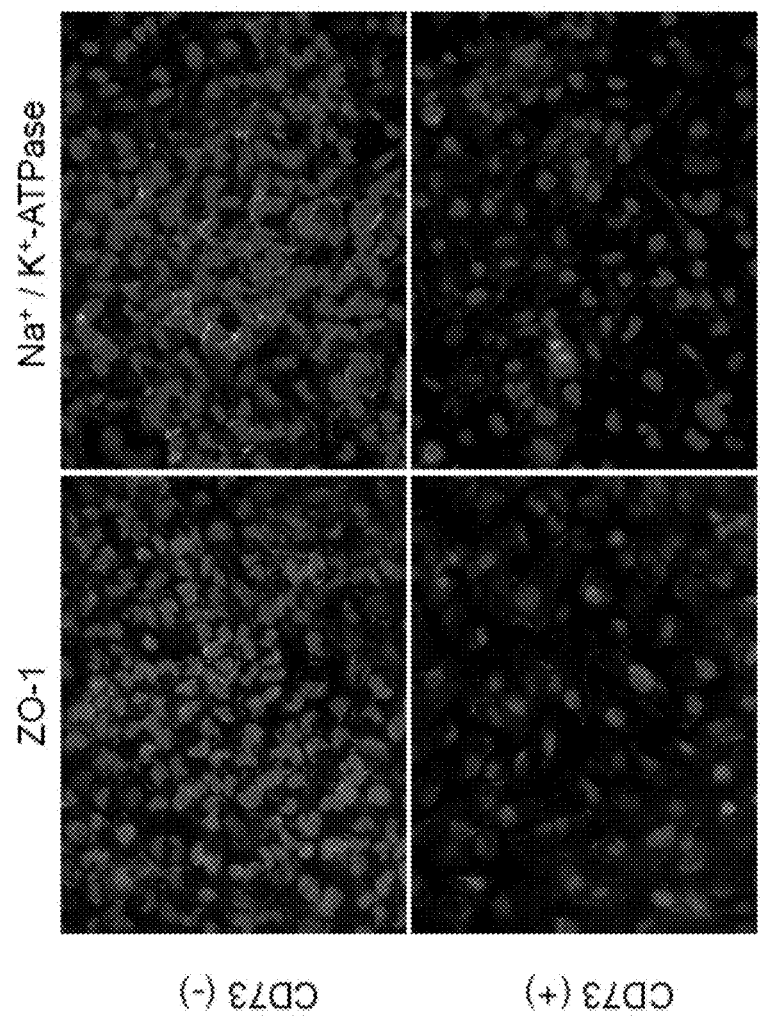
Fig.11. Analysis of expression of function associated after sorting by CD73

CORNEAL ENDOTHELIAL CELL MARKER

CROSS REFERENCE TO RELATED APPLICATIONS

The present application is the U.S. National Phase of International Patent Application Serial No. PCT/JP2014/070412, filed Jul. 28, 2014, which claims priority to Japanese Patent Application Serial No. 2013-157597, filed Jul. 30, 2013. The contents of the foregoing applications are hereby incorporated by reference in their entireties.

TECHNICAL FIELD

The present invention relates to a cell, particularly a differentiated marker in the ophthalmological region, and particularly a corneal endothelial cell marker.

BACKGROUND ART

Visual information is recognized when light transmitted into the cornea, which is a transparent tissue at the frontmost part of an eye ball, reaches the retina and excites nerve cells of the retina and a generated electric signal is transmitted through the optic nerve to the visual cortex of the cerebrum. To attain good vision, it is necessary that the cornea is transparent. The transparency of the cornea is maintained by maintaining constant water content with pumping and barrier functions of corneal endothelial cells.

The cornea is a transparent tissue positioned in the front side of an eyeball and having a three layer structure of mainly a corneal epithelial cell layer, a corneal stroma layer, and a corneal endothelial layer. The corneal endothelial layer is a single-layer cell layer present in the deeper part of the cornea. The corneal endothelial cell layer has barrier and pumping functions and plays a role in maintaining transparency of the cornea by maintaining a constant amount of moisture in the cornea. Further, it is known that corneal endothelial cells do not grow in a living body even if they are damaged. In addition, it is known that a decrease in the number of corneal endothelial cells from damage due to trauma, disease or the like to the cells leads to severe visual impairment.

Human corneal endothelial cells are present at a density of about 3000 per 1 $mm^2$ at birth. However, once damaged, corneal endothelial cells do not have the ability to regenerate. Corneal endothelial dystrophy or bullous keratopathy induced by dysfunction of the corneal endothelium due to various causes results in edema or turbidity of the cornea, leading to significant deterioration in vision. Currently, penetrating keratoplasty is performed to transplant the entire three layer structure consisting of epithelium, stroma, and endothelium of the cornea for bullous keratopathy. However, cornea donation is insufficient in Japan. While there are about 2600 patients waiting for cornea transplantation, the number of corneal transplantations cases performed domestically with a donor cornea is about 1700 annually.

In recent years, the concept of "part transplantation" for transplanting only damaged tissue has drawn attention in order to alleviate the risk of post-operative complication or rejection and to attain better visual function. Among corneal transplantations, deep lamellar keratoplasty, which is a transplantation of stromal tissue, Descemet's stripping automated endothelial keratoplasty, which is a transplantation of corneal endothelial tissue, and the like have been performed. Further, cultured mucosal epithelium transplantation for transplanting corneal epithelium or oral mucosa cultured in vitro to replace the corneal epithelium is already in clinical application. Similarly, a method of transplanting corneal endothelium cultured in vitro also has been investigated.

A method of regenerating and utilizing corneal endothelial cells is being investigated, but there is hardly any marker for identifying regenerated corneal endothelial cells.

Although Patent Literature 1 has descriptions on corneal endothelial cell markers, they are different from the markers of the present invention. Although Patent Literature 2 discloses corneal endothelial cell markers, none are surface antigens. Although Patent Literature 3 discloses the concept of identifying corneal endothelial cells, the marker used is a neural crest marker.

Although Non Patent Literature 1 has descriptions on identification of corneal endothelial cell-specific cell surface markers, there is no specific disclosure. Although Non Patent Literature 2 discloses a corneal endothelial cell marker, the marker is not a surface antigen. Although Non Patent Literature 3 has descriptions on epithelial cell or endothelial cell markers, there is no specific description related to corneal endothelial cells. Non Patent Literature 4 is a document describing a marker for corneal stroma cells, which does not have a description related to corneal endothelial cells. Although Non Patent Literature 5 discloses corneal endothelial cell markers, none are surface antigens. Although Non Patent Literature 6 discloses corneal endothelial cell markers, none are surface antigens. Although Non Patent Literature 7 discloses corneal endothelial cell markers, none are surface antigens. Although Non Patent Literature 8 discloses corneal endothelial cell markers, there is no specific disclosure. Although Non Patent Literature 9 discloses corneal endothelial cell markers, none are surface antigens.

In this manner, the state of surface molecules for determining whether transformation of a corneal endothelium is normal has not been elucidated.

CITATION LIST

Patent Literature

[PTL 1] International Publication No. WO 2013/086236

[PTL 2] International Publication No. WO 2013/051722

[PTL 3] International Publication No. WO 2013/012087

Non Patent Literature

[NPL 1] Saisei Iryo [*Regenerative Medicine*]: Vol. 9, Extra issue, Page. 283 (Feb. 5, 2010)

[NPL 2] The Proceedings of the General Meeting of the Japan Cornea Society/Keratoplasty Society of Japan Program: Vol. 35th-27th, Page. 75 (2011)

[NPL 3] Am J Pathol. 2011 February; 178(2) 572-9.

[NPL 4] Cytotherapy. 2007; 9(3): 252-8

[NPL 5] Japanese Journal of Ophthalmology, Vol. 117, Extra edition, Page. 378 (Mar. 4, 2013)

[NPL 6] Kunzevitzky, N J, et al. ARVO E-Abstract 1698, Poster Board Number: D0333, 2013

[NPL 7] Mehta J S, et al. ARVO E-Abstract 2198, 2013

[NPL 8] Saisei Iryo [*Regenerative Medicine*] Vol. 10, Extra edition, Page. 201 (Feb. 1, 2011)

[NPL 9] Japanese Journal of Ophthalmology, Vol. 105, Extra edition, Page. 195 (Mar. 15, 2001)

SUMMARY OF INVENTION

Solution to Problem

The present invention provides a marker for identifying corneal cells, especially normal and transformed corneal endothelial cells. Thus, the present invention also provides the following.

(1) A marker for identifying a normal cell and a transformed cell in corneal endothelial cells, comprising at least one marker selected from a normal corneal endothelial cell marker comprising a nucleic acid of a gene selected from the group consisting of CD166, HLA-A2, CD66a, CD66c, CD66d, CD66e, CD98, CD59, CD54, CD340, CD47, EGF-R, CD29, CD74, CD165, CD221, CD49a, SSEA-4, CD130, and CD49f and/or a protein encoded by the nucleic acid, and a transformed corneal endothelial cell marker comprising a nucleic acid of a gene selected from the group consisting of CD26, CD9, CD49b, CD49e, CD13, CD99, CD105, CD63, CD58, CD201, CD56, CD44, CD55, CD71, CD73, CD91, HLA-DQ, CD164, CD49d, CD49c, CD90, MICA/B, CD46, CD140b, CD146, CD147, CD81, CD151, CD200, and CD10 and/or a protein encoded by the nucleic acid.

(2) The marker of item 1, wherein the marker is a cell surface marker.

(3) The marker of item 1 or 2, wherein the marker comprises at least one transformed corneal endothelial cell marker and at least one normal corneal endothelial cell marker.

(4) The marker according to any one of items 1-3, wherein the marker comprises at least one molecule selected from the group consisting of CD98, CD166, and CD340 as the normal corneal endothelial cell marker.

(5) The marker according to any one of items 1-4, wherein the marker comprises at least one molecule selected from the group consisting of CD9, CD49e, CD44, and CD73 as the transformed corneal endothelial cell marker.

(6) The marker according to any one of items 1-5, wherein the marker comprises at least one molecule selected from the group consisting of CD98, CD166, and CD340 as the normal corneal endothelial cell marker and at least one molecule selected from the group consisting of CD9, CD49e, CD44, and CD73 as the transformed corneal endothelial cell marker.

(7) The marker according to any one of items 1-6, wherein the marker comprises at least one marker selected from the group consisting of CD166 and CD73.

(8) A detection agent for identifying a normal corneal endothelial cell and a transformed corneal endothelial cell, comprising a substance that binds to the marker according to any one of items 1-7.

(9) A method of using the marker according to any one of items 1-7 as an indicator for identifying a normal corneal endothelial cell and a transformed corneal endothelial cell.

(10) A method of preparing a corneal endothelial cell sample with an elevated ratio of normal corneal endothelial cells, comprising, a) providing a sample comprising corneal endothelial cells, and b) elevating a ratio of normal corneal endothelial cells while using the marker according to any one of items 1-7 as an indicator in the sample.

(11) An agent for determining purity when making a sample comprising corneal endothelial cells, comprising the marker according to any one of items 1-7 or a substance that binds to the marker.

(12) A method of using the marker according to any one of items 1-7 as an indicator for determining purity when making a sample comprising corneal endothelial cells.

(13) A method of preparing purified corneal endothelial cells, wherein the method comprises:

inducing corneal endothelial cells from undifferentiated cells; and elevating a ratio of the corneal endothelial cells while using the marker according to any one of items 1-7 as an indicator.

(14) The method of item 13, wherein the undifferentiated cells are induced pluripotent stem (iPS) cells or embryonic stem (ES) cells.

(15) A composition comprising a cell prepared by the method of item 10 or 13.

(16) The composition of item 15 for corneal therapy.

(17) The composition of item 16, wherein a subject of the corneal therapy includes corneal endothelial diseases.

Alternatively, the present invention may provide the following.

(A1) A marker for identifying a normal cell and a transformed cell in corneal endothelial cells, comprising at least one marker selected from a normal corneal endothelial cell marker comprising a nucleic acid of a gene selected from the group consisting of CD166, HLA-A2, CD66a, CD66c, CD66d, CD66e, CD98, CD59, CD54, CD340, CD47, EGF-R, CD29, CD74, CD165, CD221, CD49a, SSEA-4, CD130, and CD49f and/or a protein encoded by the nucleic acid, and a transformed corneal endothelial cell marker comprising a nucleic acid of a gene selected from the group consisting of CD26, CD9, CD49b, CD49e, CD13, CD99, CD105, CD63, CD58, CD201, CD56, CD44, CD55, CD71, CD73, CD91, HLA-DQ, CD164, CD49d, CD49c, CD90, MICA/B, CD46, CD140b, CD146, CD147, CD81, CD151, CD200, and CD10 and/or a protein encoded by the nucleic acid.

(A2) The marker of item A1, wherein the marker is a cell surface marker.

(A3) The marker of item A1 or A2, wherein the marker comprises at least one transformed corneal endothelial cell marker and at least one normal corneal endothelial cell marker.

(A4) The marker according to any one of items A1-A3, wherein the marker comprises at least one molecule selected from the group consisting of CD98, CD166, and CD340 as the normal corneal endothelial cell marker.

(A5) The marker according to any one of items A1-A4, wherein the marker comprises at least one molecule selected from the group consisting of CD9, CD49e, CD44, and CD73 as the transformed corneal endothelial cell marker.

(A6) The marker according to any one of items A1-A5, wherein the marker comprises at least one molecule selected from the group consisting of CD98, CD166, and CD340 as the normal corneal endothelial cell marker and at least one molecule selected from the group consisting of CD9, CD49e, CD44, and CD73 as the transformed corneal endothelial cell marker.

(A7) The marker according to any one of items A1-A6, wherein the marker comprises at least one marker selected from the group consisting of CD166 and CD73.

(A8) A detection agent for identifying a normal corneal endothelial cell and a transformed corneal endothelial cell, comprising a substance that binds to the marker according to any one of items A1-A7.
(A9) An agent for diagnosis for identifying a normal corneal endothelium cell and a transformed corneal endothelium cell, comprising a substance that binds to the marker according to any one of items A1-A7.
(A10) The agent for diagnosis of item A9, wherein the corneal endothelial cells are cells present in a living body.
(A11) The agent for diagnosis of item A9 or A10, wherein the diagnosis comprises diagnosis of a corneal endothelial disease.
(A12) The agent for diagnosis of item A11, wherein the corneal endothelial disease is a disease associated with a fibroblast.
(A13) The agent for diagnosis of item A11 or A12, wherein the corneal endothelial disease is selected from the group consisting of bullous keratopathy, corneal endothelial disorders due to trauma or intraocular surgery, and corneal dystrophy including Fuchs corneal endothelial dystrophy and posterior polymorphous corneal endothelial dystrophy.
(A14) The agent for diagnosis according to any one of items A9-A13, wherein a transformed corneal endothelial cell is determined to be comprised when at least one of the transformed corneal endothelial cell marker is expressed.
(A15) An agent for diagnosis of a corneal endothelial cell, comprising a substance that binds to the marker according to any one of items A1-A7, wherein the corneal endothelial cell is diagnosed to be suffering from irreversible dystrophy when at least one of the transformed corneal endothelial cell marker is expressed.
(A16) The agent for diagnosis according to any one of items A9-A15, further comprising an agent for staining the substance that binds to the marker.
(A17) A method of using the marker according to any one of items A1-A7 as an indicator for identifying a normal corneal endothelial cell and a transformed corneal endothelial cell.
(A18) A method of preparing a corneal endothelial cell sample with an elevated ratio of normal corneal endothelial cells, comprising,
a) providing a sample comprising corneal endothelial cells, and
b) elevating a ratio of normal corneal endothelial cells while using the marker according to any one of items A1-A7 as an indicator in the sample.
(A19) An agent for determining purity when making a sample comprising corneal endothelial cells, comprising the marker according to any one of items A1-A7 or a substance that binds to the marker.
(A20) A method of using the marker according to any one of items A1-A7 as an indicator for determining purity when making a sample comprising corneal endothelial cells.
(A21) A method of preparing purified corneal endothelial cells, wherein the method comprises:
inducing corneal endothelial cells from undifferentiated cells; and
elevating a ratio of the corneal endothelial cells while using the marker according to any one of items A1-A7 as an indicator.
(A22) The method of item A21, wherein the undifferentiated cells are induced pluripotent stem (iPS) cells or embryonic stem (ES) cells.
(A23) A composition comprising a cell prepared by the method according to any one of items A18-A22.
(A24) The composition of item A23 for corneal therapy.
(A25) The composition of item 24A, wherein a subject of the corneal therapy includes corneal endothelial diseases.
(B8) A method of detection for identifying a normal corneal endothelial cell and a transformed corneal endothelial cell, comprising: applying a substance that binds to the marker according to any one of items A1-A7 to a sample comprising a corneal endothelial cell; and detecting a binding between the substance and the corneal endothelial cell.
(B9) A method of diagnosis of a corneal endothelial cell, comprising: applying a substance that binds to the marker according to any one of items A1-A7 to a sample comprising the corneal endothelial cell; and detecting a binding between the substance to the cell, wherein a normal corneal endothelial cell and a transformed corneal endothelial cell are identified by determining the presence of the binding.
(B10) The method of item B9, wherein the corneal endothelial cell is a cell present in an organism.
(B11) The method of item B9 or B10, wherein the diagnosis comprises diagnosis of a corneal endothelial disease.
(B12) The method of item B11, wherein the corneal endothelial disease is a disease associated with a fibroblast.
(B13) The method of item B11 or B12, wherein the corneal endothelial disease is selected from the group consisting of bullous keratopathy, corneal endothelial disorder due to trauma or intraocular surgery, and corneal dystrophy including Fuchs corneal endothelial dystrophy and posterior polymorphous corneal endothelial dystrophy.
(B14) The agent for diagnosis according to any one of items B9-B13, wherein the transformed corneal endothelial cell is determined to be comprised when at least one of the transformed corneal endothelial cell marker is expressed.
(B15) A method of diagnosis of a corneal endothelial cell, comprising: applying a substance that binds to the marker according to any one of items A1-A7 to a sample comprising a corneal endothelial cell; and detecting a binding between the substance and the corneal endothelial cell, wherein the corneal endothelial cell is diagnosed to be suffering from irreversible dystrophy when at least one of the transformed corneal endothelial cell marker is expressed.
(B16) The method according to any one of items B9-B15, wherein the substance that binds to the marker further comprises an agent for staining the substance that binds to the marker.
(B19) A method of determining purity when making a sample comprising a corneal endothelial cell, comprising: applying a substance that binds to the marker according to any one of items A1-A7 to a sample comprising the corneal endothelial cell; and detecting a binding between the substance and the cell, wherein a normal corneal endothelial cell and a transformed corneal endothelial cell are identified by determining the presence of the binding.
(B23) A method of therapy or prevention using a cell prepared by the method according to any one of items A18-A22.
(B24) The method of item B23, wherein the therapy or prevention is for a cornea.
(B25) The method of item B24, wherein a subject of the therapy and prevention includes corneal endothelial diseases.

In still another aspect, the present invention provides an agent for diagnosis, a detection kit, a diagnostic kit, a detection system, a diagnostic system or the like using the detection agent, marker or the like of the present invention.

In still another aspect, the present invention provides a therapeutic method, a prevention method, use or the like using the pharmaceutical composition, therapeutic agent or progression preventive agent of the present invention.

It is understood that the present invention can further combine and use one or more of the aforementioned features.

Further embodiments and advantages of the present invention are recognized by those skilled in the art by reading the understanding the following Detailed Description as needed.

ADVANTAGEOUS EFFECTS OF INVENTION

The present invention can identify the cell differentiation capability of corneal endothelial cells to identify cells that are highly functional. As a result, it is possible to treat or prevent corneal endothelial disease or disorder that was previously impossible or difficult. Further, a method of determining purity when making a sample comprising a cell, a method of purifying a corneal endothelial cell, and a method of preparing a purified corneal endothelial cell are also provided.

BRIEF DESCRIPTION OF DRAWINGS

FIG. 1 is a diagram related to solving problems in the production of cultured corneal endothelial cells. A novel surgical procedure for the transplantation of cultured corneal endothelial cells was established in monkey and rabbit models in order to establish novel therapy for corneal endothelial dysfunction. Conventional techniques culture monkey endothelial cells on a type I collagen sheet and transplant a cultured corneal endothelial sheet thereof in a corneal endothelial dysfunction monkey model or inject the cells as a cell suspension into the anterior chamber. The top row in the Figure describes a schematic flow chart for, from the left, separating human corneal endothelial cell from a donor cornea, culturing the cells, and transplanting the cell. The picture on the bottom left shows a corneal endothelium cultured into a normal form, and the bottom right shows a cell transformed by culturing.

FIG. 2 shows images from a phase difference microscope in cultured monkey corneal endothelial cells. The normal corneal endothelial cells shown on the left side show how the cells consist of polygonal, mainly hexagonal, cells. In contrast, the cells transformed into a fibroblast-like shape shown on the right side are not polygonal cells, but have an elongated fibroblast-like shape.

FIG. 3 shows results of flow cytometry analysis on candidate markers in cultured monkey corneal endothelial cells. The left side shows normal cells and the right side shows transformed cells. Further, the top row shows results for CD166 and the bottom row shows results for CD73. It is clearly confirmed from the results that CD166 is highly expressed in normal cells and CD73 is highly expressed in transformed cells.

FIG. 4 shows results of PCR analysis on candidate markers in cultured monkey corneal endothelial cells. The results are for, from the top, CD166, CD73, and GAPDH as a control. The left column is for normal cells and the right column is for transformed cells. It can be clearly confirmed from the results that especially CD166 is highly expressed in normal cells and CD73 is highly expressed in transformed cells. This is consistent with the results of flow cytometry analysis.

FIG. 5 shows images of immunostaining of candidate markers in cultured monkey corneal endothelial cells. The staining is performed using, from the left, CD166 and CD73. The top row shows normal corneal endothelial cells and the bottom row shows transformed cells. It can be seen from the results that CD166 is highly expressed in normal corneal endothelial cells and CD73 is highly expressed in transformed cells. The results are consistent with the results of flow cytometry analysis. The bar indicates 100 μm.

FIG. 6 shows results of images from a phase difference microscope in cultured monkey corneal endothelial cells. The top left shows normal corneal endothelial cells and the top right shows transformed cells. The bottom row shows a mixture of the normal cells and the transformed cells, which was then sorted and cultured depending on the level of CD73 expression. Cells with low level of CD73 expression exhibit a normal polygonal cell form. Meanwhile, cells with high level of CD73 expression exhibit a transformed fibroblast-like form.

FIG. 7 shows results of images of immortalized human corneal endothelial cells from a phase difference microscope. The left shows normal corneal endothelial cells and the middle shows transformed cells. The left shows a cultured mixture of the normal cells and transformed cells. The bar indicates 100 μm.

FIG. 8 examines the CD73 expression of a mixture of normal cells and transformed cells in the immortalized human corneal endothelial cells shown in FIG. 7 by flow cytometry. FIG. 8 shows that the results separate into a high expression peak and a low expression peak for CD73.

FIG. 9 shows a mixture of normal cells and transformed cells in the immortalized human corneal endothelial cells shown in FIG. 7 which is sorted and cultured depending on the CD73 expression by flow cytometry. Cells with low level of CD73 expression exhibit a normal polygonal cell form. In contrast, cells with high level of CD73 expression exhibit a transformed fibroblast-like form. Cells with high and low levels of CD73 expression cultured without sorting are partially comprised of normal cells and partially comprised of transformed cells.

FIG. 10 shows results of analyzing expression of candidate markers after sorting by CD73. The top row shows results after sorting cells with low level of CD73 expression and the bottom row shows results after sorting cells with high level of CD73 expression. The left shows staining by CD73 and the right shows staining by CD166. While cells with low level of CD73 expression had a high level of CD166 expression in immunostaining, cells with high level of CD73 expression had low level of CD166 expression in immunostaining.

FIG. 11 shows results of analyzing expression of function associated markers of corneal endothelial cells after sorting by CD73. The top row shows results after sorting cells with low level of CD73 expression and the bottom row shows results after sorting cells with high level of CD73 expression. The left side shows expression of ZO-1 and the right side shows expression of $Na^1/K^1$-ATPase. Expression of ZO-1 and $Na^+/K^+$-ATPase was observed in cells with low level of CD73 expression in immunostaining.

DESCRIPTION OF EMBODIMENTS

The present invention is described hereinafter. Throughout the entire specification, a singular expression should be understood as encompassing the concept thereof in the plural form unless specifically noted otherwise. Thus, singular articles (e.g., "a", "an", "the" and the like in case of English) should also be understood as encompassing the concept thereof in the plural form unless specifically noted otherwise. Further, the terms used herein should be understood as being used in the meaning that is commonly used in the art, unless specifically noted otherwise. Thus, unless defined otherwise, all terminologies and scientific technical terms that are used herein have the same meaning as the terms commonly understood by those skilled in the art to which the present invention pertains. In case of a contradiction, the present specification (including the definitions) takes precedence.

As used herein, "CD98" is one type of CD protein and a glycoprotein, which is a heterodimer comprised of SLC7A5 (light subunit protein of CD98; also called LAT1, E16, D16S469E, MPE16 or the like. Gene ID (Entrez): 8140 NM_003486; NP_003477) and SLC3A2 (solute carrier family 3 (dibasic and neutral amino acid transport activator) member 2, 4F2hc/CD98; heavy subunit protein of CD98; also called MDU1, 4T2HC, 4F2, or NACAE. The transporter serves a role in intracellular calcium level regulation and transportation of L-amino acid. Gene ID (Entrez): 6520; NM_001013251 (NM_001012661) and NP_001012680) forming a large neutral amino acid transporter 1; LAT1). SEQ ID NOs: 1-4 are representative sequences thereof (SLC3A2=SEQ ID NOs: 1-2; SLC7A5=SEQ ID NOs: 3-4; nucleic acid sequence and amino acid sequence, respectively).

As used herein, "CD166" is a type I transmembrane protein known as activated leukocyte cell adhesion molecule (ALCAM). CD166 is an immunoglobulin superfamily molecule comprising 10 N-linked glycosylation sites. CD166 is comprised of 5 extracellular Ig-like domains, 32 amino acid intracellular terminals and a short transmembrane region with a molecular weight of 100-105 kDa. CD166 is an adhesion molecule forming a binding with a CD6 molecule or a homophilic binding of ALCAM-ALCAM. CD166 is also called ALCAM; CD166; or MEMD. Please also refer to documents PMID: 23056608 and PMID: 18334960. Various accession numbers are Gene ID (Entrez): 214(human), NM_001243280 (mRNA), and NP_001230209 (protein). SEQ ID NOs: 5-6 are representative sequences thereof (nucleic acid sequence and amino acid sequence, respectively).

As used herein, "CD340" is one type of CD known as HER2 or neu oncogene. CD340 is a receptor tyrosine kinase, which is a glycoprotein of about 185 kDa present on the cell surface. CD340 is also called NEU; NGL; HER2; TKR1; CD340; HER-2; MLN 19; or HER-2/neu. CD340 is an oncogene homolog (avian) derived from an erythroblast leukemia ERBB2: virus v-erb-b2. This gene encodes a member of an epithelial growth factor (EGF) receptor family of receptor tyrosine kinases. Since this protein does not have its own ligand binding domain, it is understood that the protein cannot bind to a growth factor. However, it is understood that the protein binds to a member of another ligand binding EGF receptor family member to form a heterodimer to stabilize the ligand binding and enhances kinase mediated activation of a downstream signaling pathway (e.g., mitosis activated protein kinase, phosphatidylinositol-3 kinase and the like). Please refer to the document PMID: 15557433. Entrez Gene ID: (Hu) 2064 and NM_0010005862.1. SEQ ID NOs: 7-8 are representative sequences thereof (nucleic acid sequence and amino acid sequence, respectively).

As used herein, "CD9" is a member of the transmembrane 4 superfamily and is also called tetraspanin. CD9 is also called CD9; BTCC-1; DRAP-27; MIC3; MRP-1; TSPAN-29; or TSPAN29. Tetraspanin is a cell surface glycoprotein with a transmembrane 4 domain and forms a multimer complex with another cell surface protein. A human amniotic epithelial cell (hHEAC) expresses CD9, CD44, CD73, and CD90, as well as negligible levels of CD31, CD34, CD45, and CD117. Please refer to PMID: 21166885. A CD9 gene encodes 1.4 kb of mRNA and is detectably and dominantly expressed in a cornea and at a low level in the ciliary epithelium, retina, iris, and lens. Please refer to the document PMID: 1339429. CD9 is Entrez Gene ID: 928, RefSeq (mRNA): NM_001769 (Hu), RefSeq (protein): NP_001760 (Hu). SEQ ID NOs: 9-10 are representative sequences thereof (nucleic acid sequence and amino acid sequence, respectively).

As used herein, "CD49e" is a protein generally called integrin a5. CD49e is also called ITGAS; CD49e; FNRA; or VLASA. CD49e is also called fibronectin receptor a polypeptide. The α-chain 5 is cleaved in an extracellular domain by a modification after translation to produce a light chain and a heavy chain of disulfide bond, and bind to β1 to form a fibronectin receptor. The promoter for the expression of the molecule is positively regulated through a transcription factor Sp1 by an extracellular matrix component fibronectin in a corneal epithelial cell. Please refer to the document PMID: 10995740. CD49e is Entrez Gene ID: 3678, RefSeq (mRNA): NM_002205 (Hu), RefSeq (protein): NP_002196 (Hu). SEQ ID NOs: 11-12 are representative sequences thereof (nucleic acid sequence and amino acid sequence, respectively).

As used herein, "CD44" is a cell surface glycoprotein that forms cell-cell adhesion or cell-ECM (extra cellular matrix) adhesion. A CD44 molecule exhibits a structure rich in glycans, having multiple N-linked glycan sites, O-linked glycan sites, and chondroitin sulfate binding sites. Phosphorylated serine is present at a portion inside the cell next to a transmembrane section. CD44 is also a receptor of hyaluronic acid (HA) involved in cell movement (metastasis of cancer) and binding to actin through ankyrin. It is understood that CD44 can also interact with other ligands (e.g., osteopontin, collagen, and matrix metalloproteinase (MMP)). A human amniotic epithelial cell (hAEC) expresses CD9, CD44, CD73, and CD90, as well as negligible levels of CD31, CD34, CD45, and CD117. Please refer to the document PMID: 21166885. CD44 is also called CDW44; CSPG8; ECMR-III; HCELL; HUTCH-I; IN; LHR; MC56; MDU2; MDU3; MIC4; or Pgp1. CD44 is Entrez Gene ID: 960, RefSeq (mRNA): NM_000610, and RefSeq (protein): NP_000601. SEQ ID NOs: 13-14 are representative sequences thereof (nucleic acid sequence and amino acid sequence, respectively).

As used herein, "CD73" is an enzyme also called ecto-5'-nucleotidase, which converts AMP into adenosine. CD73 is also called NTSE; CD73; ESNT; NT; NTS; NTE; eN; or eNT. A protein encoded by this gene is a plasma membrane protein catalyzing a reaction that converts an extracellular nucleotide into a transmembrane nucleoside. A human amniotic epithelial cell (hAEC) expresses CD9, CD44, CD73, and CD90, as well as negligible levels of CD31, CD34, CD45, and CD117. An isolated corneal keratocyte exhibits a fibroblast-like shape and expresses CD13, CD29, CD44, CD56, CD73, CD90, CD105, and CD133, but is negative for HLA-DR, CD34, CD117, and CD45. These properties are similar to those of BM-MSC (bone marrow mesenchymal stem cells). It is understood that marginal bone marrow mesenchymal stem cells (L-MSC) are CD34, CD34, CD90ǀ, CD73ǀ, and CD105ǀ. Please refer to the documents PMID: 21166885, PMID: 17464757 and PMID: 22587591. CD73 is Entrez Gene ID: 4907, RefSeq (mRNA): NM_001204813, and RefSeq (protein): NP_001191742. SEQ ID NOs: 15-16 are representative sequences thereof (nucleic acid sequence and amino acid sequence, respectively).

For other CDs, information in, for example, http://hcdm.org/index.php/component/molecule/?Itemid=132 can be referred. Further, the following is known, and such information can be utilized for the implementation of the present invention. The content of such information is incorporated herein by reference as needed.

TABLE 1

| CD and explanation thereof | Accession number of human amino acid sequence | Accession number of human nucleic acid sequence | Entrez Gene ID: |
|---|---|---|---|
| HLA-A2 (See Komlos L. Klein T. Korostishevsky M (2007). "HLA-A2 class I antigens in couples with recurrent spontaneous abortions". *Int. J. Immunogenet.* 34 (4): 241-6 and the like) | — | — | — |
| CD66a(CEACAM1) | NM_001024912 | NP_001020083 | Entrez 634 |
| CD66c(CEACAM6) | NM_002483 | NP_002474 | Entrez 4680 |
| CD66d(CEACAM3) | NM_001277163 | NP_001264092 | Entrez 1084 |
| CD66e(CEACAM5) | NM_004363 | NP_004354 | Entrez 1048 |
| CD59 (MAC-IP) complement control protein is a cell surface glycoprotein which controls complement-mediated cytolysis. It is associated with lymphocyte signaling. Corneal cells are known to be resistant to complements. Relation to high level of CD59 expression in corneal epithelium is considered See document PMID: 16061345 (Sladowski D et al., Toxicol In Vitro2005 Oct: 19(7): 875-8) | NM_000611 | NP_000602 | Entrez 966 |
| CD54(ICAM-1) | NM_000201 | NP_000192 | Entrez 3383 |
| CD47(IAP) | NM_001025079 | NP_001768 | Entrez 961 |
| EGF-R | NM_005228 | NP_005219 | Entrez 1956 |
| CD29(ITGB1) integrin β1 (fibronectin receptor, β polypeptide, CD29 includes MDF2, MSK12). Required for maintaining the integrity of a corneal structure. See document PMID: 21873663 (Parapuram SK et al., Invest Ophthalmol Vis Sci. 2011 Oct. 3: 52(11): 7799-806) | NM_002211 | NP_002202 | Entrez 3688 |
| CD74(HLADG) | NM_001025158 | NP_001020329 | Entrez 972 |
| CD165: a difference is observed in molecular phenotypes and differentiation potency for human stromal (mesenchymal) stem cells (MSC) from the bone marrow, fat tissue and skin. A microarray-based study has found 33 common MSC molecular signatures, including CD165, CD276, and CD82. See document PMID: 22529014(Al-Nbaheen M et al., Stem Cell Rev. 2013 Feb: 9(1): 32-43) | — | — | Gene ID: 23449 |
| CD221 | NM_000875 | NP_000866 | Entrez 3480 |
| CD49a(ITGA1) | NM_181501 | NP_852478 | Entrez 3672 |
| See SSEA-4 (Stage Specific Embryonic Antigen-4: Neurochem Res. 2011 Sep: 36(9): 1623-35 and the like | — | — | — |
| CD130(gp130, IL6ST, IL6-beta) | NM_001190981 | NP_001177910 | Entrez 3572 |
| CD49f(ITGA6) | NM_000210 | NP_000201 | — |
| CD26(DPP4) | NM_001935 | NP_001926 | Entrez 1803 |
| CD49b(ITGA2) | NM_002203 | NP_002194 | Entrez 3673 |
| CD13(ANPEP) | NM_001150 | NP_001141 | Entrez 290 |
| CD99(MIC2) | NM_001122898 | NP_001116370 | Entrez 4267 |
| CD105(Endoglin) | NM_000118 | NP_000109 | Entrez 2022 |

TABLE 1-continued

| CD and explanation thereof | Accession number of human amino acid sequence | Accession number of human nucleic acid sequence | Entrez Gene ID: |
|---|---|---|---|
| CD63 (LAMP-3): This molecule is a member of the transmembrane 4 superfamily, belonging to the tetraspanin family. CD63 is a cell surface glycoprotein, complexed with integrins. CD63 may also function as a platelet activation marker. | NM_001040034 | NP_001244318 | Entrez 967 |
| CD58(LFA-3) | NM_001779 | — | Entrez 965 |
| CD201(EPCR) | NM_006404 | NP_006395 | Entrez 10544 |
| CD56(NCAM) | NM_000615 | NP_000606 | Entrez 4684 |
| CD55(DAF) | NM_000574 | NP_000565 | Entrez 1604 |
| CD71(TfR1) | NM_001128148 | NP_001121620 | Entrez 7037 |
| CD91(LRP1) | NM_002332 | NP_002323 | Entrez 4035 |
| HLA-DQ, T-lymphocyte is activated by a corneal endothelial cell, and HLA-DP, -DQ, DR, and CD40 expression increases by pretreatment with γ interferon See document PMID: 18552515(Wang F., Ophthalmologica. 2008: 222(4): 272-6) Induction of class II antigens in human corneal epithelial cells is independently regulated by interferon γ for each antigen. DQ induction may depend on differentiation of cultured human corneal epithelial cells. See document PMID: 1639617(Iwata M, et al., Invest Ophthalmol Vis Sci. 1992 Aug: 33(9): 2714-21) | | (HLA-DQA1 and HLA-DQB1) | |
| ,HLA-DQA1 | NM_002122 | NP_002113 | Entrez 3117 |
| ,HLA-DQB1 | NM_001243961 | NP_001230890 | Entrez 3119 |
| CD164 | NM_001142401 | NP_001135873 | Entrez 8763 |
| CD49d | NM_000885 | NP_000876 | Entrez 3676 |
| CD49c(ITGA3) | NM_002204 | NP_002195 | Entrez 3675 |
| CD90(Thy-1) | NM_006288 | NP_006279 | Entrez 7070 |
| MICA/B | | (MICA (MHC class I chain-related gene A), MICB (MHC class I chain-related gene B)) | |
| MICA: | NM_000247 | NP_000238 | Entrez 100507436 |
| MICB: | NM_005931 | NP_005922 | Entrez 4277 |
| CD46 | NM_002389 | NP_002380 | Entrez 4179 |
| CD140b(PDGFRB = Platelet-derived growth factor receptor, β polypeptide | NM_002609 | NP_002600 | Entrez 5159 |
| CD146(MCAM | MUC18) | NM_006500 NP_006491 | Entrez 4162 |
| CD147(Basigin (BSG), EMMPRIN) | NM_001728 | NP_001719 | Entrez 682 |
| CD8 1 | NM_004356 | NP_004347 | Entrez 975 |
| CD151 | NM_001039490 | NP_001034579 | Entrez 977 |
| CD200 (OX-2 membrane glycoprotein), may regulate bone marrow cell activity and transmits inhibition signals for the macrophage system in various tissues. An HSV infection results in infiltration into the cornea by CD200R(+) cells. Most of the cells are CD11 (+). See document PMID: 19070547(Sarangi PP et al., Clin Immunol. 2009 Apr; 131(1): 31-40) | NM_001004196 | NR_001004196 | Entrez 4345 |
| CD10(Neprilysin, NEP, CALLA) | NM_000902 | NP_000893 | Entrez 4311 |

It is understood that each CD name refers to not only a protein (or a nucleic acid encoding the same) having the amino acid sequence described by the specific accession number (and SEQ ID NOs when specifically described herein), but also functionally active derivatives thereof, functionally active fragments thereof, homologs thereof, and mutants encoded by a nucleic acid that hybridizes to a nucleic acid encoding the protein under a highly or lowly stringent condition.

The same applies to all other proteins mentioned in the present invention. Thus, the predetermined names of proteins or nucleic acids not only refer to proteins or nucleic acids set forth in Sequence Listing, but also functionally active derivatives, functionally active fragments thereof, homologs thereof, and mutants encoded by a nucleic acid that hybridizes to a nucleic acid encoding the protein under a highly or lowly stringent condition, preferably under conditions discussed above. As used herein, a "derivative", "analog of a constituent protein", or "mutant" preferably includes a molecule comprising a region substantially homologous to a constituent protein, but not intended to be limited thereto. Such a molecule is at least 30%, 40%, 50%, 60%, 70%, 80%, 90%, 95% or 99% identical throughout the amino acid sequence of the same size or compared to a sequence aligned by a homology computer program known in the art in various embodiments. Alternatively, a nucleic acid encoding such a molecule can hybridize to a sequence encoding the constituent protein under a stringent condition, moderately stringent condition, or non-stringent condition. This is the outcome of modifying a naturally-occurring protein by an amino acid substitution, deletion and addition, respectively, and indicates that a derivative thereof exhibits the biological function of the naturally-occurring protein, although not necessarily to the same degree. For instance, the biological function of such a protein can be studied by a suitable and available in vitro assay described herein or known in the art. The discussion in the present invention mainly pertains to humans, but it is understood that the discussion is applicable to other species, such as other species within primates, or animal species in other genera. It is understood that mammals are within the scope of the present invention.

As used herein, "functionally active" refers to polypeptides of the present invention, i.e., polypeptides having a structural function, regulatory function or biochemical function of a protein such as biological activity according to an embodiment associated with the fragments or derivatives of the present invention.

In the present invention, a "fragment" of a molecule such as CD98 is a polypeptide comprising any region of the molecule such as CD98. As long as the fragment can be used for the objective of the present invention (e.g., detection, diagnosis, or the like), the fragment may not have the natural biological function of the molecule. An example of a fragment includes, but is not limited to, a fragment comprising an extracellular region of a molecule such as CD98.

A representative nucleotide sequence of a molecule such as CD98 may be:
(a) a polynucleotide having a base sequence set forth in SEQ ID NO: X or a fragment sequence thereof;
(b) a polynucleotide encoding a polypeptide consisting of the amino acid sequence set forth in SEQ ID NO: X+1 or a fragment thereof,
(c) a polynucleotide encoding a variant polypeptide having a mutation selected from the group consisting of substitution, addition and deletion in one or more amino acids in the amino acid sequence set forth in SEQ ID NO: X+1, or a fragment thereof, where the variant polypeptide has biological activity;
(d) a polynucleotide, which is a splice mutant or allelic mutant of the base sequence set forth in SEQ ID NO: X, or a fragment thereof,
(e) a polynucleotide encoding a species homolog of a polypeptide consisting of the amino acid sequence set forth in SEQ ID NO: X+1 or a fragment thereof,
(f) a polynucleotide encoding a polypeptide having biological activity and hybridizing to the polynucleotide according to any one of (a)-(e) under a stringent condition; or
(g) a polynucleotide encoding a polypeptide having biological activity and consisting of the polynucleotide according to any one of (a)-(e) or base sequence having at least 70% identity to a complement sequence thereof. Herein, biological activity typically refers to activity of a molecule such as CD98.

The amino acid sequence of a molecule such as CD98 may be:
(a) a polypeptide consisting of the amino acid sequence set forth in SEQ ID No.: X+1 or a fragment thereof;
(b) a polypeptide having one mutation selected from the group consisting of substitution, addition and deletion in one or more amino acids in the amino acid sequence set forth in SEQ ID NO: X+1 and having biological activity;
(c) a polypeptide encoded by a splicing mutant or an allele mutant of the base sequence set forth in SEQ ID NO: X+1;
(d) a polypeptide which is a species homolog of the amino acid sequence set forth in SEQ ID NO: X+1; or
(e) a polypeptide having an amino acid sequence having at least 70% identity to the polypeptide according to any one of (a)-(d), and having biological activity.

Herein, SEQ ID NO: X (X is an odd number from 1-15) indicates a nucleic acid sequence of a molecule (including a subunit) such as CD98. X=1 is a heavy subunit protein of CD98, X=3 is a light subunit protein of CD98, X=5 is CD166, X=7 is CD340, X=9 is CD9, X=11 is CD49e, X=13 is CD44, and X=15 is CD73. Biological activity typically refers to activity of a molecule such as CD98. Further, the nucleic acid sequences of SEQ ID NOs: 1-15 may comprise a sequence other than CDR (coding region). Such regions can also be used as a primer or a probe. In other embodiments, only CDR may be utilized as a nucleic acid region.

As used herein, "such as CD98" refers to any marker in the present invention. More specifically, markers expressed significantly more in normal cells than transformed cells include, but not limited to, CD166, HLA-A2, CD66a, CD66c, CD66d, CD66e, CD98, CD59, CD54, CD340, CD47, EGF-R, CD29, CD74, CD165, CD221, CD49a, SSEA-4, CD130, and CD49f. Markers expressed significantly more in transformed cells than in normal cells include, but not limited to, CD26, CD9, CD49b, CD49e, CD13, CD99, CD105, CD63, CD58, CD201, CD56, CD44, CD55, CD71, CD73, CD91, HLA-DQ, CD164, CD49d, CD49c, CD90, MICA/B, CD46, CD140b, CD146, CD147, CD81, CD151, CD200, and CD10.

In the context of the present invention, "substance that binds to a molecule such as CD98" or "molecular interaction molecule such as CD98" is a molecule or substance that binds at least transiently to a molecule such as CD98 and is preferably capable of indicating that the molecule or substance is bound (i.e., labelled or labelable state). A substance that binds to a molecule such as CD98 may be an inhibitor of the molecule such as CD98. Examples thereof include antibodies, antisense oligonucleotides, siRNA, low molecular weight molecules (LMW), binding peptides, aptamers, ribozymes, peptidomimetics and the like, as well as, for instance, binding proteins or binding peptides directed to a molecule such as CD98, especially those directed to an active site of the molecule such as CD98 and nucleic acids directed to a gene of the molecule such as CD98. A nucleic acid for a molecule such as CD98 refers to, for example, double stranded or single stranded DNA or RNA for inhibiting the expression of a gene of the molecule such as CD98 or activity of a molecule such as CD98 or a modified product or derivative thereof, including, without limitation, antisense nucleic acid, aptamers, siRNA (small interfering RNA) and ribozymes. As used herein, "binding protein" or "binding peptide" with respect to a molecule such as CD98 refers to a type of protein or peptide that binds to the molecule such as CD98, and includes, but is not limited to, polyclonal antibodies or monoclonal antibodies, antibody fragments and protein backbones directed to the molecule such as CD98.

As used herein, "protein", "polypeptide", "oligopeptide" and "peptide" are used herein to have the same meaning and refer to a polymer of amino acids with any length. The polymer may be straight, branched or cyclic. An amino acid may be a natural-occurring, non-naturally occurring or modified amino acid. The term may also encompass those assembled into a complex of multiple polypeptide chains. The term also encompasses naturally-occurring or artificially modified amino acid polymers. Examples of such a modification include disulfide bond formation, glycosylation, lipidation, acetylation, phosphorylation, and any other manipulation or modification (e.g., conjugation with a labeling component). The definition also encompasses, for example, polypeptides comprising one or more analogs of an amino acid (e.g., including non-naturally occurring amino acids and the like), peptide-like compounds (e.g., peptoids) and other known modifications in the art.

As used herein, "amino acid" may be naturally-occurring or non-naturally-occurring amino acids as long as the objective of the present invention is met.

As used herein, "polynucleotide", "oligonucleotide" and "nucleic acid" are used herein to have the same meaning, and refer to a polymer of nucleotides with any length. The term also encompasses "oligonucleotide derivative" and "polynucleotide derivative". "Oligonucleotide derivative" and "polynucleotide derivative" refer to an oligonucleotide or polynucleotide that comprises a nucleotide derivative or has a linkage between nucleotides which is different from normal. The terms are used interchangeably. Specific examples of such an oligonucleotide include 2'-O-methyl-ribonucleotide, oligonucleotide derivatives having a phosphodiester linkage in an oligonucleotide converted to a phosphorothioate linkage, oligonucleotide derivatives having a phosphodiester linkage in an oligonucleotide converted to an N3'-P5' phosphoramidate linkage, oligonucleotide derivatives having ribose and phosphodiester linkage in an oligonucleotide converted to a peptide nucleic acid linkage, oligonucleotide derivatives having uracil in an oligonucleotide replaced with C-5 propinyluracil, oligonucleotide derivatives having uracil in an oligonucleotide replaced with C-5 thiazoluracil, oligonucleotide derivatives having cytosine in an oligonucleotide replaced with C-5 propinylcytosine, oligonucleotide derivatives having cytosine in an oligonucleotide replaced with phenoxazine-modified cytosine, oligonucleotide derivatives having ribose in DNA replaced with 2'-O-propylribose, oligonucleotide derivatives having ribose in an oligonucleotide replaced with 2'-methoxyethoxyribose and the like. Unless noted otherwise, specific nucleic acid sequences are also intended to encompass conservatively modified variants (e.g., degenerate codon substitute) and complement sequences as in the expressly shown sequences. Specifically, degenerate codon substitutes can be achieved by preparing a sequence with the third position of one or more selected (or all) codons substituted with a mixed base and/or deoxyinosine residue (Batzer et al., Nucleic Acid Res. 19: 5081(1991); Ohtsuka et al., J. Biol. Chem. 260: 2605-2608 (1985); Rossolini et al., Mol. Cell. Probes 8: 91-98 (1994)). As used herein, "nucleic acid" is used interchangeably with a gene, cDNA, mRNA, an oligonucleotide, and polynucleotide. As used herein, a "nucleotide" may be a naturally-occurring or non-naturally occurring amino acid.

As used herein, "gene" refers to an agent defining a genetic trait. A gene is generally arranged in a certain order on a chromosome. A gene defining the primary structure of a protein is referred to as a structural gene and a gene determining the expression thereof is referred to as a regulator gene. As used herein, "gene" may refer to "polynucleotide", "oligonucleotide" and "nucleic acid". A "gene product" is a substance produced based on a gene and refers to a protein, mRNA or the like.

As used herein, "homology" of genes refers to the level of identity of two or more genetic sequences with one another. In general, having "homology" refers to having a high level of identity or similarity. Thus, two genes with high homology have higher identity or similarity of sequences. It is possible to find whether two types of genes have homology by direct comparison of sequences or, in the case for nucleic acids, by a hybridization method under a stringent condition. When two genetic sequences are directly compared, the genes are homologous when DNA sequences are representatively at least 50% identical, preferably at least 70% identical, and more preferably at least 80%, 90%, 95%, 96%, 97%, 98%, or 99% identical between the genetic sequences. Thus, as used herein, "homolog" or "homologous gene product" refers to a protein in another species, preferably mammal, exerting the same biological function as a protein constituent of a complex which will be further described herein. Such a homolog is also called "ortholog gene product". An algorithm for detecting orthologous gene pair from humans and mammals or another species uses the entire genome of these organisms. First, an expected complete Smith-Waterman alignment of a protein is used to a collect a pairwise best hit. To further improve the reliability, a pairwise best hit comprising *Drosophila melanogaster* and *C. elegans* proteins may be used to form a cluster of pairs. Such analysis is provided in, for example, Nature, 2001, 409: 860-921. Based on sequence homology of genes encoding the proteins provided herein with respect to genes of other species, it is also possible to isolate a homolog of the proteins described herein by applying a conventional technique to clone each gene and allowing a protein from such genes to be expressed or by isolating a similar complex to isolate a protein of another species in accordance with the method provided herein or in accordance with other suitable methods well known in the art.

Amino acids may be mentioned herein by either the common, known three letter symbol thereof or by a one character symbol recommended by the IUPAC-IUB Biochemical Nomenclature Commission. Nucleotides may similarly be mentioned by a commonly recognized one character code. Comparison of similarity, identity and homology of an amino acid sequence and a base sequence is calculated herein by using a default parameter using BLAST, which is a sequence analysis tool. For example, identity can be searched by using BLAST 2.2.9 (published on May 12, 2004) of NCBI. Herein, values for identity generally refer to a value obtained by alignment under the default condition using the above-described BLAST. However, when a higher value is obtained by changing a parameter, the highest value is considered the value of identity. When identity is evaluated in multiple regions, the highest value thereamong is considered the value of identity. Similarity is a value by taking into consideration similar amino acid in addition to identity into the calculation.

As used herein, polynucleotide which "hybridizes under a stringent condition" refers to commonly used, well-known conditions in the art. Such a polynucleotide can be obtained by using a method such as colony hybridization, plaque hybridization, or southern blot hybridization while using a polynucleotide selected from among the polynucleotides of the present inventions as a probe. Specifically, the above-described polynucleotide refers to a polynucleotide that can be identified by using a filter with immobilized DNA from a colony or plaque and performing hybridization at 65° C. in the presence of 0.7-1.0 M NaCl and then using an SSC (saline-sodium citrate) solution with 0.1-2 times concentration (composition of an SSC solution with 1 time concentration is 150 mM sodium chloride and 15 mM sodium citrate) and washing the filter under the condition of 65° C. Hybridization can be performed in accordance with the method described in an experimental manual such as Molecular Cloning 2nd ed., Current Protocols in Molecular Biology, Supplement 1-38, DNA Cloning 1: Core Techniques, A Practical Approach, Second Edition, Oxford University Press (1995) or the like. In this regard, sequences comprising only A sequence or T sequence are preferably excluded from the sequence that hybridizes under a stringent condition. Thus, the polypeptides used in the present invention (e.g., transthyretin and the like) also encompass polypeptides encoded by a nucleic acid molecule that hybridizes under stringent condition to a nucleic acid molecule encoding a polypeptide especially described in the present invention. Such low stringency conditions include hybridization for 18-20 hours at 40° C. in a buffer solution comprising 35% formamide, 5×SSC, 50 mM Tris-HCl (pH 7.5), 5 mM EDTA, 0.02% polyvinylpyrrolidone (PVP), 0.02% BSA, 100 µg/ml denatured salmon sperm DNA, and 10% (w/v) dextran sulfate, washing 1-5 hours at 55° C. in a buffer consisting of 2×SSC, 25 mM Tris-HCl (pH 7.4), 5 mM EDTA and 0.1% SDS, and washing for 1.5 hours at 60° C. in a buffer consisting of 2×SSC, 25 mM Tris-HCl (pH 7.4), 5 mM EDTA, and 0.1% SDS.

As used herein, a "purified" substance or biological agent (e.g., nucleic acid or protein) refers to a substance or a biological agent from which at least a part of an agent naturally associated with the biological agent has been removed. Thus, the purity of a biological agent in a purified biological agent is generally higher than the purity in the normal state of the biological agent (i.e., concentrated). The term "purified" as used herein refers to the presence of preferably at least 75% by weight, more preferably at least 85% by weight, still more preferably at least 95% by weight, and most preferably at least 98% by weight of the same type of a biological agent. A substance used in the present invention is preferably a "purified" substance.

As used herein, a "corresponding" amino acid or nucleic acid refers to an amino acid or a nucleotide which has or is expected to have, in a certain polypeptide molecule or polynucleotide molecule, similar action as a predetermined amino acid or nucleotide in a benchmark polypeptide or a polynucleotide, and, particularly in the case of enzyme molecules, refers to an amino acid which is present at a similar position in an active site and makes a similar contribution to catalytic activity. For example, for an antisense molecule, it can be a similar part in an ortholog corresponding to a specified part of the antisense molecule. A corresponding amino acid can be a specified amino acid subjected to, for example, cysteination, glutathionylation, S—S bond formation, oxidation (e.g., oxidation of methionine side chain), formylation, acetylation, phosphorylation, glycosylation, myristylation or the like. Alternatively, a corresponding amino acid can be an amino acid responsible for dimerization. Such a "corresponding" amino acid or nucleic acid may be a region or a domain over a certain range. Thus, it is referred herein as a "corresponding" region or domain in such a case.

As used herein, a "corresponding" gene (e.g., polynucleotide sequence or molecule) refers to a gene (e.g., polynucleotide sequence or molecule) of a certain species which has or is expected to have similar action as that of a predetermined gene in a benchmark species. When there is a plurality of genes having such action, the corresponding gene refers to a gene having the same evolutionary origin. Thus, a corresponding molecule such as CD98 can be found in humans for each of molecules such as CD98 of mice and rats. Such a corresponding gene can be identified by using a technique that is well known in the art. For example, a corresponding gene in a certain animal (e.g., mouse, or rat) can be found by searching a sequence database of the animal using the sequence of SEQ ID NO: 1 or the like as a query sequence as a benchmark gene of a corresponding gene (e.g., of a human).

As used herein, a "fragment" refers to a polypeptide or a polynucleotide having a sequence length of 1 to n−1, relative to a full length polypeptide or polynucleotide (length: n). The length of the fragment can be appropriately changed depending on the objective thereof. Examples of the lower limit of the length for a polypeptide include 3, 4, 5, 6, 7, 8, 9, 10, 15, 20, 25, 30, 40, 50 and more amino acids. A length represented by an integer which is not specifically listed herein (e.g., 11 or the like) can also be appropriate as the lower limit. For a polynucleotide, examples of the lower limit include 5, 6, 7, 8, 9, 10, 15, 20, 25, 30, 40, 50, 75, 100 and more nucleotides. A length represented by an integer which is not specifically listed herein (e.g., 11 or the like) can also be appropriate as the lower limit. For such a fragment as used herein, it is understood, for example, that when a full length polypeptide or polynucleotide functions as a marker, the fragment itself is also within the scope of the present invention as long as it functions as a marker.

According to the present invention, the term "activity" as used herein refers to the function of a molecule in a broadest sense. The activity is not intended to be particularly limited, but generally includes a biological function, a biochemical function, a physical function or a chemical function of a molecule. The activity includes, for example, an enzyme activity, an ability to interact with other molecules, an ability to activate, promote, stabilize, inhibit, suppress, or destabilize the function of other molecules, stability, and an ability to be localized at a specific position in a cell. When applicable, this term also relates to the function of a protein complex in a broadest sense.

As used herein, "biological function", when referring to a certain gene or a nucleic acid molecule or a polypeptide related thereto, refers to a specific function that the gene, the nucleic acid molecule or the polypeptide may have in a living body. Examples of such a function include, but are not limited to, production of a specific antibody, enzyme activity, impartation of resistance and the like. In the present invention, examples of this function include, but are not limited to, a function of CD98 or the like of recognizing a ligand. Documents cited by an Entrez number, accession number or the like listed in the aforementioned Tables can be referred for such biological activity. Such documents or the like are incorporated herein by reference. As used herein, biological function can be exerted by "biological activity". As used herein, "biological activity" refers to the activity a certain agent (e.g., polynucleotide, protein or the like) may have in a living body. Biological activity encompasses an activity of exerting a variety of functions (e.g., transcription promoting activity), and also encompasses, for example, an activity that activates or inactivates another molecule by an interaction with a certain molecule. When two agents interact, biological activity thereof is understood to be binding between two molecules and a biological change induced thereby. For example, two molecules are considered to be bound together if, when one molecule is precipitated using an antibody, the other molecule co-precipitates. Observation of such co-precipitation is one example of a determination procedure. For example, when a certain agent is an enzyme, the biological activity thereof encompasses enzyme activity. In another example, when a certain agent is a ligand, binding to a receptor corresponding to the ligand is encompassed. Such biological activity can be measured by a technique that is well known in the art. Thus, "activity" refers to various measurable indicators, which indicate or reveal binding (either direct or indirect) or affect a response (i.e., having a measurable effect in response to some exposure of stimulus). Examples thereof includes affinity of a compound that directly binds to the polypeptide or polynucleotide of the present invention, the amount of proteins upstream or downstream after some stimulations or events, or the measure of other similar functions.

As used herein, "expression" of a gene, a polynucleotide, a polypeptide or the like refers to the gene or the like being subjected to a certain action in vivo to be converted into another form. Preferably, expression refers a gene, a polynucleotide or the like being transcribed and translated into a form of a polypeptide. However, transcription to make mRNA can also be one embodiment of expression. More preferably, such a form of a polypeptide can be a form which has undergone processing after translation (derivative as is referred to herein). For example, the expression level of a molecule such as CD98 can be determined by any method. Specifically, the expression level of a molecule such as CD98 can be found by evaluating the amount of mRNA of a molecule such as CD98, the amount of protein of a molecule such as CD98, and the biological activity of protein of a molecule such as CD98. The amount of mRNA or a protein of a molecule such as CD98 can be determined by the method described herein.

As used herein, it is understood that a "molecule such as CD98 or functional equivalent thereof" or a "group consisting of molecule such as CD98 and functional equivalents thereof" refers to, in addition to the molecule such as CD98 itself, mutants or variants of the molecule such as CD98 (e.g., amino acid sequence variant and the like) which have an action of controlling differentiation and/or promoting proliferation of ocular cells or the like or function as a marker described herein, as well as those that can be changed into the molecule such as CD98 itself or a mutant or a variant thereof (e.g., including nucleic acids encoding the molecule such as CD98 itself or a mutant or a variant of the molecule such as CD98, vectors, cells and the like comprising the nucleic acid) at the time of action. In the present invention, it is understood, even when not specifically mentioned, that a functional equivalent of a molecule such as CD98 can be used similarly to the molecule such as CD98.

A functional equivalent of a molecule such as CD98 used in the present invention can be found by searching a database or the like. As used herein, "search" refers to finding another nucleic acid base sequence having a specific function and/or property by utilizing a certain nucleic acid base sequence with electronic, biological, or other methods. Electronic search includes, but is not limited to, BLAST (Altschul et al., J. Mol. Biol. 215: 403-410 (1990)), FASTA (Pearson & Lipman, Proc. Natl. Acad. Sci., USA 85: 2444-2448 (1988)), Smith and Waterman method (Smith and Waterman, J. Mol. Biol. 147: 195-197 (1981)), Needleman and Wunsch method (Needleman and Wunsch, J. Mol. Biol. 48: 443-453 (1970)) and the like. Biological search includes, but is not limited to, stringent hybridization, microarray in which genomic DNA is applied on a nylon membrane, glass plate or the like (microarray assay), PCR, in situ hybridization and the like. Herein, genes used in the present invention are intended to include corresponding genes identified by such electronic or biological search.

An amino acid sequence with an insertion, substitution, deletion, or addition to one or both ends thereof of one or more amino acids can be used as a functional equivalent of the present invention. As used herein, "amino acid sequence with an insertion, substitution, deletion, or addition to one or both ends thereof of one or more amino acids" means that a sequence is modified by a well-known technical method such as site-specific mutagenesis, or by substitution of a plurality of amino acids to the extent that may occur naturally by natural mutations.

A modified amino acid sequence of a molecule such as CD98 can be a sequence with, for example, insertion, substitution, deletion, or addition to one or both ends, of 1 to 30, preferably 1 to 20, more preferably 1 to 9, still more preferably 1 to 5, and especially preferably 1 to 2 amino acids. A modified amino acid sequence may be an amino acid sequence of a molecule such as CD98 preferably having one or more (preferably, 1 or a few, or 1, 2, 3 or 4) conservative substitutions. Herein, "conservative substitution" refers to substitution of one or more amino acid residues with other chemically similar amino acid residues so that the function of a protein is not substantially modified. Examples thereof include substitution of a certain hydrophobic residue with another hydrophobic residue, substitution of a certain polar residue with another polar residue having the same charge, and the like. A functionally similar amino acid which can be subjected to such substitution is known in the art for every amino acid. Specific examples thereof as a non-polar (hydrophobic) amino acid include alanine, valine, isoleucine, leucine, proline, tryptophan, phenylalanine, methionine and the like. Examples thereof as a polar (neutral) amino acid include glycine, serine, threonine, tyrosine, glutamine, asparagine, cysteine and the like. Examples thereof as a (basic) amino acid having a positive charge include arginine, histidine, lysine and the like. Further, examples thereof as an (acidic) amino acid having a negative charge include aspartic acid, glutamic acid and the like.

As used herein, a "marker (substance, protein, or gene (nucleic acid))" refers to a substance which serves as a indicator for tracking whether a cell is in a certain state (e.g., the level or presence of a normal cell state, a transformed state, a disease state, a disorder state, a proliferation ability, or a differentiated state), or whether there is risk thereof. Examples of such a marker include genes (nucleic acid=DNA level), gene products (mRNA, protein and the like), metabolites, enzymes and the like. In the present invention, detection, diagnosis, preliminary detection, prediction or advance diagnosis of a certain state (e.g., a disease such as differentiation disorder) can be realized using an agent or means specific to a marker associated with the state, or a composition, a kit, a system or the like comprising them. As used herein, "gene product" refers to mRNA or a protein encoded by a gene. It was found herein that a gene product which has not been shown to be associated with an ocular cell (i.e. molecule such as CD98, etc.) can be used as an indicator of whether an ocular cell, especially a corneal endothelial cell, is normal (whether the cell is transformed).

As used herein, "nerve cell" is used in a broad sense, referring to any cell included in an organ of the nervous system. It is understood in particular that cells derived from a neural crest cell (e.g., corneal endothelial cell and the like) are also encompassed.

As used herein, "ocular cell" is used in a broad sense, referring to any cell in an eye. Any cell in the eyelid, sclera, cornea, uvea, crystalline lens, vitreous body, retina, and optic nerve is encompassed thereby.

As used herein, "corneal endothelial cell" is used in the general sense used in the art. The cornea is one of the lamellar tissues constituting an eye. A cornea is transparent and is positioned at a part closest to the external environment. In humans, it is understood that the cornea is composed of five layers in order of corneal epithelium, Bowman's membrane (external boundary), Lamina propria, Descemet's membrane (internal boundary), and corneal endothelium from the outside (body surface). Unless specifically noted otherwise, parts other than epithelium and endothelium may be collectively called "corneal stroma", which is also called as such herein.

As used herein, "corneal tissue" is used in the general sense, referring to the tissue itself constituting the cornea. When referring to a corneal tissue, it may include all constituents of a cornea, i.e., corneal epithelium, Bowman's membrane (external boundary), Lamina propria, Descemet's membrane (internal boundary), and corneal endothelium (for humans; for other animals, all corresponding sections thereof), lack a part, or include another tissue (sclera) in addition to the cornea, which may be particularly called sclerocornea. Thus, a sclerocornea or a sclerocornea fragment is recognized as one embodiment of a corneal tissue.

As used herein, "normal corneal endothelial cell marker" refers to a marker, which is expressed in a normal corneal endothelial cell and has significantly reduced amount of expression when transformed. Threshold values of expression in normal cells include, but are not limited to, about 1.01 times or more, about 1.02 times or more, about 1.03 times or more, about 1.04 times or more, about 1.05 times or more, about 1.1 times or more, about 1.2 times or more, about 1.3 times or more, about 1.4 times or more, about 1.5 times or more, about 1.6 times or more, about 1.7 times or more, about 1.8 times or more, about 1.9 times or more, about 2 times or more, about 2.5 times or more, about 3 times or more, about 3.5 times or more, about 4 times or more, about 4.5 times or more, about 5 times or more, about 6 times or more, about 7 times or more, about 8 times or more, about 9 times or more, about 10 times or more than the value in transformed cell and the like.

As used herein, "transformed corneal endothelial cell marker" refers to a marker, which is expressed in transformed corneal endothelial cell, but significantly less in normal cells. Threshold values of expression in transformed cells include, but are not limited to, about 1.01 times or more, about 1.02 times or more, about 1.03 times or more, about 1.04 times or more, about 1.05 times or more, about 1.1 times or more, about 1.2 times or more, about 1.3 times or more, about 1.4 times or more, about 1.5 times or more, about 1.6 times or more, about 1.7 times or more, about 1.8 times or more, about 1.9 times or more, about 2 times or more, about 2.5 times or more, about 3 times or more, about 3.5 times or more, about 4 times or more, about 4.5 times or more, about 5 times or more, about 6 times or more, about 7 times or more, about 8 times or more, about 9 times or more, about 10 times or more than the value in normal cells.

As used herein, "transform" refers to a characteristic of a cell changing to a non-normal state and includes to mean a normal animal cell undergoing unrestrained cell division, i.e., cancer formation, or especially dynamic metaplasia (dedifferentiation to be a stem cell or changes beyond the realm of basic form of tissue).

Whether a corneal endothelial cell is cultured normally or not can be determined herein by confirming if a corneal endothelial cell maintains at least one characteristic such as its inherent function (also referred to as "normal function" herein, and such a cell is also referred to as a "normal cell"). Examples of such a function include, but not limited to, adaptability to corneal transplantation, ZO-1, Na+/K+-ATPase and the like (Matsubara M, Tanishima T: Wound-healing of the corneal endothelium in the monkey: a morphometric study, Jpn J Ophthalmol 1982, 26: 264-273; Matsubara M, Tanishima T: Wound-healing of corneal endothelium in monkey: an autoradiographic study, Jpn J Ophthalmol 1983, 27: 444-450; Van Horn D L, Hyndiuk R A: Endothelial wound repair in primate cornea, Exp Eye Res 1975, 21: 113-124 and Van Horn D L, Sendele D D, Seideman S, Buco P J: Regenerative capacity of the corneal endothelium in rabbit and cat, Invest Ophthalmol Vis Sci 1977, 16: 597-613). That is, it is understood that the "normal function" may be an indicator indicating a function necessary for realizing corneal transplantation or sufficiency for realizing corneal transplantation. For example, a method of determining normalization can be performed by observing a change in expression using a functional protein in a corneal endothelial cell such as ZO-1 and Na+/K+-ATPase as an indicator, or investigating whether the cell is engrafted and functions by transplantation into a monkey or the like. A determination method by transplantation can be carried out as follows. That is, corneal endothelium is cultured on a carrier such as type I collagen, amnion, corneal stroma or the like to make a cultured corneal endothelium sheet. Under general anesthesia, 1.5 mm incision is made on the limbus corneae of a cynomolgus monkey, a silicon surgical tool is inserted into the anterior chamber, and a corneal endothelial cell is mechanically curetted to make a bullous keratopathy model. Subsequently, a 5 to 6 mm incision is made on the limbus corneae, the cultured corneal endothelium sheet is inserted into the anterior chamber, and the anterior chamber is replaced with air to make the sheet adhere to the corneal endothelium surface. The therapeutic effect of transplantation of the cultured corneal endothelium sheet on bullous keratopathy can be evaluated by cornea transparency with a slit lamp microscope. Further, a therapeutic effect on bullous keratopathy can be similarly evaluated by corneal transparency with a slit-lamp microscope by injecting cells as a suspension with a cell adhesion promotor such as a Rho kinase inhibitor into the anterior chamber without using a carrier. Thus, non-normal, i.e., transformed cells are not assessed as normal cells in this evaluation. Transformed cells have lost or weakened pumping and barrier functions, which are functions of a corneal endothelial cell. Thus, transformed cells are evaluated in categories such as non-transparent cornea, thick cornea, low corneal endothelial cell density and the like.

In the present invention, "Rho kinase" refers to serine/threonine kinase which is activated with activation of Rho. Examples thereof include ROKα (ROCK-II: Leung, T. et al., J. Biol. Chem., 270, 29051-29054, 1995), p160ROCK (ROKβ, ROCK-I: Ishizaki, T. et al., The EMBO J., 15(8), 1885-1893, 1996) and other proteins having serine/threonine kinase activity.

Examples of Rho kinase inhibitors include compounds disclosed in the following documents: U.S. Pat. No. 4,678,783, Japanese Patent No. 3421217, International Publication No. WO 95/28387, International Publication No. WO 99/20620, International Publication No. WO 99/61403, International Publication No. WO 02/076976, International Publication No. WO 02/076977, International Publication No. WO 2002/083175, International Publication No. WO 02/100833, International Publication No. WO 03/059913, International Publication No. WO 03/062227, International Publication No. WO 2004/009555, International Publication No. WO 2004/022541, International Publication No. WO 2004/108724, International Publication No. WO 2005/003101, International Publication No. WO 2005/039564, International Publication No. WO 2005/034866, International Publication No. WO 2005/037197, International Publication No. WO 2005/037198, International Publication No. WO 2005/035501, International Publication No. WO 2005/035503, International Publication No. WO 2005/035506, International Publication No. WO 2005/080394, International Publication No. WO 2005/103050, International Publication No. WO 2006/057270, International Publication No. WO 2007/026664 and the like. Such compounds can be manufactured by the methods described in the respective documents where the compounds are disclosed. The specific examples thereof include 1-(5-isoquinolinesulfonyl)homopiperazine or a salt thereof (e.g., fasudil(1-(5-isoquinolinesulfonyl)homopiperazine)), (+)-trans-4-(1-aminoethyl)-1-(4-pyridylcarbamoyl)cyclohexane((R)-(+)-trans-(4-pyridyl)-4-(1-aminoethyl)-cyclohexanecarboxamide) or a salt thereof (e.g., Y-27632((R)-(+)-trans-(4-pyridyl)-4-(1-aminoethyl)-cyclohexanecarboxamide dehydrochloride monohydrate) and the like) and the like. For these compounds, a commercially available product (Wako Pure Chemical Industries, Ltd, Asahi Kasei Pharma Corporation and the like) can also be preferably used.

Since (+)-trans-4-(1-aminoethyl)-1-(4-pyridylcarbamoyl)cyclohexane, 1-(5-isoquinolinesulfonyl) homopiperazine, pharmaceutically acceptable salts thereof and the like are particularly excellent for promoting adhesion of corneal endothelial cells, they are preferably used. A pharmaceutically acceptable acid addition salt is preferred as a salt of the compounds. Examples of such an acid include hydrochloric acid, hydrobromic acid, sulfuric acid and other inorganic acid, methanesulfonic acid, fumaric acid, maleic acid, mandelic acid, citric acid, tartaric acid, salicylic acid and other organic acids and the like. (+)-trans-4-(1-aminoethyl)-1-(4-pyridylcarbamoyl)cyclohexane((R)-(+)-trans-(4-pyridyl)-4-(1-aminoethyl)-cyclohexanecarboxamide)·dihydrochloride (which may also be monohydrate) and 1-(5-isoquinolinesulfonyl)homopiperazine hydrochloride are more preferable.

As used herein, "specimen" refers to a subject which is to be subjected to diagnosis, detection or the like in the present invention (e.g., an organism such as a human, an organ (eye) or a cell which has been taken out from an organism or the like).

As used herein, a "sample" refers to any substance obtained from a specimen or the like, and includes, for example, a cell of an eye. Those skilled in the art can appropriately select a preferable sample based on the descriptions herein.

As used herein, an "agent" is used in a broad sense, and may be any substance or other elements (e.g., energy such as light, radiation, heat, and electricity) as long as the intended objective can be attained. Examples of such a substance include, but are not limited to, proteins, polypeptides, oligopeptides, peptides, polynucleotides, oligonucleotides, nucleotides, nucleic acids (e.g., including DNA such as cDNA and genomic DNA, and RNA such as mRNA), polysaccharides, oligosaccharides, fats, organic small molecules (e.g., hormones, ligands, information transmitting substances, organic small molecules, molecules synthesized by combinatorial chemistry, small molecules which can be utilized as a medicine (e.g., a low molecular weight ligand) and the like), and composite molecule thereof. Representative examples of an agent specific to a polynucleotide include, but are not limited to, a polynucleotide having complementarity with certain sequence homology (e.g., 70% or more sequence identity) relative to the sequence of the polynucleotide, a polypeptide such as a transcription factor binding to a promoter region. Representative examples of an agent specific to a polypeptide include, but are not limited to, an antibody specifically directed to the polypeptide or a derivative or an analog thereof (e.g., single-stranded antibody), a specific ligand or receptor when the polypeptide is a receptor or a ligand, and a substrate when the polypeptide is an enzyme.

As used herein, a "detection agent" in a broad sense refers to any agent capable of detecting a subject of interest (e.g., normal cells (e.g., normal corneal endothelial cell) or transformed cell (e.g., transformed corneal endothelial cell)).

As used herein, an "agent for diagnosis" in a broad sense refers to any agent with which a condition of interest (e.g., a disease or the like) can be diagnosed.

The detection agent of the present invention may be a complex or a composite molecule in which another substance (e.g., label or the like) is bound to a portion which allows detection (e.g., antibody or the like). As used herein, a "complex" or a "composite molecule" refers to any construct comprising two or more parts. For example, when one of the parts is a polypeptide, the other part may be a polypeptide or another substance (e.g., a sugar, a lipid, a nucleic acid, a different hydrocarbon or the like). As used herein, two or more parts constituting the complex may be bound by a covalent bond or another bond or linkage (e.g., a hydrogen bond, an ionic bond, hydrophobic interaction, or Van der Waals force). When the two or more parts are each a polypeptide, this can also be called a chimeric polypeptide. Thus, as used herein, a "complex" encompasses molecules obtained by connecting a plurality of kinds of molecules such as a polypeptide, a polynucleotide, a lipid, a sugar, and a small molecule.

As used herein, "interaction", when referring to two substances, refers to a force (e.g., intermolecular force (Van der Waals force), a hydrogen bond, hydrophobic interaction or the like) being exerted between a substance and another substance. Generally, the two interacting substances are in an associated or a bound state.

The term "bond" or "linkage" or "binding" as used herein refers to physical interaction or chemical interaction between two substances or between combinations thereof. The bond, the linkage and the binding include an ionic bond, a non-ionic bond, a hydrogen bond, a Van der Waals bond, hydrophobic interaction, and the like. Physical interaction (bond) can be direct or indirect, where indirect bond is formed through or due to the effect of another protein or compound. A direct bond is not formed through or due to the effect of another protein or compound, referring to interaction accompanying substantially no other chemical intermediate. The level of expression of the marker of the present invention or the like can be measured by measuring the bond or interaction.

Thus, as used herein, an "agent" (or a detection agent or the like) which "specifically" interacts with (or binds to) a biological agent such as a polynucleotide or a polypeptide includes an agent whose affinity to the biological agent such as a polynucleotide or a polypeptide is representatively equal to or higher than, preferably significantly (e.g., statistically significantly) higher than the affinity to other irrelevant polynucleotide or polypeptide (particularly, those with less than 30% identity). Such affinity can be measured, for example, by a hybridization assay, a binding assay or the like.

As used herein, a first substance or agent "specifically" interacting with (or binding to) a second substance or agent refers to a first substance or agent interacting with (or binding to) a second substance or agent with higher affinity than that to a substance or agent other than the second substance or agent (particularly another substance or agent that is present in a sample containing the second substance or agent). Examples of interaction (or bond) specific to a substance or an agent include, but are not limited to, a ligand-receptor reaction, hybridization in nucleic acids, an antigen-antibody reaction in proteins, an enzyme-substrate reaction, and when both a nucleic acid and a protein are involved, a reaction between a transcription factor and a binding site of the transcription factor and the like, protein-lipid interaction, nucleic acid-lipid interaction and the like. Thus, when both of the substances or agents are nucleic acids, a first substance or agent "specifically interacting" with a second substance or agent encompasses the first substance or agent having complementarity to at least a part of the second substance or agent. For example, when both of the substances or agents are proteins, examples of "specific" interaction (or bond) of a first substance or agent with a second substance or agent includes, but are not limited to, interaction by an antigen-antibody reaction, interaction by a receptor-ligand reaction, enzyme-substrate interaction. When two kinds of substances or agents include a protein and a nucleic acid, "specific" interaction (or bond) of a first substance or agent with a second substance or agent encompasses interaction (or bond) between a transcription factor and a binding region of a nucleic acid molecule which is a subject of the transcription factor.

As used herein, "detection" or "quantitation" of polynucleotide or polypeptide expression can be attained, for example, by using an appropriate method including mRNA measurement and an immunological measuring method, which includes binding or interaction with a marker detection agent. Examples of a molecular biological measuring method include a Northern blotting method, a dot blotting method, a PCR method and the like. Examples of an immunological measuring method include, as a method, an ELISA method using a microtiter plate, an RIA method, a fluorescent antibody method, a luminescence immunoassay (LIA), an immunoprecipitation method (IP), a single radical immuno-diffusion method (SRID), turbidimetric immuno-assay (TIA), a Western blotting method, and an immuno-histological staining method. Further, examples of a quantitation method include, but are not limited to, an ELISA method and an RIA method. Detection or quantitation can also be performed by a genetic analysis method using an array (e.g., DNA array or protein array). The DNA array is extensively reviewed in (Cell Technology, separate volume, "DNA Microarray and Advanced PCR method", edited by Shujunsha Co., Ltd.). A protein array is described in detail in Nat Genet. 2002 December; 32 Suppl: 526-532. Examples of a method for analyzing gene expression include, but are not limited to, RT-PCR, a RACE method, a SSCP method, an immunoprecipitation method, a two-hybrid system, in vitro translation and the like in addition to the aforementioned methods. Such additional analysis methods are described, for example, in Genome Analysis Experimental Method, Nakamura Yusuke Lab. Manual, edited by Yusuke Nakamura, Yodosha Co., Ltd. (2002) and the like. The entirety descriptions in the document are incorporated herein by reference.

As used herein, an "expression amount" refers to an amount of expression of a polypeptide, mRNA, or the like in a cell, tissue or the like of interest. Examples of such an expression amount include an expression amount at the protein level of the present polypeptide evaluated by any appropriate method including an immunological measuring method such as an immunohistological staining method, an ELISA method, an RIA method, a fluorescent antibody method, and a Western blotting method using the antibody of the present invention, and an expression amount at the mRNA level of a polypeptide used in the present invention which is evaluated by any appropriate method including a molecular biological measuring method such as a PCR method, a Northern blotting method, and a dot blotting method. "Change in an expression amount" refers to an increase or decrease in an expression amount at the protein level or the mRNA level of a polypeptide used in the present invention, which is evaluated by any appropriate method including the immunological measuring method and the molecular biological measuring method described above. By measuring an expression amount of a certain marker, a variety of detections or diagnoses based on the marker can be performed.

As used herein, "decrease", "suppression" or a synonym thereof of the activity, an expression product (e.g., a protein or a transcription product (such as RNA) or the like) refers to a decrease in an amount, quality or the effect of a specific activity, transcription product or protein, or an activity that decreases them.

As used herein, "increase", "activation" or a synonym thereof of the activity or an expression product (e.g., a protein, a transcription product (such as RNA) or the like) refers to an increase in an amount, quality or the effect of a specific activity, transcription product or protein, or an activity that increases them.

Thus, it is understood that an agent which performs differentiation modulation of an ocular cell can be detected or screened using the modulation ability such as decrease, suppression, increase or activation of the marker of the present invention as an indicator.

As used herein, an "antibody" includes, in a broad sense, polyclonal antibodies, monoclonal antibodies, multi-specific antibodies, chimeric antibodies, anti-idiotype antibodies, and fragments thereof, e.g., Fv fragments Fab' fragments, F(ab')$_2$ and Fab fragments, as well as other conjugates or functional equivalents produced by recombination (e.g., chimeric antibodies, humanized antibodies, multifunctional antibodies, bispecific or oligospecific antibodies, single chain antibodies, scFV, diabody, sc(Fv)$_2$(single chain (Fv)$_2$, and scFv-Fc). Furthermore, such an antibody may be covalently bound, or recombinantly fused with an enzyme such as alkaline phosphatase, horseradish peroxidase, or a galactosidase. Antibodies to CD98 or the like used in the present invention is sufficient if they bind to a protein such as CD98, respectively, regardless of the origin, type, shape or the like thereof. Specifically, known antibodies such as a non-human animal antibody (e.g., a mouse antibody, a rat antibody, or a camel antibody), a human antibody, a chimeric antibody, or a humanized antibody can be used. In the present invention, a monoclonal or polyclonal antibody can be utilized as an antibody, but a monoclonal antibody is preferable. It is preferable that an antibody binds specifically to each protein such as CD98.

As used herein, an "antigen" refers to any substrate which can be specifically bound with an antibody molecule. As used herein, an "immunogen" refers to an antigen which can initiate lymphocyte activation that produces an antigen-specific immunological response. As used herein, an "epitope" or an "antigen determinant" refers to a site in an antigen molecule to which an antibody or a lymphocyte receptor binds. A method for determining an epitope is well known in the art. When a primary sequence of a nucleic acid or an amino acid is provided, such an epitope can be determined by those skilled in the art using such a well-known conventional technique.

As used herein, "means" refers to any matter which can serve as a tool for attaining a certain objective (e.g., detection, diagnosis, or treatment). As used herein, "means for selective recognition (detection)" especially refers to means which can recognize (detect) a certain subject differently from others.

It is understood that an antibody of any specificity may be used as an antibody used herein, as long as pseudopositivity is decreased. Thus, an antibody used in the present invention may be a polyclonal antibody or a monoclonal antibody. As used herein, a "ligand" refers to a substance that specifically binds to a certain protein. Examples of ligands include lectin, an antigen, an antibody, a hormone, a neurotransmitter and the like, which specifically bind to a variety of receptor protein molecules on a cell membrane.

The detection agent, the agent for diagnosis or other pharmaceuticals of the present invention can be in a form of a probe and a primer. The probe and the primer of the present invention can specifically hybridize with a molecule such as CD98. As described herein, expression of a molecule such as CD98 is an indicator a normal cell or transformed cell in corneal endothelial cells and is useful as an indicator of the level of transformation. Thus, the probe and the primer according to the present invention can be used for identifying a normal cell or transformed cell among corneal endothelial cells and/or identifying the level of transformation. In one embodiment, the probe and the primer of the present invention is sufficient if they detect expression of a molecule such as CD98, and refer to a polymer consisting of a plurality of bases or base pairs such as deoxyribonucleic acids (DNAs) or ribonucleic acids (RNAs). It is known that a double-stranded cDNA can also be utilized in tissue in situ hybridization. The probe and the primer of the present invention also encompass such a double-stranded cDNA. Examples of the probe and the primer particularly preferable in detection of RNA in a tissue include an RNA probe (riboprobe).

As used herein, a "(nucleic acid) primer" refers to a substance required for initiation of a reaction of a polymer compound to be synthesized in a polymer synthesizing enzyme reaction. In a reaction of synthesizing a nucleic acid molecule, a nucleic acid molecule (e.g., DNA, RNA, or the like) complementary to a part of a sequence of a polymer compound to be synthesized can be used. As used herein, a primer can be used as marker detection means.

Examples of a nucleic acid molecule which is generally used as a primer include molecules having a nucleic acid sequence having a length of at least 8 consecutive nucleotides, which is complementary to a nucleic acid sequence of a gene of interest. Such a nucleic acid sequence can be a nucleic acid sequence with a length of preferably at least 9 consecutive nucleotides, more preferably at least 10 consecutive nucleotides, still more preferably at least 11 consecutive nucleotides, at least 12 consecutive nucleotides, at least 13 consecutive nucleotides, at least 14 consecutive nucleotides, at least 15 consecutive nucleotides, at least 16 consecutive nucleotides, at least 17 consecutive nucleotides, at least 18 consecutive nucleotides, at least 19 consecutive nucleotides, at least 20 consecutive nucleotides, at least 25 consecutive nucleotides, at least 30 consecutive nucleotides, at least 40 consecutive nucleotides, or at least 50 consecutive nucleotides. A nucleic acid sequence used as a probe includes nucleic acid sequences which are at least 70% homologous, more preferably at least 80% homologous, still more preferably at least 90% homologous, or at least 95% homologous to the aforementioned sequences. A sequence appropriate as a primer can vary depending on the nature of a sequence which is intended to be synthesized (amplified). Those skilled in the art can appropriately design a primer depending on the intended sequence. Design of such a primer is well known in the art. Designing may be performed manually or by using a computer program (e.g., LASERGENE, PrimerSelect, or DNAStar).

The primer according to the present invention can also be used as a primer set consisting of two or more of the primers.

The primer and the primer set according to the present invention can be utilized as a primer and a primer set in accordance with a conventional method in a known method for detecting a gene of interest by utilizing a nucleic acid amplification method such as a PCR method, an RT-PCR method, a real time PCR method, an in situ PCR method, a LAMP method or the like.

The primer set according to the present invention can be selected so that a nucleotide sequence of a protein of interest such as a molecule such as CD98 can be amplified by a nucleic acid amplification method such as a PCR method. The nucleic acid amplification method is well known. Selection of a primer pair in the nucleic acid amplification method is obvious to those skilled in the art. For example, primers can be selected in a PCR method so that one of two primers (primer pair) is paired with a plus chain of double-stranded DNA of a protein of interest, e.g., a molecule such as CD98, and the other primer is paired with a minus chain of the double-stranded DNA, and the latter primer is paired with an extended chain which is extended by the former primer. Further, in a LAMP method (WO 00/28082), three regions of F3c, F2c and F1c from the 3' terminal side, and three regions of B1, B2 and B3 from the 5' terminal side are defined, respectively, for a target gene, and these six regions can be used to design four types of primers. The primer of the present invention can be chemically synthesized based on the nucleotide sequences disclosed herein. Preparation of the primer is well known and can be performed in accordance with, for example, "Molecular Cloning, A Laboratory Manual $2^{nd}$ ed." (Cold Spring Harbor Press (1989)) or "Current Protocols in Molecular Biology" (John Wiley & Sons (1987-1997)).

As used herein, a "probe" refers to a substance that can be means for retrieval, used in a biological experiment such as in vitro and/or in vivo screening. Examples thereof include, but are not limited to, a nucleic acid molecule comprising a specific base sequence or a peptide comprising a specific amino acid sequence, a specific antibody or a fragment thereof and the like. As used herein, the probe is used as means for marker detection.

Examples of a nucleic acid molecule which is generally used as a probe include nucleic acid molecules having a nucleic acid sequence with a length of at least 8 consecutive nucleotides, which is homologous or complementary to a nucleic acid sequence of a gene of interest. Such a nucleic acid sequence can be at least a nucleic acid sequence with a length of preferably at least 9 consecutive nucleotides, more preferably at least 10 consecutive nucleotides, still more preferably a at least 11 consecutive nucleotides, at least 12 consecutive nucleotides, at least 13 consecutive nucleotides, at least 14 consecutive nucleotides, at least 15 consecutive nucleotides, at least 20 consecutive nucleotides, at least 25 consecutive nucleotides, at least 30 consecutive nucleotides, at least 40 consecutive nucleotides, or at least 50 consecutive nucleotides. A nucleic acid sequence used as a probe includes nucleic acid sequences which are at least 70% homologous, more preferably at least 80% homologous, still more preferably at least 90% homologous, or at least 95% homologous to the aforementioned sequences.

In one embodiment, the detection agent of the present invention can be a labeled agent. Alternatively, the detection agent of the present invention may be an agent bound to a tag.

As used herein, a "label" refers to an entity (e.g., substance, energy, electromagnetic wave or the like) for distinguishing a molecule or substance of interest from others. Examples of a method of applying such a label include an RI (radioisotope) method, a fluorescence method, a biotin method, a chemiluminescence method and the like. When a plurality of markers of the present invention, or agents or means for capturing them is labeled by a fluorescence method, labeling is performed with fluorescent substances having different fluorescence maximum wavelengths. A difference in the fluorescence maximum wavelength is preferably 10 nm or more. When a ligand is labeled, any label can be used as long as the function is not affected, although Alexa™ Fluor is desirable as a fluorescent substance. Alexa™ Fluor is a water-soluble fluorescent dye obtained by modifying coumarin, rhodamine, fluorescein, cyanine or the like. Alexa™ Fluor is a series compatible with a wide range of fluorescent wavelengths, which is very stable, bright, and low in pH sensitivity as compared with other fluorescent dyes of corresponding wavelengths. Examples of a combination of fluorescent dyes with a fluorescent maximum wavelength of 10 nm or longer include a combination of Alexa™ 555 and Alexa™ 633, a combination of Alexa™ 488 and Alexa™ 555, and the like. When a nucleic acid is labeled, any label can be used as long as it can bind to a base portion thereof. It is preferable that a cyanine dye (e.g., Cy3, Cy5 or the like of CyDye™ series), a rhodamine 6G reagent, N-acetoxy-N2-acetylaminofluorene (AAF), AAIF (iodine derivative of AAF) or the like is used. Examples of fluorescent substances having a difference in fluorescence maximum wavelengths of 10 nm or more include a combination of Cy5 and a rhodamine 6G reagent, a combination of Cy3 and fluorescein, a combination of a rhodamine 6G reagent and fluorescein and the like. In the present invention, such a label can be utilized to modify a subject of interest to be detectable by detection means to be used. Such a modification is known in the art. Those skilled in the art can appropriately carry out such a method in accordance with a label and a subject of interest.

As used herein, a "tag" refers to a substance for selecting and sorting out a molecule by a specific recognition mechanism such as in receptor-ligand binding, more specifically a substance which plays a role of a binding partner for binding to a specific substance (e.g., a substance having a relationship such as biotin-avidin or biotin-streptavidin). Tags can be included in the category of "label". For example, a specific substance with a tag bound thereto can be selected and sorted out by contacting the substance with a substrate with a binding partner of a tag sequence bound thereto. Such a tag or label is well known in the art. Representative tag sequences include, but are not limited to, a myc tag, a His tag, HA, an Avi, and the like. The marker or the marker detection agent of the present invention may be bound to such a tag.

In one aspect, the present invention provides a method for using a molecule such as CD98 as an indicator for identifying a cell with a high proliferation ability among corneal endothelial cells and/or the differentiation ability of a corneal endothelial cell, or a method of detecting or diagnosing a cell with a high proliferation ability among corneal endothelial cells and/or the differentiation ability of a corneal endothelial cell.

The method of the present invention can be implemented by performing, for example, a step of detecting a molecule such as CD98 or genes of these molecules in a living body, for using the molecule such as CD98 as an indicator for identifying a cell with a high proliferation ability among corneal endothelial cells and/or the differentiation ability of a corneal endothelial cell. For example, in such a case, a detection agent comprising a substance that binds to a molecule such as CD98, or genes of these molecules can be used. Such a detection agent is described herein. It is understood that those skilled in the art can implement the method of the present invention based on the description herein.

In the method of the present invention, the detection agent or the diagnostic agent of the present invention is contacted with a sample of interest to determine whether there is a molecule such as CD98 or genes of these molecules that is a sample of interest in the sample or to measure the level or amount thereof.

As used herein, "contact (contacted)" refers to physically proximating a substance to a polypeptide or a polynucleotide which can function as the marker, the detection agent, the agent for diagnosis, the ligand or the like of the present invention, either directly or indirectly. The polypeptide or the polynucleotide can be made to be present in many buffers, salts, solutions or the like. Contact includes placing a compound on, for example, a beaker, a microtiter plate, a cell culturing flask or a microarray (e.g., gene chip), containing a polypeptide encoding a nucleic acid molecule or a fragment thereof.

In one embodiment, a cell with a high proliferation ability which is a subject in the method of the present invention, is an undifferentiated cell.

In another embodiment, a cell with a high proliferation ability, which is a subject in the method of the present invention, is a stem cell.

In another aspect, a corneal endothelial cell, which is a subject in the method of the present invention, is a human cell.

In yet another embodiment, the proliferation ability of a corneal endothelial cell, which is a subject in the method of the present invention, is identified by a characteristic selected from the group consisting of colony forming ability, Ki-67 positivity and BrdU positivity.

In one embodiment of the present invention, the differentiated state can be diagnosed based on the method using an indicator of the present invention.

A specific method of detecting expression of a molecule such as CD98, or genes of these molecules is not particularly limited as long as it is a method which can detect expression of a molecule such as CD98 or genes of these molecules in a test sample (e.g., cell or the like). Examples thereof include a hybridization method, a nucleic acid amplification method, an antigen-antibody reaction method and the like.

Herein, a "test sample" only needs to be a sample that is a corneal endothelial cell, a cell of interest, or a substance derived therefrom, which is considered to contain a matter allowing gene expression. For example, a cell which is directly isolated from the corneal endothelium can be used. A cell of the corneal endothelium can be obtained by a known method (Koizumi N, Okumura N, Kinoshita S., Experimental Eye Research. 2012; 95: 60-7.). Preferably, a cell obtained from a donor of the corneal endothelium, a corneal endothelial cell or the like can be used as a test cell sample. Further, a cultured cell containing a corneal endothelial cell which was differentiated and induced in vitro can be used as a sample. In vitro differentiation induction into a corneal endothelial cell can be implemented by performing differentiation treatment by a known method, for example, an AMED method while using a known cell such as an ES cell, an iPS cell, a bone marrow stromal cell or the like as a starting material <Ueno M, Matsumura M, Watanabe K, Nakamura T, Osakada F, Takahashi M, Kawasaki H, Kinoshita S, Sasai Y; Proc Natl Acad Sci USA. 103 (25): 9554-9559, 2006.>.

According to one embodiment of detection according to the present invention, expression of a molecule such as CD98 or genes of the molecules in a cell sample can be detected by hybridizing the probe according to the present invention with a nucleic acid sample (mRNA or a transcription product thereof) and directly or indirectly detecting a hybridization complex, i.e., a double-stranded nucleotide. The following can be referred to for a detailed procedure of a hybridization method: "Molecular Cloning, A Laboratory Manual $2^{nd}$ ed." (Cold Spring Harbor Press (1989), particularly Section 9.47-9.58), "Current Protocols in Molecular Biology" (John Wiley & Sons (1987-1997), particularly Section 6.3-6.4), and "DNA Cloning 1: Core Techniques, A Practical Approach $2^{nd}$ ed." (Oxford University (1995), see particularly section 2.10 for conditions).

Detection of expression of a molecule such as CD98 or genes of these molecules utilizing a hybridization method can be implemented by, for example, (a) contacting a polynucleotide derived from a test sample with the probe according to the present invention; and (b) detecting a hybridization complex. In the step (a), mRNA prepared from a test sample of interest or complementary DNA (cDNA) transcribed from the mRNA can be contacted with the probe as the polynucleotide derived from a test cell sample. In a method of detection using a probe, the probe can be labeled for use. Examples of the label include labels utilizing radioactivity (e.g., $^{32}$P, $^{14}$C, and $^{35}$S), fluorescence (e.g., FITC and europium), an enzyme reaction such as chemiluminescence (e.g., peroxidase and alkaline phosphatase) or the like. A hybridization product can be detected using a well-known method such as Northern hybridization, Southern hybridization, colony hybridization, or the like. Since a cell from which a hybridization complex was detected is a cell expressing a molecule such as CD98, the cell can be determined to have a high proliferation ability (an undifferentiated cell, a precursor cell, a stem cell or the like) and/or a high differentiation ability.

According to another embodiment of detection according to the present invention, expression of a molecule such as CD98 or genes of these molecules in a sample can be detected by amplifying a nucleic acid sample (mRNA or a transcription product thereof) by a nucleic acid amplification method using the primer or the primer set according to the present invention and detecting the amplification product.

Detection of expression of a molecule such as CD98 or genes of these molecules utilizing a nucleic acid amplification method can be implemented, for example, by (i) implementing a nucleic acid amplification method using the primer or the primer set according to the present invention while using a polynucleotide derived from a test sample as a template; and (ii) detecting the formed amplification product.

In step (i), mRNA prepared from a test sample of interest or complementary DNA (cDNA) transcribed from the mRNA can be used as a template. An amplification product can be detected using a nucleic acid amplification method such as a PCR method, an RT-PCR method, a real time PCR method, or a LAMP method. A cell from which an amplification product is detected is highly likely a normal corneal endothelial cell for a normal corneal endothelial cell marker and highly likely a transformed corneal endothelial cell for a transformed corneal endothelial cell marker. Thus, the cell can be determined to be a normal or transformed cell.

According to another embodiment of detection according to the present invention, whether a contained cell is a normal or transformed cell and/or the ratio thereof in a sample can be determined by contacting the antibody according to the present invention with the sample to detect an antigen-antibody reaction.

Detection of expression of a molecule such as CD98 utilizing an antigen-antibody reaction can be implemented, for example, by the following steps: (I) contacting a protein derived from a test cell sample with the antibody according to the present invention; and (II) measuring an antigen-antibody complex. A method of detecting an antigen-antibody reaction is well known to those skilled in the art. For example, a molecule such as CD98 in a test cell sample which is thought to contain a dopaminergic neuron proliferative progenitor cell can be detected by an immunological method. As the immunological method, a known method such as an immunohistological staining method, an enzyme immunometric assay, a Western blotting method, an agglutination method, a competition method, or a sandwich method can be applied to a sample obtained by subjecting a cell sample to an appropriate treatment as needed such as separation of a cell or an extraction operation. The immunohistological staining method can be performed, for example, by a direct method using a labeled antibody, an indirect method using a labeled antibody to the above antibody, or the like. As a labeling agent, a known labeling substance such as a fluorescent substance, a radioactive substance, an enzyme, a metal, or a dye can be used.

Since a cell from which an antigen-antibody complex is detected is a cell expressing a molecule such as CD98, the cell can be determined to have high proliferation ability (an undifferentiated cell, a precursor cell, a stem cell or the like) and/or high differentiation ability. It is desirable that cells with a high proliferation ability (an undifferentiated cell, a precursor cell, a stem cell, or the like) are of high purity for use in therapy of a disease requiring transplantation of the corneal endothelium such as bullous keratopathy, corneal edema, leukoma corneae, particularly corneal dystrophy, or a corneal endothelial disorder caused by trauma or intraocular surgery, or other specified corneal endothelial diseases (Fuchs endothelial corneal dystrophy, posterior polymorphous corneal endothelial dystrophy etc.).

Instead of performing each of the aforementioned detection steps once, the steps can be repeated or combined to enhance the precision of detection or selection of the level of normal/transformed cells. Thus, when such an embodiment is used, the level of normal/transformed cells can be detected or selected more precisely by performing the aforementioned steps two or more times according to the detection method according to the present invention.

Further, the precision of detection or selection of the level of normal/transformed cells can be enhanced by concurrently using another marker gene, preferably a proliferation marker gene (e.g., Ki-67, BrdU or the like), detection agent thereof or the like.

As used herein, "diagnosis" refers to identification of a variety of parameters associated with a disease, disorder, condition or the like in a subject (e.g., living body, cell or the like) to determine the current or future status of such a disease, a disorder, a condition or the like. By using the method, the apparatus or the system of the present invention, the state in a cell a body, or the like can be examined. Such information can be used to select a variety of parameters such as a disease, a disorder, or a condition in a subject, a formulation or a method for treatment or prevention to be administered. As used herein, in a narrow sense, "diagnosis" refers to diagnosis of the current status, while encompassing "early diagnosis", "presumptive diagnosis", "advance diagnosis" and the like in a broad sense. Since the diagnosis method of the present invention, in principle, can utilize what has come from a body (e.g., cells) and can be implemented without a healthcare professional such as a doctor, it is industrially useful. For example, a cell can be diagnosed by using a substance that binds to a marker of the present invention to identify a normal corneal endothelial cell and a transformed corneal endothelial cell. As used herein, "presumptive diagnosis, advance diagnosis or diagnosis" particularly may be called "assistance" in order to clarify that the method can be implemented without a healthcare professional such as a doctor.

A procedure of formulating an agent for diagnosis or the like of the present invention as a pharmaceutical or the like is known in the art and described, for example, in Japanese Pharmacopoeia, U.S. Pharmacopoeia, and other countries' Pharmacopoeias. Thus, those skilled in the art can determine the amount of the agent for diagnosis to be used from the descriptions herein without undue experiments.

An antibody used in the present invention can be produced as follows.

An antibody used in the present invention (e.g., anti-CD98 antibody or the like) can be obtained as a polyclonal or monoclonal antibody using known means. As an antibody used in the present invention, a monoclonal antibody derived from a mammal is especially preferable. Monoclonal antibodies derived from a mammal include monoclonal antibodies produced by a hybridoma, monoclonal antibodies produced by a host transformed with an expression vector comprising an antibody gene by a genetic engineering procedure and the like.

As one example, a method for preparing a monoclonal antibody is described below. The monoclonal antibody can be prepared by preparing a hybridoma by cell fusion between an antibody producing cell obtained from an animal immunized with an antigen and a myeloma cell, and selecting a clone producing an antibody which specifically inhibits the activity of a molecule such as CD98 from the resulting hybridoma.

The full amino acid sequence of a protein such as a mature protein, such as a molecule such as CD98 used as an antigen in immunization of an animal, or a fragment thereof having immunogenicity, can be used as an immunogen. Further, it is preferable to use a peptide consisting of any 10 or more in an amino acid sequence of a protein of the marker of the present invention as an antigen, as a monoclonal antibody for specifically detecting a protein that is present on a cell surface. An antigen can be designed similarly for any other agent of the present invention (e.g., a molecule such as CD98 as well as proteins corresponding thereto or the like).

After binding to the resulting molecule such as CD98 for an antigen, an adjuvant is added. Examples of the adjuvant include a Freund complete adjuvant, a Freund incomplete adjuvant, and the like. Any of them may be mixed.

The antigen obtained as described above is administered to a mammal such as a mouse, a rat, a horse, a monkey, a rabbit, a goat, or sheep. Any method can be used for immunization as long as it is an existing method, but immunization is mainly performed by intravenous injection, subcutaneous injection, intraperitoneal injection or the like. Further, an immunization interval is not particularly limited. Immunization is performed at an interval of a few days to a few weeks, preferably at an interval of 4 to 21 days.

After 2 to 3 days from the day of last immunization, an antibody producing cell is collected. Examples of the antibody producing cell include a spleen cell, a lymph node cell, and a peripheral blood cell. However, a spleen cell is generally used. As the immunization amount of an antigen, for example, 100 µg of antigen is used once per mouse.

A monoclonal antibody producing hybridoma can be basically produced as follows using a known technique. First, a protein of interest (e.g., a protein such as a molecule such as CD98) is used as a sensitizing antigen, which is immunized according to a common immunization method. An immune cell obtained from an immunized animal is fused with a known parent cell by a common cell fusion method to obtain a hybridoma. Further, by screening a cell producing an antibody of interest from this hybridoma by a common screening method, a hybridoma producing an antibody of interest can be selected.

Specifically, production of the monoclonal antibody is performed, for example, as follows. First, a protein of interest used as a sensitizing antigen for obtaining an antibody can be obtained by expressing a gene of interest (a molecule such as CD98 or the like). A base sequence of the gene of interest and an amino acid sequence of protein is described in other parts herein (e.g., disclosed in SEQ ID NOs: 1-16). That is, after a genetic sequence encoding the gene of interest is inserted into a known expression vector to transform an appropriate host cell, a protein of interest can be purified from the host cell or the culture supernatant by a known method. Further, a purified natural protein can be similarly used. Further, as used in the present invention, a fusion protein obtained by fusing a desired partial polypeptide of a protein of interest with a different polypeptide can also be utilized as an immunogen. In order to produce the fusion protein to be used as an immunogen, for example, an Fc fragment of an antibody, a peptide tag or the like can be utilized. A vector expressing the fusion protein can be produced by fusing genes encoding two or more types of desired polypeptide fragments in frame and inserting the fused gene in an expression vector. A method of producing the fusion protein is described in Molecular Cloning 2nd ed.

(Sambrook, J et al., Molecular Cloning 2nd ed., 9.47-9.58, Cold Spring Harbor Lab. press, 1989).

The protein of interest purified in this manner (e.g., a protein of a molecule such as CD98) can be used as a sensitizing antigen used in immunization of a mammal. A partial peptide of a protein of interest can also be used as a sensitizing antigen. For example, the following peptides can be used as a sensitizing antigen: a peptide obtained by chemical synthesis based on an amino acid sequence of a protein of interest (a molecule such as CD98 or the like); a peptide obtained by incorporating a part of a gene of interest (a molecule such as CD98 or the like) into an expression vector to express the gene; and a peptide obtained by degrading a protein of interest (a molecule such as CD98) with a protease.

The region and size of a protein used as a partial peptide are not limited. An exemplary region can be selected from an amino acid sequence constituting an extracellular domain of a molecule such as CD98. It is preferable that the number of amino acids constituting a peptide used as a sensitizing antigen is at least 3 or more, for example, 5 or more, or 6 or more. More specifically, a peptide of 8 to 50, preferably 10 to 30 residues can be used as a sensitizing antigen.

In one embodiment, examples of the detection kit according to the present invention include a detection kit for detection of an embodiment according to the present invention, specifically, a kit for detecting expression of a molecule such as CD98, comprising at least the probe according to the present invention. This probe may be labeled. This kit for detection detects expression of a molecule such as CD98 by a hybrid forming method. Thus, a detection method of a first embodiment can further comprise a variety of reagents for carrying out the hybrid forming method, for example a substrate compound used in detection of a label, a hybridization buffer, instruction manual, and/or an instrument as desired.

The detection kit of this embodiment according to the present invention may further comprise a probe, a primer, a primer set, or an antibody which can detect expression of a differentiation marker gene (e.g., Ki-67, BrdU or the like) other than a molecule such as CD98, in order to perform highly precise detection. These probe, primer, primer set and antibody may be labeled. This kit for detection further detects expression of a differentiation marker gene other than a molecule such as CD98 by any of a hybrid forming method, a nucleic acid amplification method, and an antigen-antibody reaction method.

In another embodiment, examples of the kit for detection according to the present invention include a detection kit for carrying out detection of another embodiment according to the present invention, specifically, a kit for detecting expression of a molecule such as CD98, comprising at least the primer according to the present invention or the primer set according to the present invention. This kit for detection detects expression of a molecule such as CD98 by a nucleic acid amplification method. Thus, a detection method of a second embodiment may further comprise a variety of reagents for carrying out a nucleic acid amplification method, for example a buffer, an internal standard which indicates that PCR can progress normally, an instruction manual, and/or an instrument as desired.

The detection kit of this embodiment according to the present invention may further comprise a probe, a primer, a primer set, or an antibody which can detect expression of a differentiation marker gene other than a molecule such as CD98 for high precision detection. These probe, primer, primer set, and antibody may be labeled. This kit for detection further detects expression of a differentiation marker other than a molecule such as CD98 by any of a hybrid forming method, a nucleic acid amplification method, and an antigen-antibody reaction method.

In a further embodiment, examples of the detection kit according to the present invention include a detection kit for carrying out detection of the further embodiment according to the present invention, specifically, a kit for detecting a protein of a molecule such as CD98, comprising at least the antibody according to the present invention. This antibody may be labeled. This kit for detection detects expression of a molecule such as CD98 by detecting an antigen-antibody reaction. The detection method of this embodiment may further comprise a variety of reagents for carrying out an antigen-antibody reaction, for example a secondary antibody, a coloring reagent, a buffer, an instruction manual, and/or an instrument used in an ELISA method or the like as desired.

In this embodiment, the detection kit according to the present invention may further comprise a probe, a primer, a primer set, or an antibody which can detect expression of a differentiation marker other than a molecule such as CD98 for highly precise detection. These probe, primer, primer set, and antibody may be labeled. This kit for detection further detects expression of a differentiation marker other than a molecule such as CD98 by any of a hybrid forming method, a nucleic acid amplification method, and an antigen-antibody reaction method.

It can be understood that these kit, composition or system can use a marker in a sample derived from any subject, agents specifically interacting with the marker, or means selectively recognizing the marker as long as the marker of the present invention (e.g., a molecule such as CD98) can be identified. Thus, it is understood that not only an agent or means specifically described herein, but also any equivalent agent or means known in the art can be used.

In one embodiment, the agent used in the present invention is selected from the group consisting of a nucleic acid molecule, a polypeptide, a fat, a glycan, an organic small molecule and a composite molecule thereof, and the agent is preferably a protein or a composite molecule (e.g., a glycoprotein, a lipoprotein, or the like). Preferably, the agent is an antibody (e.g., a polyclonal antibody or a monoclonal antibody). It is preferable that such an agent is labeled, or can be labeled. This is because diagnosis would be facilitated.

In a preferred embodiment of the present invention, means to be used is selected from the group consisting of a mass spectrometry apparatus, a nuclear magnetic resonance measuring apparatus, an X-ray analysis apparatus, SPR, chromatography (e.g., HPLC, thin layer chromatography, or gas chromatography), an immunological means (e.g., Western blotting, EIA (enzyme immunoassay), RIA (radioimmunoassy), or ELISA (enzyme linked immunosorbent assay)), a biochemical means (e.g., pI electrophoresis, Southern blotting, or two-dimensional electrophoresis), an electrophoresis instrument, a chemical analysis instrument, a fluorescent two-dimensional differential electrophoresis method (2DE-DIGE), an isotope-coded affinity tag (ICAT), a tandem affinity purification method (TAP method), a physical means, laser microdissection and a combination thereof.

In a preferable embodiment of the present invention, the system or the kit of the present invention further comprises a standard of a marker. It is preferable that such a standard is used in order to confirm whether means for detecting a marker (an agent specifically interacting with the marker, means selectively recognizing the marker or the like) is functioning normally.

In a preferable embodiment, the present invention can further comprise means for purifying a sample as a subject. Examples of such purification means include chromatography and the like. Since the precision of diagnosis can be enhanced by purification, the purification means can be used, but it is not essential, in a preferred embodiment.

PREFERRED EMBODIMENTS

Preferred embodiments of the present invention are disclosed below. Embodiments provided below are provided for better understanding of the present invention. It is understood that the scope of the present invention should not be limited to the following descriptions. Thus, it is apparent that those skilled in the art can make appropriately modifications within the scope of the present invention while referring to the descriptions herein.

(Normal Cell/Transformed Cell Markers)

In one aspect, the present invention provides a novel marker for identifying a normal cell and a transformed cell in corneal endothelial cells, comprising at least one marker selected from a normal corneal endothelial cell marker and/or transformed corneal endothelial cell marker.

The normal corneal endothelial cell marker provided in the present invention includes CD166, HLA-A2, CD66a, CD66c, CD66d, CD66e, CD98, CD59, CD54, CD340, CD47, EGF-R, CD29, CD74, CD165, CD221, CD49a, SSEA-4, CD130, CD49f, and the like.

Further, the transformed corneal endothelial cell marker provided in the present invention includes CD26, CD9, CD49b, CD49e, CD13, CD99, CD105, CD63, CD58, CD201, CD56, CD44, CD55, CD71, CD73, CD91, HLA-DQ, CD164, CD49d, CD49c, CD90, MICA/B, CD46, CD140b, CD146, CD147, CD81, CD151, CD200, CD10 and the like.

Most of these markers are cell surface markers. Since the markers are cell surface markers, it is understood that they can be readily used in FACS or the like and facilitate cell analysis.

The markers of the present invention may include at least one transformed corneal endothelial cell marker and at least one normal corneal endothelial cell marker. Since both normal cells and transformed cells can be judged with a positive reaction of marker expression by providing (multiple) markers indicating two types of tendencies, analysis is further facilitated.

Higher level of marker expression is more advantageous for use as a marker. This is because normal and transformed cells would be readily identifyable. For humans, the levels of appropriate strong expression as a marker include, but are not limited to, levels exceeding about 1 time, such as at least about 1.1 times or more, at least about 1.2 times or more, at least about 1.3 times or more, at least about 1.4 times or more, at least about 1.5 times or more, at least about 1.6 times or more, at least about 1.7 times or more, at least about 1.8 times or more, at least about 1.9 times or more, at least about 2 times or more, at least about 2.5 times or more, at least about 3 times or more, at least about 4 times or more, and at least about 5 times or more. Further, one or more markers may be used. Please refer to Tables 2-3 for levels of expression. Table 4 shows preferred markers (CD98, CD166, and CD340 for normal cells, and CD9, CD49e, CD44, and CD73 for transformed cells), but the markers are not limited thereto. Further, it is understood that any one of, two, three, four, five, six, or all seven markers described in Table 4 may be combined.

In one preferred embodiment, CD98, CD166, and CD340 are advantageous as normal corneal endothelial cell markers. One, two or three of these markers can be used. Although not wishing to be bound by any theory, since a very significant difference in expression levels were observed between normal and transformed corneal endothelial cells for these markers, utility as markers thereof can be expected.

In another preferred embodiment, CD9, CD49e, CD44 and CD73 are advantageous as transformed corneal endothelial cell markers. One, two, three, or four of these markers can be used. Although not wishing to be bound by any theory, since a very significant difference in expression levels were observed between normal and transformed corneal endothelial cells for these markers, utility as markers thereof can be expected.

In a still more preferable embodiment, the markers of the present invention include at least one molecule selected from the group consisting of CD98, CD166, and CD340 as a normal corneal endothelial cell marker and at least one molecule selected from the group consisting of CD9, CD49e, CD44, and CD73 as a transformed corneal endothelial cell marker.

In a still more preferable embodiment, the markers of the present invention include at least one marker selected from the group consisting of CD166 and CD73. An even more significant difference in expression levels were observed between normal and transformed corneal endothelial cells, utilize as a marker thereof is expected even more.

In another aspect, the present invention provides a nucleic acid of a gene that can be used as a marker of the present invention and/or a protein encoded by the nucleic acid as a marker. In this case, the present invention provides a detection agent for identifying a normal corneal endothelial cell and a transformed corneal endothelial cell, comprising a substance that binds to the marker of the present invention. It is understood that any form described herein can be utilized as the marker of the present invention. Alternatively, the present invention provides an agent for diagnosis for identifying a normal corneal endothelial cell and a transformed corneal endothelial cell, comprising a substance that binds to a marker of the present invention. Further, the present invention provides a method of diagnosis for identifying a normal corneal endothelial cell and a transformed corneal endothelial cell by using a substance that binds to a marker of the present invention. The detection agent or agent for diagnosis of the present invention can use a substance that binds to a marker of the present invention when a target cell is provided to detect or diagnose whether the target cell is normal or transformed based on information related to the state of a binding between the substance and the cell (e.g., the substance can be used as a label to detect a signal or the like associated with the label or a substance binding thereto).

In one specific aspect, the present invention provides a method of detection for identifying a normal corneal endothelial cell and a transformed corneal endothelial cell, comprising: applying a sample that binds to a marker of the present invention to a sample comprising a corneal endothelial cell, and detecting a binding between the substance and the corneal endothelial cell. Alternatively, the present invention provides a method of diagnosing a corneal endothelial cell, comprising: applying a substance that binds to a marker of the present invention to a sample comprising the corneal endothelial cell; and detecting a binding between the substance and the cell, wherein a normal corneal endothelial cell and a transformed corneal endothelial cell are identified by judging the presence of the binding.

In one embodiment, the substance may be an antibody or an antigen binding fragment thereof, nucleic acid primer, probe or the like.

In a certain embodiment, a cell targeted by an agent for diagnosis or a detection agent of the present invention is a cell that is or was present in a living body. Alternatively, a cell targeted by an agent for diagnosis or detection agent of the present invention may be a subcultured cell or the like, which is not or has not been in a living body.

In a certain embodiment, an agent for diagnosis or method of diagnosis of the present invention can be used to diagnose a corneal endothelial disease. For instance, it is possible to diagnose that a corneal endothelial disease associated with a transformed cell or fibroblast has occurred or there is an indication thereof when an agent for diagnosis or a method of diagnosis of the present invention is used to study the state of a cell that is or was present in a living body and a transformed corneal endothelial cell is found, or when, in a certain embodiment, expression of a transformed corneal endothelial cell marker of the present invention is found at a certain level or higher. When studying in a living body, the state of cells can be diagnosed, for example, before surgery, during surgery or the like. Such a certain level can be appropriately determined by those skilled in the art using common general knowledge in the art such as statistics based on the information herein. Corneal endothelial disorders that may be the subject of detection or diagnosis of the present invention include, but are not limited to, primary disorders (diseases targeting endothelial cells such as corneal endothelial dystrophy (cornea guttata, Fuchs corneal endothelial dystrophy, posterior polymorphous corneal dystrophy, iridocorneal endothelial syndrome, and congenital hereditary corneal endothelial dystrophy), viral diseases (cytomegalovirus corneal endotheliitis, herpes simplex virus corneal endotheliitis and the like), exfoliation syndrome, post-corneal transplantation rejection and the like), secondary disorders (inflammation or physical damage involving an external factor such as keratouveitis, interstitial keratitis, post-cataract surgery, post-retina/vitreous body surgery, post-glaucoma surgery (filtration surgery, peripheral iridotomy), glaucoma attack, long-term contact lens usage, corneal trauma, and birth trauma), final symptoms such as bullous keratopathy. Particularly important corneal endothelial diseases include, but are not limited to, diseases involving fibrotic change of corneal endothelial cells including corneal dystrophy such as Fuchs corneal endothelial dystrophy and posterior polymorphous corneal endothelial dystrophy, corneal endothelial disorder due to trauma or intraocular surgery, and bullous keratopathy.

In one embodiment, an agent for diagnosis or method of diagnosis of the present invention determines that a transformed corneal endothelial cell is comprised when at least one transformed corneal endothelial cell marker is expressed. Alternatively, in another embodiment of the present invention, a corneal endothelial cell is diagnosed as having an irreversible degeneration when at least one transformed corneal endothelial cell marker is expressed.

In one embodiment, the present invention may further comprise an agent for staining the above-described binding substance used in the present invention. The binding state can be made more visible by such staining of a binding substance. Any agent known in the art can be used as an agent used in such staining, as long as the agent is capable of staining.

Any method known in the art can be used as the staining technique. For instance, use of an antibody is known in the art for detecting the presence or overexpression of a specific protein. Since a transformed corneal endothelial cell marker is expressed or have significantly increased expression in a transformed corneal endothelial cell in the present invention, an antibody specific to the transformed corneal endothelial cell marker or normal corneal endothelial cell marker of the present invention can be used for the detection of the expression and the detection of transformed state thereby. The aforementioned technique is not limited thereto and includes western blot, dot blot, precipitation, coagulation, ELISA assay, immunohistochemistry, in situ hybridization, flow cytometry in various tissues and body fluids, and various other sandwich assays. Such techniques are well known in the art. For example, see U.S. Pat. No. 5,876,949 (the entirety thereof is incorporated herein by reference). It is necessary to lyse a cell and incubate the cell with an antibody thereof when using the antibody specific to an intracellular epitope of a transformed corneal endothelial cell marker or normal corneal endothelial cell marker of the present invention. The aforementioned technique is performed in a whole cell lysate or a separated transformed corneal endothelial cell or normal corneal endothelial cell for testing by immunoprecipitation. Alternatively as another technique, for example, immunohistological straining requires the entire cell and further requires a cell layer with a specific cell density. The aforementioned test requires an antibody specific to an extracellular epitope of a transformed corneal endothelial cell marker or normal corneal endothelial cell marker of the present invention. Since a transformed corneal endothelial cell marker or a normal corneal endothelial cell marker is a surface antigen, cytolysis is generally considered unnecessary.

Further, an antibody specific to a transformed corneal endothelial cell marker or a normal corneal endothelial cell marker of the present invention can be utilized for detecting or diagnosing the state of a corneal endothelial cell. A processing method therefor such as immunohistological staining or immunofluorescence microscopy is well known in the art. Such a method can be used for visualizing a transformed corneal cell or normal corneal endothelial cell. For example, see U.S. Pat. No. 5,514,554 (the entirety thereof is incorporated herein by reference). For example, expression of a transformed corneal endothelial cell marker or a normal corneal endothelial cell marker of the present invention can be detected by using an antibody that can detect the entire protein of the transformed corneal endothelial cell marker or normal corneal endothelial cell marker of the present invention or a fragment of a protein thereof. Alternatively, other methods of detecting expression of a transformed corneal endothelial cell marker or normal corneal endothelial cell marker of the present invention include detection of DNA or RNA sequence encoding the transformed corneal endothelial cell marker or normal corneal endothelial cell marker of the present invention. Such a technique for detecting a DNA or RNA sequence is well known in the art and any method can be used.

In this case, an antibody specific to a transformed corneal endothelial cell marker or normal corneal endothelial cell marker of the present invention can be labeled by a covalent or non-covalent bond or linkage or binding by numerous known detectable labels such as fluorescent, radioactive, enzymatic substance or the like in order to detect the expression or distribution change of the transformed corneal endothelial cell marker or normal corneal endothelial cell marker of the present invention. Alternatively, a secondary antibody specific to an antibody specific to a transformed corneal endothelial cell marker or normal corneal endothelial cell marker of the present invention can be labeled with any suitable and detectable label known in the art and used to detect an antibody specific to the transformed corneal endothelial cell marker or normal corneal endothelial cell marker of the present invention.

In one embodiment, diagnosis in a living body can be performed as follows. As one example, an antibody specific to a fluorescently labeled transformed corneal endothelial cell marker or normal corneal endothelial cell marker can be administered into the anterior chamber (or into a vessel) and observed in a living body by a fluorescent microscope or the like. However, diagnostic methods in a living body are not limited thereto. Any other form can be used.

In another aspect, the present invention provides a method of using a marker of the present invention as an indicator for identifying a normal corneal endothelial cell and a transformed corneal endothelial cell. It is understood that any form described herein can be utilized as the marker of the present invention.

(Method of Preparing a Corneal Endothelial Cell Sample with Elevated Ratio of Normal Corneal Endothelial Cells/Method of Preparing Purified Corneal Endothelial Cells)

In another aspect, the present invention provides a method of preparing a corneal endothelial cell sample with an elevated ratio of normal corneal endothelial cells, comprising a) providing a sample comprising corneal endothelial cells, and b) elevating the ratio of normal corneal endothelial cells while using the marker of the present invention as an indicator. It is understood that any form described herein, including (Normal cell/transformed cell markers), can be utilized as the marker of the present invention.

In another aspect, the present invention provides a method of preparing purified corneal endothelial cells, wherein the method comprises: inducing corneal endothelial cells from undifferentiated cells; and elevating a ratio of the corneal endothelial cells while using the marker of the present invention as an indicator. It is understood that any form described herein, including (Normal cell/transformed cell markers) can be utilized as the marker of the present invention.

Examples of the purification method include, but are not limited to, a method of fractionating cells expressing a marker of interest in fluorescence activated cell sorter (FACS), magnetic-activated cell sorting (MACS) and the like.

One specific method includes, but is not limited to, the following: reacting a cultured corneal endothelial cell with an antibody to a normal cell or transformed cell marker and then separating and collecting either a normal cell or transformed cell depending on the level of intensity of expression of the normal cell or transformed cell marker of interest by a fluorescence activated cell sorter.

In one embodiment, undifferentiated cells are induced pluripotent stem (iPS) cells or embryonic stem (ES) cells.

In another aspect, the present invention provides a composition comprising a cell prepared by the method of the present invention.

In still another aspect, the present invention provides use of the composition of the present invention for cornea therapy. The subject of cornea therapy may include, but not limited to, corneal endothelial diseases.

(Purity Test)

In another aspect, the present invention provides an agent for determining purity when making a sample comprising corneal endothelial cells, comprising a substance that binds to the marker of the present invention. Alternatively, the present invention provides a method of determining purity when making a sample comprising corneal endothelial cells, comprising applying a substance that binds to the marker of the present invention to a sample comprising a corneal endothelial cell and detecting a binding between the substance and the corneal endothelial cell, wherein a normal corneal endothelial cell and a transformed corneal endothelial cell are identified by determining the presence of the binding. The present invention further provides a method of therapy or prevention using a cell prepared by the method of determining purity of the present invention. In one embodiment, the therapy or prevention is for a cornea. In one embodiment, a subject of the therapy and prevention includes corneal endothelial diseases. It is understood that any technique and embodiment described herein may be applied to the diseases, therapy and prevention.

Further, in another aspect, the present invention provides a method of using the marker of the present invention as an indicator for determining purity when making a sample comprising corneal endothelial cells.

Methods of determining purity include, but are not limited to, measuring expressed antigens by flow cytometry or the like and dividing the result as the ratio of the whole to determine the purity, observation with a fluorescence microscope after immunostaining, magnetic-activated cell sorting (MACS), western blot, PCR and the like.

One specific method includes, but is not limited to the following: reacting a cultured corneal endothelial cell with an antibody to a normal or transformed cell marker and then determining the ratio of normal cells or transformed cells in a cell population by the level of intensity of expression of a normal cell or transformed cell marker of interest by flow cytometry.

It is understood that any form described herein, including (Normal cell/transformed cell markers), can be utilized as the marker of the present invention used in purity determining techniques.

(General Techniques)

Molecular biological methods, biochemical methods, and microbiological methods used herein are well known and commonly used in the art, which are described in, for example, Sambrook J. et al. (1989). Molecular Cloning: A Laboratory Manual, Cold Spring Harbor and the 3rd Ed. (2001) thereof; Ausubel, F. M. (1987). Current Protocols in Molecular Biology, Greene Pub. Associates and Wiley-Interscience; Ausubel, F. M. (1989). Short Protocols in Molecular Biology: A Compendium of Methods from Current Protocols in Molecular Biology, Greene Pub. Associates and Wiley-Interscience; Innis, M. A. (1990). PCR Protocols: A Guide to Methods and Applications, Academic Press; Ausubel, F. M. (1992). Short Protocols in Molecular Biology: A Compendium of Methods from Current Protocols in Molecular Biology, Greene Pub. Associates; Ausubel, F. M. (1995). Short Protocols in Molecular Biology: A Compendium of Methods from Current Protocols in Molecular Biology, Greene Pub. Associates; Innis, M. A. et al. (1995). PCR Strategies, Academic Press; Ausubel, F. M. (1999). Short Protocols in Molecular Biology: A Compendium of Methods from Current Protocols in Molecular Biology, Wiley, and annual updates; Sninsky, J. J. et al. (1999). PCR Applications: Protocols for Functional Genomics, Academic Press, Experimental Medicine, separate volume, "Gene Introduction & Expression Analysis Experimental Method" Yodosha Co., Ltd., 1997 and the like. The relevant portion thereof (can be the entire document) is incorporated herein by reference.

A DNA synthesis technique for producing an artificially synthesized gene and nucleic acid chemistry are described, for example, in Gait, M. J. (1985). Oligonucleotide Synthesis: A Practical Approach, IRL Press; Gait, M. J. (1990). Oligonucleotide Synthesis: A Practical Approach, IRL Press; Eckstein, F. (1991). Oligonucleotides and Analogues: A Practical Approach, IRL Press; Adams, R. L. et al. (1992). The Biochemistry of the Nucleic Acids, Chapman & Hall; Shabarova, Z. et al. (1994). Advanced Organic Chemistry of Nucleic Acids, Weinheim; Blackburn, G. M. et al. (1996). Nucleic Acids in Chemistry and Biology, Oxford University Press; and Hermanson, G. T. (1996). Bioconjugate Techniques, Academic Press, and the like. The relevant portion thereof is incorporated herein by reference.

For example, as used herein, the oligonucleotide of the present invention can also be synthesized by a standard method known in the art, such as by using an automated DNA synthesizer (e.g., a synthesizer commercially available from Biosearch, Applied Biosystems or the like). For example, a phosphorothioate-oligonucleotide can also be synthesized by the method of Stein et al. (1988, Nucl. Acids Res. 16: 3209), and a methyl phosphonate-oligonucleotide can also be prepared by using a control pore glass polymer support (Sarin et al., 1988, Proc. Natl. Acad. Sci. USA 85: 7448-7451).

Reference literatures such as scientific literatures, patents, and patent applications cited herein are incorporated herein by reference to the same extent that the entirety of each document is specifically described.

As described above, the present invention has been illustrated by showing preferable embodiments to facilitate understanding. The present invention is illustrated below based on Examples. The aforementioned illustration and the following Examples are not provided for the purpose of limiting the present invention, but for the sole purpose of exemplification. Thus, the scope of the present invention is not limited to embodiments and Examples specifically described herein and is limited only by the scope of claims.

EXAMPLES

If necessary, animals used in the following Examples were handled in compliance with the standard set forth at Kyoto Prefectural University of Medicine or Doshisha University and the Declaration of Helsinki. Further, animals were fed and handled in accordance with the ARVO Statement for the Use of Animals in Ophthalmic and Vision Research. For reagents, products specifically described in Examples were used. However, equivalent products of other manufacturers (Sigma, Wako Pure Chemical Industries Co., Ltd., Nacalai Tesque, Inc., abcam, Santa Cruz Biotechnology, R & D Systems, Abnova, Assay Pro, Origene, Biobyt, Biorad, Cell Signaling Technology, GE Healthcare, IBL, and the like) can be used as substitutes.

(Experimental Materials and Methods)
(Material)
(Corneal tissue)

All human corneal tissues used in the present experiment were imported from SightLife™ (Northwest Lions Foundation) of American Seattle Eye Bank. All monkey corneal tissues used were corneas of a cynomolgus monkey euthanized for other research purposes (Nissei Bilis Co., Ltd., Ohtsu, Japan, or Keari Co., Ltd., Wakayama, Japan). All corneas were preserved at 4° C. in a preservation medium (Optisol; Chiron Vision Corporation, Irvine, Calif.).

(Cell Culture)

In primary culture of a human corneal endothelial cell, a Descemet's membrane including an endothelial cell layer was peeled off from a corneal tissue, and placed in 2 mg/ml Collagenase A (catalog No.: 70164923; Roche Applied Science, Penzberg, Germany) dissolved in OPTIMEM-I and incubated at 37° C. After 12 hours, the sample was centrifuged at 1000 rpm for 5 minutes to remove the supernatant. A culture medium was then added to a precipitated corneal endothelial cell mass for admixing. The entire amount was seeded on a 12-well plate coated with FNC Coating Mix (catalog No.: 0407; Athena Enzyme Systems, Baltimore, Md., USA). As a culture medium, OPTIMEM-I (catalog No.: 51985; Gibco-Invitrogen, Carlsbad, Calif.), to which 8% fetal bovine serum (catalog No.: 10437-028; fetal bovine serum; FBS; BioWest, France), 50 μg/ml Gentamicin (Invitrogen), and 10 μg/ml Y-27632 (Calbiochem, La Jolla, Calif.) were added, was used.

In primary culture of a monkey corneal endothelial cell, a Descemet's membrane including an endothelial cell layer was peeled off from a corneal tissue, and placed in 2 mg/ml Collagenase A (catalog No.: 70164923; Roche Applied Science, Penzberg, Germany) dissolved in DMEM (Gibco-Invitrogen) and incubated at 37° C. After 12 hours, the sample was centrifuged at 1000 rpm for 5 minutes to remove the supernatant. A culture medium was then added to a precipitated corneal endothelial cell mass for admixing. The entire amount was seeded on a 12-well plate coated with FNC Coating Mix (catalog No.: 0407; Athena Enzyme Systems, Baltimore, Md., USA). As a culture medium, DMEM (catalog No.: 12320; Gibco-Invitrogen), to which 10% FBS, 50 μg/ml Gentamicin (catalog number: 15710-064; Invitrogen), and 2 ng/ml basic fibroblast growth factor (catalog No.: 13256-029; bFGF; Invitrogen) were added, was used.

As a human cornea, a cornea with the period before primary culture of less than 14 days was used. A previously reported system [Koizumi N et al., Exp Eye Res., 2012; 95: 60-67; Koizumi N et al., Invest Ophthalmol Vis Sci. 2007; 48: 4519-4526; Okumura N et al., Am J Pathol. 2012; 181: 268-277] was used for culture of human and monkey corneal endothelial cells (CEC).

A medium was exchanged every 2 days. Subculture was performed when reaching 50 to 80% confluence. As a subculture method, cells were washed with $Ca^{2+}Mg^{2+}$-free PBS (PBS-; Nissui Pharmaceutical Co., Ltd., Tokyo, Japan), and TrypLE™ Select (catalog No.: 12563; Invitrogen) was added and incubated at 37° C. for 5 minutes. Cells were peeled off and recovered from the plate. After the cells were centrifuged at 1000 rpm for 5 minutes, a culture medium was added to make a cell suspension. Cells were seeded on a plate coated with FNC Coating Mix at a density of 1:2-3.

(Immunostaining)

After immobilizing the culture cells, immunostaining was performed on cells by using CD73, CD166, or, as a functionally related marker, ZO-1, $Na^+/K^+$-ATPase for observation with a fluorescent microscope. Cultured monkey or human corneal endothelial cells were cultured in a 24 well plate (Sigma-Aldrich Co., St. Louis, Mo.) and immobilized for 10 minutes with 4% formaldehyde at room temperature (RT). The cells were incubated for 30 minutes with 1% bovine serum albumin (BSA). Immunohistological staining was then performed with Anti-Human CD73 (catalog number: 550256; BD Pharmingen) or Anti-Human CD166 (catalog number: 559260; BD Pharmingen), or a barrier function associated protein ZO-1 (Zymed Laboratories, Inc., South San Francisco, Calif.) or a pumping function associated protein Na+/K+-ATPase (Upstate Biotec, Inc., Lake Placid, N.Y.). 1:300 dilution of each antibody was used in immunohistological staining. 1:1000 dilution of Alexa Fluor® 488 labeling Alexa Fluor® was used for secondary antibodies. Cellular nuclei were then stained with DAPI (Vector Laboratories, Inc., Burlingame, Calif.). Slides were then observed with a fluorescent microscope (BZ-9000, KEYENCE, Osaka, Japan).

(RT-PCR)

PCR was performed with respect to CD166, CD73, and GAPDH by RT-PCR (Semi-quantitative reverse transcription polymerase chain reaction). A primer was purchased from oligonucleotide synthesizing firm, INVITROGEN and desalinated for use. RNEasy Mini Kit (QIAGEN, catalog number: 74106) was used for extraction of total RNA from cells. Reverse transcription reaction (42° C., 60 minutes) was performed on the extracted RNA with ReverTra Ace (TOYOBO (catalog number: TRT-101)), and CD166 and CD73 were amplified with TAKARA Taq Hot Strat Version (Takara Bio, catalog number: RR001A) with GAPDH as the internal standard. The same amount of cDNA was amplified by a PCR system (GeneAmp 9700; Applied Biosystems) and the following primer pairs.

```
*CD166-F:
                                    (SEQ ID NO: 17)
CCCCAGAGGAATTTTTGTTTTAC

*CD166-R:
                                    (SEQ ID NO: 18)
AGCCTGATGTTATCTTTCATCCA

*CD73-F:
                                    (SEQ ID NO: 19)
GTTCCTGTAGTCCAGGCCTATG

*CD73-R:
                                    (SEQ ID NO: 20)
ACATTTCATCCGTGTGTCTCAG

*GAPDH-F:
                                    (SEQ ID NO: 21)
GAGTCAACGGATTTGGTCGT

*GAPDH-R:
                                    (SEQ ID NO: 22)
TTGATTTTGGAGGGATCTCG
```

An amplified DNA fragment was detected by electrophoresis with 1.5% agarose gel (Nacalai Tesque, catalog number: 01149-76) and staining with ethidium bromide (Nacalai Tesque, catalog number: 14603-51).

(Flow Cytometry)

Cultured human corneal endothelial or cultured monkey corneal endothelial cells were seeded on a culture dish coated with FNC Coating Mix and cultured for about 14 days until reaching confluence under conditions of 5% $CO_2$ at 37° C. Cells were peeled off with TrypLE™ Select and collected. Human Cell Surface Marker Screening Panel (BD Lyoplate™, BD Bio-sciences, Franklin Lakes, N.J.) was used. A flow cytometer (BD FACSCanto™ II (BD Biosciences, Franklin Lakes, N.J.) was used in accordance with the manual to perform high-throughput surface antigen analysis. Further, cultured monkey corneal endothelium (BD Accuri™ C6 (BD Biosciences, Franklin Lakes, N.J.)) was used to analyze surface antigens. 70% ethanol was added to cells peeled off and collected with TrypLE™ Select, and the cells were incubated for 2 hours at −20° C. to immobilize the cells. After washing the cells twice with PBS, 1% BSA was added. The cells were incubated for 15 minutes at room temperature for blocking. APCMouse anti-Human CD73 (catalog number: 560847; BD Pharmingen) or PEMouse anti-Human CD166 (catalog number: 560903; BD Pharmingen) were used and the cells were incubated for 30 minutes at room temperature. Cultured monkey corneal endothelium and immortalized human corneal endothelial cells were sorted by using FACS Aria II (BD Bio-sciences, Franklin Lakes, N.J.). Collected cells were incubated at room temperature for 15 minutes with Purified Mouse anti-Human CD73 (catalog number: 550256; BD Pharmingen) as a primary antibody. Alexa Fluor 488-conjugated goat anti-rabbit IgG (1:1500) was used and incubated for 20 minutes at room temperature as a secondary antibody. The cells were sorted by the level of expression of CD73 and cultured in a 24-well plate (Sigma-Aldrich Co., St. Louis, Mo.).

Reference Example 1

As shown in FIG. 1, the state of the cells when human corneal endothelial cells are separated from a donor cornea and cultured was observed in order to study the issues in conventional cultured corneal endothelial cell production. The experimental observation conditions are as described in the above-described section of (Experimental materials and methods).

As shown in FIG. 1, the left side shows corneal endothelium that could be cultured while maintaining a normal polygonal cellular form. However, when separated and cultured by a common method, the cells readily transform and change into a fibroblast-like form to lose cellular function as shown in the bottom right.

Production of corneal endothelial cells free of transformed cells is essential for clinical applications of cultured corneal endothelial cell transplantation. The current state of ophthalmic science is such that production thereof cannot be achieved with conventional techniques. In this regard, a normal or transformed corneal endothelial cell marker was selected, which can be used for objectives such as determination of purity of cultured cells, enhancement of purity by sorting, sorting and selection of a normal corneal endothelial cell when inducing a corneal endothelial cell from iPS cells and ES cells.

Preparation Example

Production of Immortalized Strain of Normal Corneal Endothelial Cells and Transformed Corneal Endothelial Cells In the present example, immortalized strains of normal corneal endothelial cells and transformed corneal endothelial cells were produced.

(Culture Method)

Corneal endothelial cells were mechanically peeled off with a basal membrane from a corneal for research purchased from the Seattle Eye Bank. After collagenase was used to detach and collect the corneal endothelial cell from the basal membrane, the cells were subjected to primary culture. As a medium for human cells, Opti-MEM I Reduced-Serum Medium, Liquid (INVITROGEN catalog No.: 31985-070) to which 8% fetal bovine serum (FBS) (BIOWEST, catalog No.: S1820-500), 200 mg/ml $CaCl_2.2H_2O$ (SIGMA catalog No.: C7902-500G), 0.08% chondroitin sulfate (SIGMA catalog No.: C9819-5G), 20 µg/ml ascorbic acid (SIGMA catalog No.: A4544-25G), 50 µg/ml gentamicin (INVITROGEN catalog No.: 15710-064) and 5 ng/ml EGF (INVITROGEN catalog No.: PHG0311) were added and acclimated for a 3T3 feeder cell were used. Further, the cells were cultured in a basal medium to which SB431524 (4-[4-(1,3-benzodioxole-5-yl)-5-(2-pyridinyl)-1H-imidazole-2-yl]benzamide) (1 µmol/l) and SB203580 (4-(4-fluorophenyl)-2-(4-methylsulfonylphenyl)-5(4-pyridyl)imdazole<4-[4-(4-fluorphenyl)-2-(4-methylsulfinylphenyl)-1H-imidazole-5-yl]pyridine) (1 µmol/l) were added (referred to as "SB203580+SB431542+3T3 acclimated medium"). SB431542 was obtained from TOCRIS (catalog number: 1614). SB203580 was obtained from CALBIOCHEM (catalog number: 559389).

(Method of Acquisition)

Immortalized cell lines were prepared by introducing an SV40 large T antigen and hTERT gene into each of normal form cells and transformed cells among cultured corneal endothelial cells from a human donor cornea shown in FIG. 1. Specifically, SV40 large T antigen and hTERT gene were amplified by PCR and introduced into a lentiviral vector (pLenti6.3_V5-TOPO; Life Technologies Inc). The lentiviral vector was then used to infect 293T cells (RCB2202; Riken Bioresource Center, Ibaraki, Japan) by a transfection reagent (Fugene HD; Promega Corp., Madison, Wis.), together with three types of helper plasmids (pLP1, pLP2, pLP/VSVG; Life Technologies Inc.). Culture supernatant comprising viruses was collected after 48 hours from the infection. 5 µg/ml polybrene was used and added to culture solutions of each of cultured normal form corneal endothelial cells and transformed corneal endothelial cells. SV40 large T antigen and hTERT gene were introduce to immortalize the cells.

Example 1

Flow Cytometry in Transformed Corneal Endothelial Cell and Normal Corneal Endothelial Cell The inventors screened surface markers of normal human corneal endothelial cells and transformed cells by high-throughput analysis using flow cytometry to proceed with selection of candidate markers.

Human corneal endothelial cells were cultured by the method described above in (Experimental materials and methods). Cells with normal cellular form and transformed cells were subjected to high-throughput analysis by flow cytometry using Human Cell Surface Marker Screening Panel (BD Lyoplate™, BD Bioscience). Expression of surface antigens in each of normal cells and transformed cells was compared, and markers with enhanced expression in normal cells were used as marker candidates for normal cells (Table 2). Meanwhile, markers with enhanced expression in transformed cells were similarly used as markers of transformed cells (Table 3).

(Table 2 Surface Antigens with Enhanced Expression in Normal and Transformed Human Corneal Endothelial Cells)

TABLE 2

| | Human corneal endothelial cell (normal/transformed) | Monkey corneal endothelial cell (normal/transformed) |
|---|---|---|
| CD166 | 10.09 | 11.80 |
| HLA-A2 | 6.23 | 0.97 |
| CD66 (a, c, d, e) | 3.42 | 0.85 |
| CD98 | 3.22 | 2.94 |
| CD59 | 2.97 | 0.90 |
| CD54 | 2.95 | 0.90 |
| CD340 | 2.82 | 2.31 |
| CD47 | 1.88 | 0.48 |
| EGF-R | 1.74 | 6.58 |
| CD29 | 1.46 | 0.26 |
| CD74 | 1.43 | 2.31 |
| CD165 | 1.26 | 16.13 |
| CD221 | 1.19 | 1.87 |

TABLE 2-continued

| | Human corneal endothelial cell (normal/transformed) | Monkey corneal endothelial cell (normal/transformed) |
|---|---|---|
| CD49a | 1.13 | 3.69 |
| SSEA-4 | 1.03 | 0.30 |
| CD130 | 1.02 | 2.26 |
| CD49f | 1.02 | 2.05 |

(Table 3 Surface Antigens with Enhanced Expression in Transformed Human Corneal Endothelial Cells)

TABLE 3

| | Human corneal endothelial cell (transformed/normal) | Monkey corneal endothelial cell (transformed/normal) |
|---|---|---|
| CD26 | 17.96 | 1.05 |
| CD9 | 10.93 | 3.85 |
| CD49b | 8.91 | 0.82 |
| CD49e | 8.85 | 2.38 |
| CD13 | 8.44 | 1.29 |
| CD99 | 5.63 | 1.05 |
| CD105 | 4.60 | 0.99 |
| CD63 | 4.55 | 1.81 |
| CD58 | 4.06 | 0.25 |
| CD201 | 3.65 | 1.06 |
| CD56 | 3.45 | 0.06 |
| CD44 | 3.25 | 2.98 |
| CD55 | 3.01 | 1.15 |
| CD71 | 2.98 | 1.19 |
| CD73 | 2.94 | 2.02 |
| CD91 | 2.73 | 0.18 |
| HLA-DQ | 2.50 | 1.33 |
| CD164 | 2.47 | 0.83 |
| CD49d | 2.46 | 1.38 |
| CD49c | 2.42 | 0.07 |
| CD90 | 2.38 | 0.49 |
| MICA/B | 2.24 | 1.07 |
| CD46 | 2.15 | 1.21 |
| CD140b | 2.05 | 1.49 |
| CD146 | 1.90 | 0.02 |
| CD147 | 1.79 | 0.09 |
| CD81 | 1.73 | 0.37 |
| CD151 | 1.72 | 0.36 |
| CD200 | 1.49 | 0.18 |
| CD10 | 1.24 | 7.27 |

Further, analysis similar to that for human corneal endothelial cells was performed for normal and transformed corneal endothelial cells separated from cynomolgus monkey. Candidate markers in human corneal endothelial cells exhibiting similar tendency in monkey corneal endothelial cells are shown in Table 4 as candidate markers with particularly high accuracy. The protocol used was in accordance with the method described above in (Experimental materials and methods).

(Table 4 Representative Surface Antigen Markers of Corneal Endothelial Cells)

TABLE 4

| Normal | Transformed |
|---|---|
| CD98 | CD9 |
| CD166 | CD49e |
| CD340 | CD44 |
| | CD73 |

As a result thereof, the following normal corneal endothelial cell markers and transformed corneal endothelial cell markers were identified. The markers are shown below.

Markers in normal cells of human corneal endothelial cells are CD166, HLA-A2, CD66 (a, c, d, and e), CD98, CD59, CD54, CD340, CD47, EGF-R, CD29, CD74, CD165, CD221, CD49a, SSEA-4, CD130, and CD49f.

Further, markers in transformed cells are CD26, CD9, CD49b, CD49e, CD13, CD99, CD105, CD63, CD58, CD201, CD56, CD44, CD55, CD71, CD73, CD91, HLA-DQ, CD164, CD49d, CD49c, CD90, MICA/B, CD46, CD140b, CD146, CD147, CD81, CD151, CD200, and CD10.

Markers with especially high accuracy are CD98, CD166, and CD340 for normal cells and CD9, CD49e, CD44, and CD73 for transformed cells.

The inventors selected CD166 and CD73 among the above markers to proceed with further analysis. It is demonstrated that CD166 is highly expressed and CD73 is lowly expressed in normal cells, while CD166 is lowly expressed and CD73 is highly expressed in transformed cells.

These surface antigen markers are explained. CD166 is a type I transmembrane protein broadly distributed in cell populations, which are associated with growth and migration. CD166 is expressed in various cells such as hemopoietic cells, endothelial cells, bone marrow mesenchymal stem cells, fibroblasts and the like. CD73 is a membrane-binding enzyme having action to convert AMP to adenosine under a neutral condition, which is expressed in T and B lymphocyte subsets, follicular dendritic cells, endothelial cells, bone marrow stroma cells and the like.

Example 2

Analysis in Cultured Monkey Corneal Endothelial Cells

In the present Example, cultured monkey corneal endothelial cells were used to analyze cell surface markers thereof in transformed cells and normal cells.

Monkey corneal endothelial cells were cultured. Specifically, a Descemet's membrane including an endothelial cell layer was peeled off from a monkey corneal tissue, and placed in 2 mg/ml Collagenase A (catalog No.: 70164923; Roche Applied Science, Penzberg, Germany) dissolved in DMEM (Gibco-Invitrogen) and incubated at 37° C. After 12 hours, the sample was centrifuged at 1000 rpm for 5 minutes to remove the supernatant. A culture medium was added to a precipitated corneal endothelial cell mass for admixing, and the entire amount was seeded on a 12-well plate coated with FNC Coating Mix (catalog No.: 0407; Athena Enzyme Systems, Baltimore, Md., USA). As a culture medium, DMEM (catalog No.: 12320; Gibco-Invitrogen), to which 10% FBS, 50 μg/ml Gentamicin (catalog number: 15710-064; Invitrogen), and 2 ng/ml basic fibroblast growth factor (catalog No.: 13256-029; bFGF; Invitrogen) were added, was used. Corneal endothelial cells that were able to be cultured in a normal form when cultured with the same method were used as normal corneal endothelial cells and cells undergoing transformation into a fibroblast-like form when cultured with the same method were used as transformed cells in the following study. The normal corneal endothelial cells shown on the left side in the image from a phase difference microscope in FIG. 2 are shown to have a small size for each cell and consist of polygonal, mainly hexagonal, cells. In contrast, cells that have undergone transformation into fibroblast-like form shown on the right side have a large size for each cell and have an elongated shape.

Flow cytometry of CD166 and CD73 in cultured monkey corneal endothelial cells in these two states (normal corneal endothelial cells, transformed cells) was performed. Immunostaining protocol was in accordance with the protocol described in (Experimental Materials and Methods).

The results are shown in FIG. 3. The left side shows normal corneal endothelial cells and the right side shows transformed cells. The top row shows results from flow cytometry using CD166, while the bottom row shows results using CD73. In view of the results, CD166 is highly expressed in normal corneal endothelial cells compared to the control, while the amount of expression was similar to that for the control in transformed cells. Further, expression of CD73 was found to be strongly enhanced in transformed cells than in normal cells in comparison with the control. This demonstrates that CD166 is highly expressed in normal corneal endothelial cells and CD73 is highly expressed in transformed cells. The result is consistent with results from screening analysis using flow cytometry.

Subsequently, RT-PCR was performed for CD166 and CD73 in cultured monkey corneal endothelial cells in these two states (normal corneal endothelial cells, cells that have undergone transformation into fibroblast-like form). The protocol was in accordance with the protocol described in (Experimental materials and methods).

The results are shown in FIG. 4. The bands are for, from the top, CD166, CD73, and GAPDH as a control. The left column is for normal cells and the right column is for transformed cells. It was clearly confirmed from the results that CD166 is highly expressed in normal cells and CD73 is highly expressed in transformed cells also at gene level. This is consistent with the results from screening analysis by flow cytometry.

Subsequently, expression of CD166 and CD73 in cultured monkey corneal endothelial cells in these two states (normal corneal endothelial cells and transformed cells) was also studied with immunostaining. The protocol was in accordance with the protocol described in (Experimental materials and methods).

The results are shown in FIG. 5. The results are shown, from the left side, for CD166 and CD73. The top row shows normal cells and the bottom row shows transformed cells. The results show that CD166 is highly expressed and CD73 is lowly expressed in normal cells, while, CD166 is lowly expressed and CD73 is highly expressed in transformed cells. It was possible to confirm that the results are consistent with the results of screening analysis from flow cytometry. When detailed studied were conducted with CD166 and CD73 as representative normal cell marker and a transformed cell marker, respectively, in view of the above results, they were demonstrated to be usable as a marker in flow cytometry, PCR, and immunostaining.

Example 3

Analysis in Cultured Monkey Corneal Endothelial Cells

The present Example sorted normal and transformed monkey cells with CD73 as an illustration and demonstrated that it is applicable to cell purification. The top left portion of FIG. 6 shows an image of normal monkey corneal endothelial cells and the top right shows an image of transformed cells from a phase difference microscope. After mixing monkey corneal endothelial cells in these two states (normal corneal endothelial cells and transformed cells) at a ratio of 1:1, flow cytometry analysis was performed with CD73. Cells were sorted and cultured in two separate groups, high expression cell group and low expression cell group of CD73. The bottom left is a picture from a phase difference microscope after sorting of CD73 low expression cells (CD73(−)) and the bottom right is of CD73 high expression cells (CD73(+)). CD73(−) is a cell with a polygonal form which the form of normal cells, while CD73(+) is a cell with a transformed fibroblast-like form. This demonstrates that CD73 can be used as a marker for sorting normal cells and transformed fibroblast-like cells.

Example 4

Analysis in Immortalized Human Corneal Endothelial Cells

The present Example used immortalized human corneal endothelial cells prepared in the Preparation Example to analyze cell surface markers in transformed cells and normal cells.

A Descemet's membrane including an endothelial cell layer was peeled off from a human corneal tissue, and placed in 2 mg/ml Collagenase A (catalog No.: 70164923; Roche Applied Science, Penzberg, Germany) dissolved in OPTIMEM-I and incubated at 37° C. After 12 hours, the sample was centrifuged at 1000 rpm for 5 minutes to remove the supernatant. A culture medium was then added to a precipitated corneal endothelial cell mass for admixing, and the entire amount was seeded on a 12-well plate coated with FNC Coating Mix (catalog No.: 0407; Athena Enzyme Systems, Baltimore, Md., USA). Cultured human corneal endothelial cells were introduced with SV40 and hTERT gene to produce immortalized cells. Each of normal cell forms and fibroblast-like transformed cells was cloned from the produced immortalized human corneal endothelial cells and the clones were used in the following study as normal cells and transformed cells.

FIG. 7 shows images of immortalized human corneal endothelial cells from a phase difference microscope. The left side shows normal corneal endothelial cells and the right side shows transformed cells. As in cultured monkey cells, normal corneal endothelial cells shown on the left side are shown to have a small size for each cell and consist of polygonal, mainly hexagonal, cells. In contrast, cells that have undergone transformation into fibroblast-like form shown on the right side have a large size for each cell and have an elongated shape.

With CD73 as an example, a test was carried out to see whether a marker in the present invention can be used to sort and purify normal cells. Mixed culture cells consisting of normal form and transformed immortalized human corneal endothelial cells were analyzed by flow cytometry with CD73.

The results are shown in FIG. 8. It can be understood from flow cytometry with CD73 that the cells consist of two groups, high expression cell group and low expression cell group of CD73. Subsequently, CD73 low expression cells indicated by P4 and CD73 high expression cells indicated by P5 in FIG. 8 were sorted and cultured.

The results are shown in FIG. 9. The left side is a picture from a phase difference microscope after sorting of CD73 low expression cells (CD73(−)) and the middle portion is for CD73 high expression cells (CD73(+)). CD73(−) is a cell with a polygonal form which is the form of normal cells, while CD73(+) is a transformed cell with a fibroblast-like form. The right side is an image from a phase difference microscope of cells cultured without sorting as a control, where cells with a normal form and transformed cells co-exist. In view of the above, it is demonstrated that CD73 can be used as a marker for sorting normal cells and transformed fibroblast-like cells.

Expression was subsequently analyzed for a candidate marker after sorting with CD73. In this analysis, expression of CD73 and CD166 was analyzed. The protocol was in accordance with the protocol described in (Experimental materials and methods).

The results are shown in FIG. 10. The top row shows cells sorted as CD73(−) and the bottom row shows cells sorted as CD73(+). The left side shows staining by CD73 and the right side shows staining with CD166. CD73 was not stained in CD73(−), but CD166 was intensely stained. Further, CD73 was stained in CD73(+), while expression of CD166 was found to be attenuated therein in comparison to CD73(−).

Expression was subsequently analyzed for a function associated marker after sorting with CD73. In this analysis, expression of ZO-1 and $Na^+/K^+$-ATPase was analyzed. The protocol was in accordance with the protocol described in (Experimental materials and methods).

The results are shown in FIG. 11. The top row shows CD73(−) and the bottom row shows CD73(+). The left side shows expression of ZO-1 and the right side shows expression of $Na^+/K^+$-ATPase. It is shown that both ZO-1 and $Na^+/K^+$-ATPase indicating normal function are expressed significantly more in CD73(−). Thus, it is demonstrated that CD73(−) is a marker that can also distinguish normal cells from transformed cells with respect to functional aspects.

Example 5

Method of Preparing Sample with Concentrated Normal Cells Using a Marker of the Present Invention Cultured corneal endothelial cells can be sorted by using a marker for a transformed cell of the present invention to remove transformed cells for purified corneal endothelial cells with a normal form and normal function. Further, corneal endothelial cells with a normal form and normal function can be selectively cultured by sorting cells with a normal cell marker of the present invention. Further, when a sample is contaminated with cells other than corneal endothelial cells such as corneal epithelial cells, corneal stromal cells, conjunctival epithelial cells, or conjunctival stromal cells when culturing corneal endothelial cells from a corneal tissue, the corneal endothelial cells can be purified by sorting with a marker of the present invention. Further, by using this technique, corneal endothelial cells can be purified by sorting with a marker of the present invention from a cell group induced from iPS cells or ES cells.

Example 6

Therapy Using Sample with Concentrated Normal Cells Using a Marker of the Present Invention Therapy can be administered by transplanting cultured corneal endothelial cells or corneal endothelial cells induced from iPS cells or ES cells with enhanced purity produced in Example 5 as a corneal endothelial cell sheet using or without using a carrier into a corneal endothelial dysfunction patient. Further, therapy can be administered by infusion or injection of the cells into the eye, such as within the anterior chamber, as a cell suspension.

As described above, the present invention has been exemplified using preferable embodiments of the present invention. However, it is understood that the scope of the present invention should be construed only by the scope of claims. The present application claims priority to Japanese Patent Application No. 2013-157597, whose entire content is incorporated herein by reference. It is understood that patents, patent applications and literatures cited herein are incorporated herein by reference, as if the contents thereof are specifically described herein.

INDUSTRIAL APPLICABILITY

A marker for distinguishing normal cells from fibroblast-like transformed cells for ocular cells is provided. In addition, a technique available in industries involved in techniques associated with corneal transplantation (cell culture industry, pharmaceuticals or the like) is provided.

[Sequence Listing Free Text]

SEQ ID NO: 1: Nucleic acid sequence of heavy subunit protein of CD98 (Gene ID (Entrez): 6520; NM_001013251 (NM_001012661) and NP_001012680)

SEQ ID NO: 2: Amino acid sequence of heavy subunit protein of CD98 (Gene ID (Entrez): 6520; NM_001013251 (NM_001012661) and NP_001012680)

SEQ ID NO: 3: Nucleic acid sequence of light subunit protein of CD98 (Gene ID (Entrez): 8140 NM_003486; NP_003477)

SEQ ID NO: 4: Amino acid sequence of light subunit protein of CD98 (Gene ID (Entrez): 8140 NM_003486; NP_003477)

SEQ ID NO: 5: Nucleic acid sequence of CD166 (Gene ID (Entrez): 214 (human), NM_001243280 (mRNA), NP_001230209 (protein))

SEQ ID NO: 6: Amino acid sequence of CD166 (Gene ID (Entrez): 214 (human), NM_001243280 (mRNA), NP_001230209 (protein))

SEQ ID NO: 7: Nucleic acid sequence of CD340 (Entrez Gene ID: (Hu) 2064, and NM_0010005862.1)

SEQ ID NO: 8: Amino acid sequence of CD340 (Entrez Gene ID: (Hu) 2064, NM_0010005862.1)

[Sequence Listing Free Text]

SEQ ID NO: 9: Nucleic acid sequence of CD9 (Entrez Gene ID: 928, NM_001769 (Hu), NP_001760 (Hu))

SEQ ID NO: 10: Amino acid sequence of CD9 (Entrez Gene ID:928, NM_001769 (Hu), NP_001760 (Hu))

SEQ ID NO: 11: Nucleic acid sequence of CD49e (Entrez Gene ID: 3678, NM_002205 (Hu), NP_002196 (Hu))

SEQ ID NO: 12: Amino acid sequence of CD49e (Entrez Gene ID: 3678, NM_002205 (Hu), NP_002196 (Hu))

SEQ ID NO: 13: Nucleic acid sequence of CD44 (Entrez Gene ID: 960, NM_000610, NP_000601)

SEQ ID NO: 14: Amino acid sequence of CD44 (Entrez Gene ID: 960, NM_000610, NP_000601)

SEQ ID NO: 15: Nucleic acid sequence of CD73 (Entrez Gene ID: 4907, NM_001204813, NP_001191742)

SEQ ID NO: 16: Amino acid sequence of CD73 (Entrez Gene ID: 4907, NM_001204813, NP_001191742)

SEQ ID NO: 17:
primer CD166-F
CCCCAGAGGAATTTTTGTTTTAC

SEQ ID NO: 18:
primer CD166-R
AGCCTGATGTTATCTTTCATCCA

SEQ ID NO: 19:
primer CD73-F
GTTCCTGTAGTCCAGGCCTATG

SEQ ID NO: 20:
primer CD73-R
ACATTTCATCCGTGTGTCTCAG

SEQ ID NO: 21:
primer GAPDH-F
GAGTCAACGGATTTGGTCGT

SEQ ID NO: 22:
primer GAPDH-R
TTGATTTTGGAGGGATCTCG

The invention claimed is:

1. A method for differentiating between corneal endothelial cells with a non-fibroblastic phenotype and corneal endothelial cells with a fibroblastic phenotype in a sample comprising corneal endothelial cells with a non-fibroblastic phenotype and corneal endothelial cells with a fibroblastic phenotype, comprising at least one of:

detecting corneal endothelial cells with a non-fibroblastic phenotype in the sample by detecting at least one cell-surface marker present on corneal endothelial cells with a non-fibroblastic phenotype selected from the group consisting of CD166, HLA-A2, CD66a, CD66c, CD66d, CD66e, CD98, CD59, CD54, CD340, CD47, EGF-R, CD29, CD74, CD165, CD221, CD49a, SSEA-4, CD130, and CD49f, wherein the detecting comprises contacting the sample with a detection agent that binds the marker and detecting any binding between the detection agent and the marker, and wherein the cell-surface marker present on the corneal endothelial cell with a non-fibroblastic phenotype is expressed at a higher level compared to the expression level of the same cell-surface marker on a corneal endothelial cell with a fibroblastic phenotype, and detecting corneal endothelial cells with a fibroblastic phenotype in the sample by detecting at least one cell-surface marker present on corneal endothelial cells with a fibroblastic phenotype selected from the group consisting of CD26, CD9, CD49b, CD49e, CD13, CD99, CD105, CD63, CD58, CD201, CD56, CD44, CD55, CD71, CD73, CD91, HLA-DQ, CD164, CD49d, CD49c, CD90, MICA/B, CD46, CD140b, CD146, CD147, CD81, CD151, CD200, and CD10, wherein the detecting comprises contacting the sample with a detection agent that binds the marker and detecting any binding between the detection agent and the marker, and wherein the cell-surface marker present on the corneal endothelial cell with a fibroblastic phenotype is expressed at a higher level compared to the expression level of the same cell-surface marker on a corneal endothelial cell with a non-fibroblastic phenotype.

2. The method of claim 1, wherein the method comprises detecting at least one cell-surface marker present on corneal endothelial cells with a fibroblastic phenotype and detecting at least one cell-surface marker present on corneal endothelial cells with a non-fibroblastic phenotype.

3. The method of claim 1, wherein the method comprises detecting at least one cell-surface marker present on corneal endothelial cells with a non-fibroblastic phenotype selected from the group consisting of CD98, CD166, and CD340.

4. The method of claim 1, wherein the method comprises detecting at least one cell-surface marker present on corneal endothelial cells with a fibroblastic phenotype selected from the group consisting of CD9, CD49e, CD44, and CD73.

5. The method of claim 1, wherein the method comprises detecting at least one cell-surface marker present on corneal endothelial cells with a non-fibroblastic phenotype selected from the group consisting of CD98, CD166, and CD340, and detecting at least one cell-surface marker present on corneal endothelial cells with a fibroblastic phenotype selected from the group consisting of CD9, CD49e, CD44, and CD73.

6. The method of claim 1, wherein the method comprises detecting at least one of CD166 and CD73.

7. The method according to claim 1, wherein the detection agent for detecting corneal endothelial cells with a non-fibroblastic phenotype, and the detection agent for detecting corneal endothelial cells with a fibroblastic phenotype, if used, comprise(s) a staining agent.

8. The method of claim 1, further comprising determining the purity of the sample based on the relative amount of binding detected of a cell-surface marker present on corneal endothelial cells with a non-fibroblastic phenotype as compared to the binding detected of a cell-surface marker present on corneal endothelial cells with a fibroblastic phenotype.

9. The method of claim 1, further comprising, prior to the detecting, preparing the sample of corneal endothelial cells by inducing corneal endothelial cells from undifferentiated cells.

10. The method of claim 9, wherein the undifferentiated cells are induced pluripotent stem (iPS) cells or embryonic stem (ES) cells.

* * * * *

SEQUENCE LISTING

```
<160> NUMBER OF SEQ ID NOS: 22

<210> SEQ ID NO 1
<211> LENGTH: 1938
<212> TYPE: DNA
<213> ORGANISM: Homo sapiens
<220> FEATURE:
<221> NAME/KEY: CDS
<222> LOCATION: (153)..(1742)

<400> SEQUENCE: 1
cagaggccgc gcctgctgct gagcagatgc agtagccgaa actgcgcgga ggcacagagg      60
ccggggagag cgttctgggt ccgagggtcc aggtaggggt tgagccacca tctgaccgca     120
agctgcgtcg tgtcgccggt tctgcaggca cc atg agc cag gac acc gag gtg     173
                                   Met Ser Gln Asp Thr Glu Val
                                     1               5
```

```
gat atg aag gag gtg gag ctg aat gag tta gag ccc gag aag cag ccg      221
Asp Met Lys Glu Val Glu Leu Asn Glu Leu Glu Pro Glu Lys Gln Pro
         10                  15                  20 atg aac gcg gcg tct ggg gcg gcc atg tcc ctg gcg gga gcc gag aag      269
Met Asn Ala Ala Ser Gly Ala Ala Met Ser Leu Ala Gly Ala Glu Lys
 25                  30                  35 aat ggt ctg gtg aag atc aag gtg gcg gaa gac gag gcg gag gcg gca      317
Asn Gly Leu Val Lys Ile Lys Val Ala Glu Asp Glu Ala Glu Ala Ala
 40                  45                  50                  55 gcc gcg gct aag ttc acg ggc ctg tcc aag gag gag ctg ctg aag gtg      365
Ala Ala Ala Lys Phe Thr Gly Leu Ser Lys Glu Glu Leu Leu Lys Val
                 60                  65                  70 gca ggc agc ccc ggc tgg gta cgc acc cgc tgg gca ctg ctg ctg ctc      413
Ala Gly Ser Pro Gly Trp Val Arg Thr Arg Trp Ala Leu Leu Leu Leu
             75                  80                  85 ttc tgg ctc ggc tgg ctc ggc atg ctt gct ggt gcc gtg gtc ata atc      461
Phe Trp Leu Gly Trp Leu Gly Met Leu Ala Gly Ala Val Val Ile Ile
         90                  95                 100 gtg cga gcg ccg cgt tgt cgc gag cta ccg gcg cag aag tgg tgg cac      509
Val Arg Ala Pro Arg Cys Arg Glu Leu Pro Ala Gln Lys Trp Trp His
105                 110                 115 acg ggc gcc ctc tac cgc atc ggc gac ctt cag gcc ttc cag ggc cac      557
Thr Gly Ala Leu Tyr Arg Ile Gly Asp Leu Gln Ala Phe Gln Gly His
120                 125                 130                 135 ggc gcg ggc aac ctg gcg ggt ctg aag ggg cgt ctc gat tac ctg agc      605
Gly Ala Gly Asn Leu Ala Gly Leu Lys Gly Arg Leu Asp Tyr Leu Ser
                140                 145                 150 tct ctg aag gtg aag ggc ctt gtg ctg ggt cca att cac aag aac cag      653
Ser Leu Lys Val Lys Gly Leu Val Leu Gly Pro Ile His Lys Asn Gln
            155                 160                 165 aag gat gat gtc gct cag act gac ttg ctg cag atc gac ccc aat ttt      701
Lys Asp Asp Val Ala Gln Thr Asp Leu Leu Gln Ile Asp Pro Asn Phe
        170                 175                 180 ggc tcc aag gaa gat ttt gac agt ctc ttg caa tcg gct aaa aaa aag      749
Gly Ser Lys Glu Asp Phe Asp Ser Leu Leu Gln Ser Ala Lys Lys Lys
    185                 190                 195 agc atc cgt gtc att ctg gac ctt act ccc aac tac cgg ggt gag aac      797
Ser Ile Arg Val Ile Leu Asp Leu Thr Pro Asn Tyr Arg Gly Glu Asn
200                 205                 210                 215 tcg tgg ttc tcc act cag gtt gac act gtg gcc acc aag gtg aag gat      845
Ser Trp Phe Ser Thr Gln Val Asp Thr Val Ala Thr Lys Val Lys Asp
                220                 225                 230 gct ctg gag ttt tgg ctg caa gct ggc gtg gat ggg ttc cag gtt cgg      893
Ala Leu Glu Phe Trp Leu Gln Ala Gly Val Asp Gly Phe Gln Val Arg
            235                 240                 245 gac ata gag aat ctg aag gat gca tcc tca ttc ttg gct gag tgg caa      941
Asp Ile Glu Asn Leu Lys Asp Ala Ser Ser Phe Leu Ala Glu Trp Gln
        250                 255                 260 aat atc acc aag ggc ttc agt gaa gac agg ctc ttg att gcg ggg act      989
Asn Ile Thr Lys Gly Phe Ser Glu Asp Arg Leu Leu Ile Ala Gly Thr
    265                 270                 275 aac tcc tcc gac ctt cag cag atc ctg agc cta ctc gaa tcc aac aaa     1037
Asn Ser Ser Asp Leu Gln Gln Ile Leu Ser Leu Leu Glu Ser Asn Lys
280                 285                 290                 295 gac ttg ctg ttg act agc tca tac ctg tct gat tct ggt tct act ggg     1085
Asp Leu Leu Leu Thr Ser Ser Tyr Leu Ser Asp Ser Gly Ser Thr Gly
                300                 305                 310 gag cat aca aaa tcc cta gtc aca cag tat ttg aat gcc act ggc aat     1133
Glu His Thr Lys Ser Leu Val Thr Gln Tyr Leu Asn Ala Thr Gly Asn
```

```
                     315                 320                 325
cgc tgg tgc agc tgg agt ttg tct cag gca agg ctc ctg act tcc ttc      1181
Arg Trp Cys Ser Trp Ser Leu Ser Gln Ala Arg Leu Leu Thr Ser Phe
            330                 335                 340 ttg ccg gct caa ctt ctc cga ctc tac cag ctg atg ctc ttc acc ctg      1229
Leu Pro Ala Gln Leu Leu Arg Leu Tyr Gln Leu Met Leu Phe Thr Leu
345                 350                 355 cca ggg acc cct gtt ttc agc tac ggg gat gag att ggc ctg gat gca      1277
Pro Gly Thr Pro Val Phe Ser Tyr Gly Asp Glu Ile Gly Leu Asp Ala
360                 365                 370                 375 gct gcc ctt cct gga cag cct atg gag gct cca gtc atg ctg tgg gat      1325
Ala Ala Leu Pro Gly Gln Pro Met Glu Ala Pro Val Met Leu Trp Asp
            380                 385                 390 gag tcc agc ttc cct gac atc cca ggg gct gta agt gcc aac atg act      1373
Glu Ser Ser Phe Pro Asp Ile Pro Gly Ala Val Ser Ala Asn Met Thr
395                 400                 405 gtg aag ggc cag agt gaa gac cct ggc tcc ctc ctt tcc ttg ttc cgg      1421
Val Lys Gly Gln Ser Glu Asp Pro Gly Ser Leu Leu Ser Leu Phe Arg
            410                 415                 420 cgg ctg agt gac cag cgg agt aag gag cgc tcc cta ctg cat ggg gac      1469
Arg Leu Ser Asp Gln Arg Ser Lys Glu Arg Ser Leu Leu His Gly Asp
425                 430                 435 ttc cac gcg ttc tcc gct ggg cct gga ctc ttc tcc tat atc cgc cac      1517
Phe His Ala Phe Ser Ala Gly Pro Gly Leu Phe Ser Tyr Ile Arg His
440                 445                 450                 455 tgg gac cag aat gag cgt ttt ctg gta gtg ctt aac ttt ggg gat gtg      1565
Trp Asp Gln Asn Glu Arg Phe Leu Val Val Leu Asn Phe Gly Asp Val
            460                 465                 470 ggc ctc tcg gct gga ctg cag gcc tcc gac ctg cct gcc agc gcc agc      1613
Gly Leu Ser Ala Gly Leu Gln Ala Ser Asp Leu Pro Ala Ser Ala Ser
475                 480                 485 ctg cca gcc aag gct gac ctc ctc agc acc cag cca ggc cgt gag           1661
Leu Pro Ala Lys Ala Asp Leu Leu Ser Thr Gln Pro Gly Arg Glu
            490                 495                 500 gag ggc tcc cct ctt gag ctg gaa cgc ctg aaa ctg gag cct cac gaa      1709
Glu Gly Ser Pro Leu Glu Leu Glu Arg Leu Lys Leu Glu Pro His Glu
505                 510                 515 ggg ctg ctg ctc cgc ttc ccc tac gcg gcc tga cttcagcctg acatggaccc    1762
Gly Leu Leu Leu Arg Phe Pro Tyr Ala Ala
520                 525 actacccttc tcctttcctt cccaggccct ttggcttctg attttttctct tttttaaaaa   1822 caaacaaaca aactgttgca gattatgagt gaacccccaa atagggtgtt ttctgccttc    1882
aaataaaagt caccctgca tggtgaagtc ttccctctgc ttctctcata aaaaaa         1938

<210> SEQ ID NO 2
<211> LENGTH: 529
<212> TYPE: PRT
<213> ORGANISM: Homo sapiens

<400> SEQUENCE: 2

Met Ser Gln Asp Thr Glu Val Asp Met Lys Glu Val Glu Leu Asn Glu
1               5                   10                  15

Leu Glu Pro Glu Lys Gln Pro Met Asn Ala Ala Ser Gly Ala Ala Met
            20                  25                  30

Ser Leu Ala Gly Ala Glu Lys Asn Gly Leu Val Lys Ile Lys Val Ala
        35                  40                  45

Glu Asp Glu Ala Glu Ala Ala Ala Ala Ala Lys Phe Thr Gly Leu Ser
50                  55                  60
```

-continued

```
Lys Glu Glu Leu Leu Lys Val Ala Gly Ser Pro Gly Trp Val Arg Thr
65                  70                  75                  80

Arg Trp Ala Leu Leu Leu Phe Trp Leu Gly Trp Leu Gly Met Leu
                85                  90                  95

Ala Gly Ala Val Val Ile Ile Val Arg Ala Pro Arg Cys Arg Glu Leu
            100                 105                 110

Pro Ala Gln Lys Trp Trp His Thr Gly Ala Leu Tyr Arg Ile Gly Asp
            115                 120                 125

Leu Gln Ala Phe Gln Gly His Gly Ala Gly Asn Leu Ala Gly Leu Lys
        130                 135                 140

Gly Arg Leu Asp Tyr Leu Ser Ser Leu Lys Val Lys Gly Leu Val Leu
145                 150                 155                 160

Gly Pro Ile His Lys Asn Gln Lys Asp Val Ala Gln Thr Asp Leu
                165                 170                 175

Leu Gln Ile Asp Pro Asn Phe Gly Ser Lys Glu Asp Phe Asp Ser Leu
            180                 185                 190

Leu Gln Ser Ala Lys Lys Lys Ser Ile Arg Val Ile Leu Asp Leu Thr
        195                 200                 205

Pro Asn Tyr Arg Gly Glu Asn Ser Trp Phe Ser Thr Gln Val Asp Thr
210                 215                 220

Val Ala Thr Lys Val Lys Asp Ala Leu Glu Phe Trp Leu Gln Ala Gly
225                 230                 235                 240

Val Asp Gly Phe Gln Val Arg Asp Ile Glu Asn Leu Lys Asp Ala Ser
                245                 250                 255

Ser Phe Leu Ala Glu Trp Gln Asn Ile Thr Lys Gly Phe Ser Glu Asp
            260                 265                 270

Arg Leu Leu Ile Ala Gly Thr Asn Ser Ser Asp Leu Gln Gln Ile Leu
        275                 280                 285

Ser Leu Leu Glu Ser Asn Lys Asp Leu Leu Leu Thr Ser Ser Tyr Leu
290                 295                 300

Ser Asp Ser Gly Ser Thr Gly Glu His Thr Lys Ser Leu Val Thr Gln
305                 310                 315                 320

Tyr Leu Asn Ala Thr Gly Asn Arg Trp Cys Ser Trp Ser Leu Ser Gln
                325                 330                 335

Ala Arg Leu Leu Thr Ser Phe Leu Pro Ala Gln Leu Leu Arg Leu Tyr
            340                 345                 350

Gln Leu Met Leu Phe Thr Leu Pro Gly Thr Pro Val Phe Ser Tyr Gly
        355                 360                 365

Asp Glu Ile Gly Leu Asp Ala Ala Leu Pro Gly Gln Pro Met Glu
370                 375                 380

Ala Pro Val Met Leu Trp Asp Glu Ser Ser Phe Pro Asp Ile Pro Gly
385                 390                 395                 400

Ala Val Ser Ala Asn Met Thr Val Lys Gly Gln Ser Glu Asp Pro Gly
                405                 410                 415

Ser Leu Leu Ser Leu Phe Arg Arg Leu Ser Asp Gln Arg Ser Lys Glu
            420                 425                 430

Arg Ser Leu Leu His Gly Asp Phe His Ala Phe Ser Ala Gly Pro Gly
        435                 440                 445

Leu Phe Ser Tyr Ile Arg His Trp Asp Gln Asn Glu Arg Phe Leu Val
450                 455                 460

Val Leu Asn Phe Gly Asp Val Gly Leu Ser Ala Gly Leu Gln Ala Ser
465                 470                 475                 480
```

```
Asp Leu Pro Ala Ser Ala Ser Leu Pro Ala Lys Ala Asp Leu Leu Leu
                485                 490                 495

Ser Thr Gln Pro Gly Arg Glu Glu Gly Ser Pro Leu Glu Leu Glu Arg
        500                 505                 510

Leu Lys Leu Glu Pro His Glu Gly Leu Leu Leu Arg Phe Pro Tyr Ala
        515                 520                 525

Ala

<210> SEQ ID NO 3
<211> LENGTH: 4543
<212> TYPE: DNA
<213> ORGANISM: Homo sapiens
<220> FEATURE:
<221> NAME/KEY: CDS
<222> LOCATION: (73)..(1596)

<400> SEQUENCE: 3
cggcgggcgg cgcgcacact gctcgctggg ccgcggctcc cgggtgtccc aggcccggcc      60
ggtgcgcaga gc atg gcg ggt gcg ggc ccg aag cgg cgc gcg cta gcg gcg     111
              Met Ala Gly Ala Gly Pro Lys Arg Arg Ala Leu Ala Ala
              1               5                  10 ccg gcg gcc gag gag aag gaa gag gcg cgg gag aag atg ctg gcc gcc      159
Pro Ala Ala Glu Glu Lys Glu Glu Ala Arg Glu Lys Met Leu Ala Ala
        15                  20                  25 aag agc gcg gac ggc tcg gcg ccg gca ggc gag ggc gag ggc gtg acc      207
Lys Ser Ala Asp Gly Ser Ala Pro Ala Gly Glu Gly Glu Gly Val Thr
 30                  35                  40                  45 ctg cag cgg aac atc acg ctg ctc aac ggc gtg gcc atc atc gtg ggg      255
Leu Gln Arg Asn Ile Thr Leu Leu Asn Gly Val Ala Ile Ile Val Gly
                 50                  55                  60 acc att atc ggc tcg ggc atc ttc gtg acg ccc acg ggc gtg ctc aag      303
Thr Ile Ile Gly Ser Gly Ile Phe Val Thr Pro Thr Gly Val Leu Lys
             65                  70                  75 gag gca ggc tcg ccg ggg ctg gcg ctg gtg gtg tgg gcc gcg tgc ggc      351
Glu Ala Gly Ser Pro Gly Leu Ala Leu Val Val Trp Ala Ala Cys Gly
         80                  85                  90 gtc ttc tcc atc gtg ggc gcg ctc tgc tac gcg gag ctc ggc acc acc      399
Val Phe Ser Ile Val Gly Ala Leu Cys Tyr Ala Glu Leu Gly Thr Thr
     95                 100                 105 atc tcc aaa tcg ggc ggc gac tac gcc tac atg ctg gag gtc tac ggc      447
Ile Ser Lys Ser Gly Gly Asp Tyr Ala Tyr Met Leu Glu Val Tyr Gly
110                 115                 120                 125 tcg ctg ccc gcc ttc ctc aag ctc tgg atc gag ctc ctc atc atc cgg      495
Ser Leu Pro Ala Phe Leu Lys Leu Trp Ile Glu Leu Leu Ile Ile Arg
                130                 135                 140 cct tca tcg cag tac atc gtg gcc ctg gtc ttc gcc acc tac ctg ctc      543
Pro Ser Ser Gln Tyr Ile Val Ala Leu Val Phe Ala Thr Tyr Leu Leu
            145                 150                 155 aag ccg ctc ttc ccc acc tgc ccg gtg ccc gag gag gca gcc aag ctc      591
Lys Pro Leu Phe Pro Thr Cys Pro Val Pro Glu Glu Ala Ala Lys Leu
        160                 165                 170 gtg gcc tgc ctc tgc gtg ctg ctc acg gcc gtg aac tgc tac agc      639
Val Ala Cys Leu Cys Val Leu Leu Thr Ala Val Asn Cys Tyr Ser
    175                 180                 185 gtg aag gcc gcc acc cgg gtc cag gat gcc ttt gcc gcc gcc aag ctc      687
Val Lys Ala Ala Thr Arg Val Gln Asp Ala Phe Ala Ala Ala Lys Leu
190                 195                 200                 205 ctg gcc ctg gcc ctg atc atc ctg ctg ggc ttc gtc cag atc ggg aag      735
Leu Ala Leu Ala Leu Ile Ile Leu Leu Gly Phe Val Gln Ile Gly Lys
                210                 215                 220
```

```
ggt gat gtg tcc aat cta gat ccc aac ttc tca ttt gaa ggc acc aaa        783
Gly Asp Val Ser Asn Leu Asp Pro Asn Phe Ser Phe Glu Gly Thr Lys
            225                 230                 235 ctg gat gtg ggg aac att gtg ctg gca tta tac agc ggc ctc ttt gcc        831
Leu Asp Val Gly Asn Ile Val Leu Ala Leu Tyr Ser Gly Leu Phe Ala
        240                 245                 250 tat gga gga tgg aat tac ttg aat ttc gtc aca gag gaa atg atc aac        879
Tyr Gly Gly Trp Asn Tyr Leu Asn Phe Val Thr Glu Glu Met Ile Asn
    255                 260                 265 ccc tac aga aac ctg ccc ctg gcc atc atc atc tcc ctg ccc atc gtg        927
Pro Tyr Arg Asn Leu Pro Leu Ala Ile Ile Ile Ser Leu Pro Ile Val
270                 275                 280                 285 acg ctg gtg tac gtg ctg acc aac ctg gcc tac ttc acc acc ctg tcc        975
Thr Leu Val Tyr Val Leu Thr Asn Leu Ala Tyr Phe Thr Thr Leu Ser
                290                 295                 300 acc gag cag atg ctg tcg tcc gag gcc gtg gcc gtg gac ttc ggg aac       1023
Thr Glu Gln Met Leu Ser Ser Glu Ala Val Ala Val Asp Phe Gly Asn
            305                 310                 315 tat cac ctg ggc gtc atg tcc tgg atc atc ccc gtc ttc gtg ggc ctg       1071
Tyr His Leu Gly Val Met Ser Trp Ile Ile Pro Val Phe Val Gly Leu
        320                 325                 330 tcc tgc ttc ggc tcc gtc aat ggg tcc ctg ttc aca tcc tcc agg ctc       1119
Ser Cys Phe Gly Ser Val Asn Gly Ser Leu Phe Thr Ser Ser Arg Leu
    335                 340                 345 ttc ttc gtg ggg tcc cgg gaa ggc cac ctg ccc tcc atc ctc tcc atg       1167
Phe Phe Val Gly Ser Arg Glu Gly His Leu Pro Ser Ile Leu Ser Met
350                 355                 360                 365 atc cac cca cag ctc ctc acc ccc gtg ccg tcc ctc gtg ttc acg tgt       1215
Ile His Pro Gln Leu Leu Thr Pro Val Pro Ser Leu Val Phe Thr Cys
                370                 375                 380 gtg atg acg ctg ctc tac gcc ttc tcc aag gac atc ttc tcc gtc atc       1263
Val Met Thr Leu Leu Tyr Ala Phe Ser Lys Asp Ile Phe Ser Val Ile
            385                 390                 395 aac ttc ttc agc ttc ttc aac tgg ctc tgc gtg gcc ctg gcc atc atc       1311
Asn Phe Phe Ser Phe Phe Asn Trp Leu Cys Val Ala Leu Ala Ile Ile
        400                 405                 410 ggc atg atc tgg ctg cgc cac aga aag cct gag ctt gag cgg ccc atc       1359
Gly Met Ile Trp Leu Arg His Arg Lys Pro Glu Leu Glu Arg Pro Ile
    415                 420                 425 aag gtg aac ctg gcc ctg cct gtg ttc ttc atc ctg gcc tgc ctc ttc       1407
Lys Val Asn Leu Ala Leu Pro Val Phe Phe Ile Leu Ala Cys Leu Phe
430                 435                 440                 445 ctg atc gcc gtc tcc ttc tgg aag aca ccc gtg gag tgt ggc atc ggc       1455
Leu Ile Ala Val Ser Phe Trp Lys Thr Pro Val Glu Cys Gly Ile Gly
                450                 455                 460 ttc acc atc atc ctc agc ggg ctg ccc gtc tac ttc ttc ggg gtc tgg       1503
Phe Thr Ile Ile Leu Ser Gly Leu Pro Val Tyr Phe Phe Gly Val Trp
            465                 470                 475 tgg aaa aac aag ccc aag tgg ctc ctc cag ggc atc ttc tcc acg acc       1551
Trp Lys Asn Lys Pro Lys Trp Leu Leu Gln Gly Ile Phe Ser Thr Thr
        480                 485                 490 gtc ctg tgt cag aag ctc atg cag gtg gtc ccc cag gag aca tag           1596
Val Leu Cys Gln Lys Leu Met Gln Val Val Pro Gln Glu Thr
    495                 500                 505 ccaggaggcc gagtggctgc cggaggagca tgcgcagagg ccagttaaag tagatcacct    1656
cctcgaaccc actccggttc cccgcaaccc acagctcagc tgcccatccc agtccctcgc    1716
cgtccctccc aggtcgggca gtggaggctg ctgtgaaaac tctggtacga atctcatccc    1776
```

```
tcaactgagg gccagggacc caggtgtgcc tgtgctcctg cccaggagca gcttttggtc    1836
tccttgggcc cttttccct tccctccttt gtttacttat atatatattt tttttaaact    1896
taaattttgg gtcaacttga caccactaag atgattttt aaggagctgg gggaaggcag    1956
gagccttcct ttctcctgcc caagggccc agaccctggg caaacagagc tactgagact    2016
tggaacctca ttgctaccac agacttgcac tgaagccgga cagctgccca gacacatggg    2076
cttgtgacat tcgtgaaaac caaccctgtg ggcttatgtc tctgccttag ggtttgcaga    2136
gtggaaactc agccgtaggg tggcactggg aggggtggg ggatctgggc aaggtgggtg     2196
attcctccca ggaggtgctt gaggcccga tggactcctg accataatcc tagccccgag     2256
acaccatcct gagccaggga acagcccag ggttgggggg tgccggcatc tcccctagct     2316
caccaggcct ggcctctggg cagtgtggcc tcttggctat ttctgtgtcc agttttggag    2376
gctgagttct ggttcatgca gacaaagccc tgtccttcag tcttctagaa acagagacaa    2436
gaaaggcaga cacccgcgg ccaggcaccc atgtgggcgc ccaccctggg ctccacacag     2496
cagtgtcccc tgcccagag gtcgcagcta ccctcagcct ccaatgcatt ggcctctgta     2556
ccgcccggca gccccttctg gccggtgctg ggttcccact cccggcctag gcacctcccc    2616
gctctccctg tcacgctcat gtcctgtcct ggtcctgatg cccgttgtct aggagacaga    2676
gccaagcact gctcacgtct ctgccgcctg cgtttggagg cccctgggct ctacccagt     2736
ccccaccccgc ctgcagagag ggaactaggg caccccttgt ttctgttgtt cccgtgaatt   2796
tttttcgcta tgggaggcag ccgaggcctg gccaatgcgg cccacttccc tgagctgtcg    2856
ctgcctccat ggcagcagcc agggacccc agaacaagaa gaccccgcag gatccctcct     2916
gagctcgggg ggctctgcct tctcaggccc cgggcttccc ttctccccag ccagaggtgg    2976
agccaagtgg tccagcgtca ctccagtgct cagctgtggc tggaggagct ggcctgtggc    3036
acagccctga gtgtcccaag ccgggagcca acgaagccgg acacggcttc actgaccagc    3096
ggctgctcaa gccgcaagct ctcagcaagt gcccagtgga gcctgccgcc ccgcctggg     3156
caccgggacc ccctcaccat ccagtgggcc cggagaaacc tgatgaacag tttggggact    3216
caggaccaga tgtccgtctc tcttgcttga ggaatgaaga ccttattca ccctgcccc      3276
gttgcttccc gctgcacatg gacagacttc acagcgtctg ctcataggac ctgcatcctt    3336
cctggggacg aattccactc gtccaaggga cagcccacgg tctggaggcc gaggaccacc    3396
agcaggcagg tggactgact gtgttgggca agacctcttc cctctgggcc tgttctcttg    3456
gctgcaaata aggacagcag ctggtgcccc acctgcctgg tgcattgctg tgtgaatcca    3516
ggaggcagtg gacatcgtag gcagccacgg ccccgggtcc aggagaagtg ctccctggag    3576
gcacgcacca ctgcttccca ctggggccgg cggggcccac gcacgacgtc agcctcttac    3636
cttcccgcct cggctagggg tcctcgggat gccgttctgt tccaacctcc tgctctggga    3696
cgtggacatg cctcaaggat acaggagcc ggcggcctct cgacggcacg cacttgcctg     3756
ttggctgctg cggctgtggg cgagcatggg ggctgccagc gtctgttgtg gaaagtagct    3816
gctagtgaaa tggctggggc cgctggggtc cgtcttcaca ctgcgcaggt tcttctggg    3876
cgtctgagct ggggtgggag ctcctccgca gaaggttggt gggggggtcca gtctgtgatc   3936
cttggtgctg tgtgccccac tccagcctgg ggaccccact tcagaaggta ggggccgtgt    3996
ccgcgcggtgc tgactgaggc ctgcttcccc ctcccctcc tgctgtgctg gaattccaca    4056
gggaccaggg ccaccgcagg ggactgtctc agaagacttg atttttccgt cccttttcct    4116
ccacactcca ctgacaaacg tccccagcgg tttccacttg tgggcttcag gtgttttcaa    4176
```

-continued

```
gcacaaccca ccacaacaag caagtgcatt ttcagtcgtt gtgcttttt gttttgtgct    4236 aacgtcttac taatttaaag atgctgtcgg caccatgttt atttatttcc agtggtcatg    4296
ctcagccttg ctgctctgcg tggcgcaggt gccatgcctg ctccctgtct gtgtcccagc    4356
cacgcagggc catccactgt gacgtcggcc gaccaggctg acaccctct gccgagtaat     4416 gacgtgtgtg ctgggaccct tctttattct gtgttaatgg ctaacctgtt acactgggct    4476
gggttgggta gggtgttctg gctttttgt ggggttttta tttttaaaga aacactcaat     4536
catccta                                                               4543
```

<210> SEQ ID NO 4
<211> LENGTH: 507
<212> TYPE: PRT
<213> ORGANISM: Homo sapiens

<400> SEQUENCE: 4

Met Ala Gly Ala Gly Pro Lys Arg Arg Ala Leu Ala Ala Pro Ala Ala
 1               5                  10                  15

Glu Glu Lys Glu Glu Ala Arg Glu Lys Met Leu Ala Ala Lys Ser Ala
            20                  25                  30

Asp Gly Ser Ala Pro Ala Gly Glu Gly Glu Gly Val Thr Leu Gln Arg
        35                  40                  45

Asn Ile Thr Leu Leu Asn Gly Val Ala Ile Ile Val Gly Thr Ile Ile
    50                  55                  60

Gly Ser Gly Ile Phe Val Thr Pro Thr Gly Val Leu Lys Glu Ala Gly
65                  70                  75                  80

Ser Pro Gly Leu Ala Leu Val Val Trp Ala Ala Cys Gly Val Phe Ser
                85                  90                  95

Ile Val Gly Ala Leu Cys Tyr Ala Glu Leu Gly Thr Thr Ile Ser Lys
            100                 105                 110

Ser Gly Gly Asp Tyr Ala Tyr Met Leu Glu Val Tyr Gly Ser Leu Pro
        115                 120                 125

Ala Phe Leu Lys Leu Trp Ile Glu Leu Leu Ile Ile Arg Pro Ser Ser
    130                 135                 140

Gln Tyr Ile Val Ala Leu Val Phe Ala Thr Tyr Leu Leu Lys Pro Leu
145                 150                 155                 160

Phe Pro Thr Cys Pro Val Pro Glu Glu Ala Ala Lys Leu Val Ala Cys
                165                 170                 175

Leu Cys Val Leu Leu Leu Thr Ala Val Asn Cys Tyr Ser Val Lys Ala
            180                 185                 190

Ala Thr Arg Val Gln Asp Ala Phe Ala Ala Ala Lys Leu Leu Ala Leu
        195                 200                 205

Ala Leu Ile Ile Leu Leu Gly Phe Val Gln Ile Gly Lys Gly Asp Val
    210                 215                 220

Ser Asn Leu Asp Pro Asn Phe Ser Phe Glu Gly Thr Lys Leu Asp Val
225                 230                 235                 240

Gly Asn Ile Val Leu Ala Leu Tyr Ser Gly Leu Phe Ala Tyr Gly Gly
                245                 250                 255

Trp Asn Tyr Leu Asn Phe Val Thr Glu Glu Met Ile Asn Pro Tyr Arg
            260                 265                 270

Asn Leu Pro Leu Ala Ile Ile Ile Ser Leu Pro Ile Val Thr Leu Val
        275                 280                 285

Tyr Val Leu Thr Asn Leu Ala Tyr Phe Thr Thr Leu Ser Thr Glu Gln
    290                 295                 300

```
Met Leu Ser Ser Glu Ala Val Ala Val Asp Phe Gly Asn Tyr His Leu
305                 310                 315                 320

Gly Val Met Ser Trp Ile Ile Pro Val Phe Val Gly Leu Ser Cys Phe
            325                 330                 335

Gly Ser Val Asn Gly Ser Leu Phe Thr Ser Ser Arg Leu Phe Phe Val
        340                 345                 350

Gly Ser Arg Glu Gly His Leu Pro Ser Ile Leu Ser Met Ile His Pro
    355                 360                 365

Gln Leu Leu Thr Pro Val Pro Ser Leu Val Phe Thr Cys Val Met Thr
370                 375                 380

Leu Leu Tyr Ala Phe Ser Lys Asp Ile Phe Ser Val Ile Asn Phe Phe
385                 390                 395                 400

Ser Phe Phe Asn Trp Leu Cys Val Ala Leu Ala Ile Ile Gly Met Ile
                405                 410                 415

Trp Leu Arg His Arg Lys Pro Glu Leu Glu Arg Pro Ile Lys Val Asn
            420                 425                 430

Leu Ala Leu Pro Val Phe Phe Ile Leu Ala Cys Leu Phe Leu Ile Ala
        435                 440                 445

Val Ser Phe Trp Lys Thr Pro Val Glu Cys Gly Ile Gly Phe Thr Ile
    450                 455                 460

Ile Leu Ser Gly Leu Pro Val Tyr Phe Phe Gly Val Trp Trp Lys Asn
465                 470                 475                 480

Lys Pro Lys Trp Leu Leu Gln Gly Ile Phe Ser Thr Thr Val Leu Cys
                485                 490                 495

Gln Lys Leu Met Gln Val Val Pro Gln Glu Thr
            500                 505
```

<210> SEQ ID NO 5
<211> LENGTH: 4884
<212> TYPE: DNA
<213> ORGANISM: Homo sapiens
<220> FEATURE:
<221> NAME/KEY: CDS
<222> LOCATION: (697)..(2409)

<400> SEQUENCE: 5

```
gcacgcggtt ctccctgatc ccggagctgg gctcagggct cggactcagt cctgcagcgc      60
ctctaggctg cggatccgcg cttcaaccac ctgctttgcg ctgcgtccgg ggaagtgggg     120
aggagacggg agggagggag gaggcgggga gaggaggaaa gaggcagctt acacacgcct     180
tccagtccct ctactcagag cagcccggag accgctgccg ccgctgccgc tgctaccacc     240
gctgccacct gaggagaccc gccgcccccc cgtcgccgcc tcctgcgagt ccttcttagc     300
acctggcgtt tcatgcacat tgccactgcc attattatta tcattccaat acaaggaaaa     360
taaaagaaga taccagcgaa agaaccgct ctacaccttc cgaattactc aagtgtctcc     420
tggaaacaga gggtcgttgt ccccggagga gcagccgaag ggcccgtggg ctggtgttga     480
ccgggaggga ggaggagttg gggcattgc gtggtggaaa gttgcgtgcg cagagaacc     540
gaaggtgcag cgccacagcc caggggacgg tgtgtctggg agaagacgct gccctgcgt     600
cgggacccgc cagcgcgcgg gcaccgcggg gcccgggacg acgccccctc ctgcggcgtg     660
gactccgtca gtggcccacc aagaaggagg aggaat atg gaa tcc aag ggg gcc      714
                                        Met Glu Ser Lys Gly Ala
                                          1               5 agt tcc tgc cgt ctg ctc ttc tgc ctc ttg atc tcc gcc acc gtc ttc      762
Ser Ser Cys Arg Leu Leu Phe Cys Leu Leu Ile Ser Ala Thr Val Phe
```

|   |   |   |   |   |   |   |   |   |   |   |   |   |   |   |   |
|---|---|---|---|---|---|---|---|---|---|---|---|---|---|---|---|
| | | | 10 | | | | | 15 | | | | | 20 | | |
| agg | cca | ggc | ctt | gga | tgg | tat | act | gta | aat | tca | gca | tat | gga | gat | acc | 810
| Arg | Pro | Gly | Leu | Gly | Trp | Tyr | Thr | Val | Asn | Ser | Ala | Tyr | Gly | Asp | Thr |
| | | 25 | | | | 30 | | | | | 35 | | | | |

| att | atc | ata | cct | tgc | cga | ctt | gac | gta | cct | cag | aat | ctc | atg | ttt | ggc | 858
| Ile | Ile | Ile | Pro | Cys | Arg | Leu | Asp | Val | Pro | Gln | Asn | Leu | Met | Phe | Gly |
| 40 | | | | | 45 | | | | | 50 | | | | | |

| aaa | tgg | aaa | tat | gaa | aag | ccc | gat | ggc | tcc | cca | gta | ttt | att | gcc | ttc | 906
| Lys | Trp | Lys | Tyr | Glu | Lys | Pro | Asp | Gly | Ser | Pro | Val | Phe | Ile | Ala | Phe |
| 55 | | | | | 60 | | | | | 65 | | | | | 70 |

| aga | tcc | tct | aca | aag | aaa | agt | gtg | cag | tac | gac | gat | gta | cca | gaa | tac | 954
| Arg | Ser | Ser | Thr | Lys | Lys | Ser | Val | Gln | Tyr | Asp | Asp | Val | Pro | Glu | Tyr |
| | | | | 75 | | | | | 80 | | | | | 85 | |

| aaa | gac | aga | ttg | aac | ctc | tca | gaa | aac | tac | act | ttg | tct | atc | agt | aat | 1002
| Lys | Asp | Arg | Leu | Asn | Leu | Ser | Glu | Asn | Tyr | Thr | Leu | Ser | Ile | Ser | Asn |
| | | | 90 | | | | | 95 | | | | | 100 | | |

| gca | agg | atc | agt | gat | gaa | aag | aga | ttt | gtg | tgc | atg | cta | gta | act | gag | 1050
| Ala | Arg | Ile | Ser | Asp | Glu | Lys | Arg | Phe | Val | Cys | Met | Leu | Val | Thr | Glu |
| | | | 105 | | | | | 110 | | | | | 115 | | |

| gac | aac | gtg | ttt | gag | gca | cct | aca | ata | gtc | aag | gtg | ttc | aag | caa | cca | 1098
| Asp | Asn | Val | Phe | Glu | Ala | Pro | Thr | Ile | Val | Lys | Val | Phe | Lys | Gln | Pro |
| | | 120 | | | | | 125 | | | | | 130 | | | |

| tct | aaa | cct | gaa | att | gta | agc | aaa | gca | ctg | ttt | ctc | gaa | aca | gag | cag | 1146
| Ser | Lys | Pro | Glu | Ile | Val | Ser | Lys | Ala | Leu | Phe | Leu | Glu | Thr | Glu | Gln |
| 135 | | | | | 140 | | | | | 145 | | | | | 150 |

| cta | aaa | aag | ttg | ggt | gac | tgc | att | tca | gaa | gac | agt | tat | cca | gat | ggc | 1194
| Leu | Lys | Lys | Leu | Gly | Asp | Cys | Ile | Ser | Glu | Asp | Ser | Tyr | Pro | Asp | Gly |
| | | | | 155 | | | | | 160 | | | | | 165 | |

| aat | atc | aca | tgg | tac | agg | aat | gga | aaa | gtg | cta | cat | ccc | ctt | gaa | gga | 1242
| Asn | Ile | Thr | Trp | Tyr | Arg | Asn | Gly | Lys | Val | Leu | His | Pro | Leu | Glu | Gly |
| | | | 170 | | | | | 175 | | | | | 180 | | |

| gcg | gtg | gtc | ata | att | ttt | aaa | aag | gaa | atg | gac | cca | gtg | act | cag | ctc | 1290
| Ala | Val | Val | Ile | Ile | Phe | Lys | Lys | Glu | Met | Asp | Pro | Val | Thr | Gln | Leu |
| | | | 185 | | | | | 190 | | | | | 195 | | |

| tat | acc | atg | act | tcc | acc | ctg | gag | tac | aag | aca | acc | aag | gct | gac | ata | 1338
| Tyr | Thr | Met | Thr | Ser | Thr | Leu | Glu | Tyr | Lys | Thr | Thr | Lys | Ala | Asp | Ile |
| | | 200 | | | | | 205 | | | | | 210 | | | |

| caa | atg | cca | ttc | acc | tgc | tcg | gtg | aca | tat | tat | gga | cca | tct | ggc | cag | 1386
| Gln | Met | Pro | Phe | Thr | Cys | Ser | Val | Thr | Tyr | Tyr | Gly | Pro | Ser | Gly | Gln |
| 215 | | | | | 220 | | | | | 225 | | | | | 230 |

| aaa | aca | att | cat | tct | gaa | cag | gca | gta | ttt | gat | att | tac | tat | cct | aca | 1434
| Lys | Thr | Ile | His | Ser | Glu | Gln | Ala | Val | Phe | Asp | Ile | Tyr | Tyr | Pro | Thr |
| | | | | 235 | | | | | 240 | | | | | 245 | |

| gag | cag | gtg | aca | ata | caa | gtg | ctg | cca | cca | aaa | aat | gcc | atc | aaa | gaa | 1482
| Glu | Gln | Val | Thr | Ile | Gln | Val | Leu | Pro | Pro | Lys | Asn | Ala | Ile | Lys | Glu |
| | | | 250 | | | | | 255 | | | | | 260 | | |

| ggg | gat | aac | atc | act | ctt | aaa | tgc | tta | ggg | aat | ggc | aac | cct | ccc | cca | 1530
| Gly | Asp | Asn | Ile | Thr | Leu | Lys | Cys | Leu | Gly | Asn | Gly | Asn | Pro | Pro | Pro |
| | | | 265 | | | | | 270 | | | | | 275 | | |

| gag | gaa | ttt | ttg | ttt | tac | tta | cca | gga | cag | ccc | gaa | gga | ata | aga | agc | 1578
| Glu | Glu | Phe | Leu | Phe | Tyr | Leu | Pro | Gly | Gln | Pro | Glu | Gly | Ile | Arg | Ser |
| | | 280 | | | | | 285 | | | | | 290 | | | |

| tca | aat | act | tac | aca | ctg | acg | gat | gtg | agg | cgc | aat | gca | aca | gga | gac | 1626
| Ser | Asn | Thr | Tyr | Thr | Leu | Thr | Asp | Val | Arg | Arg | Asn | Ala | Thr | Gly | Asp |
| 295 | | | | | 300 | | | | | 305 | | | | | 310 |

| tac | aag | tgt | tcc | ctg | ata | gac | aaa | aaa | agc | atg | att | gct | tca | aca | gcc | 1674
| Tyr | Lys | Cys | Ser | Leu | Ile | Asp | Lys | Lys | Ser | Met | Ile | Ala | Ser | Thr | Ala |
| | | | | 315 | | | | | 320 | | | | | 325 | |

| atc | aca | gtt | cac | tat | ttg | gat | ttg | tcc | tta | aac | cca | agt | gga | gaa | gtg | 1722

```
Ile Thr Val His Tyr Leu Asp Leu Ser Leu Asn Pro Ser Gly Glu Val
            330                 335                 340 act aga cag att ggt gat gcc cta ccc gtg tca tgc aca ata tct gct      1770
Thr Arg Gln Ile Gly Asp Ala Leu Pro Val Ser Cys Thr Ile Ser Ala
            345                 350                 355 agc agg aat gca act gtg gta tgg atg aaa gat aac atc agg ctt cga      1818
Ser Arg Asn Ala Thr Val Val Trp Met Lys Asp Asn Ile Arg Leu Arg
        360                 365                 370 tct agc ccg tca ttt tct agt ctt cat tat cag gat gct gga aac tat      1866
Ser Ser Pro Ser Phe Ser Ser Leu His Tyr Gln Asp Ala Gly Asn Tyr
375                 380                 385                 390 gtc tgc gaa act gct ctg cag gag gtt gaa gga cta aag aaa aga gag      1914
Val Cys Glu Thr Ala Leu Gln Glu Val Glu Gly Leu Lys Lys Arg Glu
                395                 400                 405 tca ttg act ctc att gta gaa ggc aaa cct caa ata aaa atg aca aag      1962
Ser Leu Thr Leu Ile Val Glu Gly Lys Pro Gln Ile Lys Met Thr Lys
            410                 415                 420 aaa act gat ccc agt gga cta tct aaa aca ata atc tgc cat gtg gaa      2010
Lys Thr Asp Pro Ser Gly Leu Ser Lys Thr Ile Ile Cys His Val Glu
            425                 430                 435 ggt ttt cca aag cca gcc att caa tgg aca att act ggc agt gga agc      2058
Gly Phe Pro Lys Pro Ala Ile Gln Trp Thr Ile Thr Gly Ser Gly Ser
440                 445                 450 gtc ata aac caa aca gag gaa tct cct tat att aat ggc agg tat tat      2106
Val Ile Asn Gln Thr Glu Glu Ser Pro Tyr Ile Asn Gly Arg Tyr Tyr
455                 460                 465                 470 agt aaa att atc att tcc cct gaa gag aat gtt aca tta act tgc aca      2154
Ser Lys Ile Ile Ile Ser Pro Glu Glu Asn Val Thr Leu Thr Cys Thr
                475                 480                 485 gca gaa aac caa ctg gag aga aca gta aac tcc ttg aat gtc tct gct      2202
Ala Glu Asn Gln Leu Glu Arg Thr Val Asn Ser Leu Asn Val Ser Ala
            490                 495                 500 aat gaa aac aga gaa aag gtg aat gac cag gca aaa cta att gtg gga      2250
Asn Glu Asn Arg Glu Lys Val Asn Asp Gln Ala Lys Leu Ile Val Gly
        505                 510                 515 atc gtt gtt ggt ctc ctc ctt gct gcc ctt gtt gct ggt gtc gtc tac      2298
Ile Val Val Gly Leu Leu Leu Ala Ala Leu Val Ala Gly Val Val Tyr
520                 525                 530 tgg ctg tac atg aag aag tca aag act gca tca aaa cat gta aac aag      2346
Trp Leu Tyr Met Lys Lys Ser Lys Thr Ala Ser Lys His Val Asn Lys
535                 540                 545                 550 gac ctc ggt aat atg gaa gaa aac aaa aag tta gaa gaa aac aat cac      2394
Asp Leu Gly Asn Met Glu Glu Asn Lys Lys Leu Glu Glu Asn Asn His
                555                 560                 565 aaa act gaa gcc taa gagagaaact gtcctagttg tccagagata aaatcatat       2449
Lys Thr Glu Ala
        570 agaccaattg aagcatgaac gtggattgta tttaagacat aaacaaagac attgacagca    2509 attcatggtt caagtattaa gcagttcatt ctaccaagct gtcacaggtt ttcagagaat    2569 tatctcaagt aaaacaaatg aaatttaatt acaaacaata gaacaagtt ttggcagcca    2629 tgataatagg tcatatgttg tgtttggttc aattttttttt ccgtaaatgt ctgcactgag    2689 gatttctttt tggtttgcct tttatgtaaa ttttttacgt agctattttt atacactgta    2749 agctttgttc tgggagttgc tgttaatctg atgtataatg taatgttttt atttcaattg    2809 tttatatgga taatctgagc aggtacattt ctgattctga ttgctatcag caatgcccca    2869 aactttctca taagcaccta aaacccaaag gtggcagctt gtgaagattg gggacactca    2929
```

```
tattgccta attaaaaact gtgattttta tcacaaggga ggggaggccg agagtcagac    2989
tgatagacac cataggagcc gactctttga tatgccacca gcgaactctc agaaataaat    3049
cacagatgca tatagacaca catacataat ggtactccca aactgacaat tttacctatt    3109
ctgaaaaaga cataaaacag aatttggtag cacttacctc tacagacacc tgctaataaa    3169 ttatttctg tcaaaagaaa aaacacaagc atgtgtgaga gacagtttgg aaaaatcatg     3229
gtcaacattc ccattttcat agatcacaat gtaaatcact ataattacaa attggtgtta    3289
aatcctttgg gttatccact gccttaaaat tataccatt tcatgtttaa aaagatatca     3349
atcagaattg gagttttaa cagtggtcat tatcaaagct gtgttatttt ccacagaata     3409
tagaatatat atttttttcg tgtgtgtttt tgttaactac cctacagata ttgaatgcac    3469
cttgagataa tttagtgttt ttaactgata cataatttat caagcagtac atgaaagtgt    3529
aataataaaa tgtctatgta tctttagtta cattcaaatt tgtaacttta taaacatgtt    3589
ttatgcttga ggaaatttt aaggtggtag tataaatgga aacttttga agtagaccag      3649 atatgggcta cttgtgacta gactttaaa ctttgctctt tcaagcagaa gcctggtttc      3709
tgggagaaca ctgcacagcg atttctttcc caggatttac acaactttaa agggaagata    3769
aatgaacatc agatttctag gtatagaact atgttattga aaggaaaagg aaaactggtg    3829
tttgtttctt agactcatga aataaaaaat tatgaaggca atgaaaaata aattgaaaat    3889
taaagtcaga tgagaatagg aataatactt tgccacttct gcattattta gaaacatacg    3949
ttattgtaca tttgtaaacc atttactgtc tgggcaatag tgactccgtt taataaaagc    4009
ttccgtagtg cattggtatg gattaaatgc ataaaatatt cttagactcg atgctgtata    4069
aaatattatg ggaaaaaaag aaaatacgtt attttgcctc taaactttta ttgaagtttt    4129
atttggcagg aaaaaaaatt gaatcttggt caacatttaa accaaagtaa aagggggaaaa   4189 accaaagtta tttgttttgc atggctaagc cattctgtta tctctgtaaa tactgtgatt    4249 tctttttat tttctcttta gaattttgtt aagaaattc taaaatttt aaacacctgc        4309 tctccacaat aaatcacaaa cactaaaata aaattacttc catataaata ttatttctc      4369 ttttggtgtg ggagatcaaa ggtttaaagt ctaacttcta agatatattt gcagaaagaa    4429
gcaacatgac aatagagaga gttatgctac aattatttct tggtttccac ttgcaatggt    4489
taattaagtc caaaaacagc tgtcagaacc tcgagagcag aacatgagaa actcagagct    4549
ctggaccgaa agcagaaagt ttgccgggaa aaaaaaagac aacattatta ccatcgattc    4609
agtgcctgga taagaggaa agcttacttg tttaatggca gccacatgca cgaagatgct    4669
aagaagaaaa agaattccaa atcctcaact tttgaggttt cggctctcca atttaactct    4729
ttggcaacag gaaacaggtt ttgcaagttc aaggttcact ccctatatgt gattatagga    4789
attgtttgtg gaaatggatt aacatacccg tctatgccta aagataata aaactgaaat      4849 atgtcttcac aggtctccca caaaaaaaaa aaaaa                               4884
```

<210> SEQ ID NO 6
<211> LENGTH: 570
<212> TYPE: PRT
<213> ORGANISM: Homo sapiens

<400> SEQUENCE: 6

```
Met Glu Ser Lys Gly Ala Ser Ser Cys Arg Leu Leu Phe Cys Leu Leu
1               5                   10                  15

Ile Ser Ala Thr Val Phe Arg Pro Gly Leu Gly Trp Tyr Thr Val Asn
            20                  25                  30
```

-continued

Ser Ala Tyr Gly Asp Thr Ile Ile Pro Cys Arg Leu Asp Val Pro
        35              40                  45

Gln Asn Leu Met Phe Gly Lys Trp Lys Tyr Glu Lys Pro Asp Gly Ser
 50                  55                  60

Pro Val Phe Ile Ala Phe Arg Ser Ser Thr Lys Lys Ser Val Gln Tyr
 65              70                  75                  80

Asp Asp Val Pro Glu Tyr Lys Asp Arg Leu Asn Leu Ser Glu Asn Tyr
                 85                  90                  95

Thr Leu Ser Ile Ser Asn Ala Arg Ile Ser Asp Glu Lys Arg Phe Val
            100                 105                 110

Cys Met Leu Val Thr Glu Asp Asn Val Phe Glu Ala Pro Thr Ile Val
             115                 120                 125

Lys Val Phe Lys Gln Pro Ser Lys Pro Glu Ile Val Ser Lys Ala Leu
            130                 135                 140

Phe Leu Glu Thr Glu Gln Leu Lys Lys Leu Gly Asp Cys Ile Ser Glu
145                 150                 155                 160

Asp Ser Tyr Pro Asp Gly Asn Ile Thr Trp Tyr Arg Asn Gly Lys Val
                165                 170                 175

Leu His Pro Leu Glu Gly Ala Val Val Ile Ile Phe Lys Lys Glu Met
            180                 185                 190

Asp Pro Val Thr Gln Leu Tyr Thr Met Thr Ser Thr Leu Glu Tyr Lys
            195                 200                 205

Thr Thr Lys Ala Asp Ile Gln Met Pro Phe Thr Cys Ser Val Thr Tyr
        210                 215                 220

Tyr Gly Pro Ser Gly Gln Lys Thr Ile His Ser Glu Gln Ala Val Phe
225                 230                 235                 240

Asp Ile Tyr Tyr Pro Thr Glu Gln Val Thr Ile Gln Val Leu Pro Pro
                245                 250                 255

Lys Asn Ala Ile Lys Glu Gly Asp Asn Ile Thr Leu Lys Cys Leu Gly
            260                 265                 270

Asn Gly Asn Pro Pro Glu Glu Phe Leu Phe Tyr Leu Pro Gly Gln
        275                 280                 285

Pro Glu Gly Ile Arg Ser Ser Asn Thr Tyr Thr Leu Thr Asp Val Arg
            290                 295                 300

Arg Asn Ala Thr Gly Asp Tyr Lys Cys Ser Leu Ile Asp Lys Lys Ser
305                 310                 315                 320

Met Ile Ala Ser Thr Ala Ile Thr Val His Tyr Leu Asp Leu Ser Leu
                325                 330                 335

Asn Pro Ser Gly Glu Val Thr Arg Gln Ile Gly Asp Ala Leu Pro Val
            340                 345                 350

Ser Cys Thr Ile Ser Ala Ser Arg Asn Ala Thr Val Val Trp Met Lys
        355                 360                 365

Asp Asn Ile Arg Leu Arg Ser Ser Pro Ser Phe Ser Ser Leu His Tyr
370                 375                 380

Gln Asp Ala Gly Asn Tyr Val Cys Glu Thr Ala Leu Gln Glu Val Glu
385                 390                 395                 400

Gly Leu Lys Lys Arg Glu Ser Leu Thr Leu Ile Val Glu Gly Lys Pro
                405                 410                 415

Gln Ile Lys Met Thr Lys Lys Thr Asp Pro Ser Gly Leu Ser Lys Thr
            420                 425                 430

Ile Ile Cys His Val Glu Gly Phe Pro Lys Pro Ala Ile Gln Trp Thr
            435                 440                 445

```
Ile Thr Gly Ser Gly Ser Val Ile Asn Gln Thr Glu Glu Ser Pro Tyr
            450                 455                 460

Ile Asn Gly Arg Tyr Tyr Ser Lys Ile Ile Ser Pro Glu Asn
465                 470                 475                 480

Val Thr Leu Thr Cys Thr Ala Glu Asn Gln Leu Glu Arg Thr Val Asn
                485                 490                 495

Ser Leu Asn Val Ser Ala Asn Glu Asn Arg Glu Lys Val Asn Asp Gln
            500                 505                 510

Ala Lys Leu Ile Val Gly Ile Val Gly Leu Leu Leu Ala Ala Leu
        515                 520                 525

Val Ala Gly Val Val Tyr Trp Leu Tyr Met Lys Lys Ser Lys Thr Ala
530                 535                 540

Ser Lys His Val Asn Lys Asp Leu Gly Asn Met Glu Glu Asn Lys Lys
545                 550                 555                 560

Leu Glu Glu Asn Asn His Lys Thr Glu Ala
            565                 570

<210> SEQ ID NO 7
<211> LENGTH: 4816
<212> TYPE: DNA
<213> ORGANISM: Homo sapiens
<220> FEATURE:
<221> NAME/KEY: CDS
<222> LOCATION: (521)..(4198)

<400> SEQUENCE: 7
gttcccggat ttttgtgggc gcctgccccg cccctcgtcc cctgctgtg tccatatatc    60 gaggcgatag ggttaaggga aggcggacgc ctgatgggtt aatgagcaaa ctgaagtgtt   120
ttccatgatc tttttgagt cgcaattgaa gtaccactc ccgagggtga ttgcttcccc    180 atgcgggta gaacctttgc tgtcctgttc accactctac ctccagcaca gaatttggct   240
tatgcctact caatgtgaag atgatgagga tgaaaacctt tgtgatgatc cacttccact   300
taatgaatgg tggcaaagca agctatatt caagaccaca tgcaaagcta ctccctgagc    360
aaagagtcac agataaaacg ggggcaccag tagaatggcc aggacaaacg cagtgcagca   420
cagagactca gaccctggca gccatgcctg cgcaggcagt gatgagagtg acatgtactg   480
ttgtggacat gcacaaaagt gagtgtgcac cggcacagac atg aag ctg cgg ctc   535
                                              Met Lys Leu Arg Leu
                                              1               5 cct gcc agt ccc gag acc cac ctg gac atg ctc cgc cac ctc tac cag   583
Pro Ala Ser Pro Glu Thr His Leu Asp Met Leu Arg His Leu Tyr Gln
            10                  15                  20 ggc tgc cag gtg gtg cag gga aac ctg gaa ctc acc tac ctg ccc acc   631
Gly Cys Gln Val Val Gln Gly Asn Leu Glu Leu Thr Tyr Leu Pro Thr
        25                  30                  35 aat gcc agc ctg tcc ttc ctg cag gat atc cag gag gtg cag ggc tac   679
Asn Ala Ser Leu Ser Phe Leu Gln Asp Ile Gln Glu Val Gln Gly Tyr
    40                  45                  50 gtg ctc atc gct cac aac caa gtg agg cag gtc cca ctg cag agg ctg   727
Val Leu Ile Ala His Asn Gln Val Arg Gln Val Pro Leu Gln Arg Leu
55                  60                  65 cgg att gtg cga ggc acc cag ctc ttt gag gac aac tat gcc ctg gcc   775
Arg Ile Val Arg Gly Thr Gln Leu Phe Glu Asp Asn Tyr Ala Leu Ala
70                  75                  80                  85 gtg cta gac aat gga gac ccg ctg aac aat acc acc cct gtc aca ggg   823
Val Leu Asp Asn Gly Asp Pro Leu Asn Asn Thr Thr Pro Val Thr Gly
            90                  95                  100
```

-continued

| | | |
|---|---|---|
| gcc tcc cca gga ggc ctg cgg gag ctg cag ctt cga agc ctc aca gag<br>Ala Ser Pro Gly Gly Leu Arg Glu Leu Gln Leu Arg Ser Leu Thr Glu<br>          105                     110                     115 | 871 | |
| atc ttg aaa gga ggg gtc ttg atc cag cgg aac ccc cag ctc tgc tac<br>Ile Leu Lys Gly Gly Val Leu Ile Gln Arg Asn Pro Gln Leu Cys Tyr<br>     120                     125                     130 | 919 | |
| cag gac acg att ttg tgg aag gac atc ttc cac aag aac aac cag ctg<br>Gln Asp Thr Ile Leu Trp Lys Asp Ile Phe His Lys Asn Asn Gln Leu<br>             135                     140                     145 | 967 | |
| gct ctc aca ctg ata gac acc aac cgc tct cgg gcc tgc cac ccc tgt<br>Ala Leu Thr Leu Ile Asp Thr Asn Arg Ser Arg Ala Cys His Pro Cys<br>150                     155                     160                 165 | 1015 | |
| tct ccg atg tgt aag ggc tcc cgc tgt tgg gga gag agt tct gag gat<br>Ser Pro Met Cys Lys Gly Ser Arg Cys Trp Gly Glu Ser Ser Glu Asp<br>                 170                     175                     180 | 1063 | |
| tgt cag agc ctg acg cgc act gtc tgt gcc ggt ggc tgt gcc cgc tgc<br>Cys Gln Ser Leu Thr Arg Thr Val Cys Ala Gly Gly Cys Ala Arg Cys<br>         185                     190                     195 | 1111 | |
| aag ggg cca ctg ccc act gac tgc tgc cat gag cag tgt gct gcc ggc<br>Lys Gly Pro Leu Pro Thr Asp Cys Cys His Glu Gln Cys Ala Ala Gly<br>             200                     205                     210 | 1159 | |
| tgc acg ggc ccc aag cac tct gac tgc ctg gcc tgc ctc cac ttc aac<br>Cys Thr Gly Pro Lys His Ser Asp Cys Leu Ala Cys Leu His Phe Asn<br>215                     220                     225 | 1207 | |
| cac agt ggc atc tgt gag ctg cac tgc cca gcc ctg gtc acc tac aac<br>His Ser Gly Ile Cys Glu Leu His Cys Pro Ala Leu Val Thr Tyr Asn<br>230                     235                     240                 245 | 1255 | |
| aca gac acg ttt gag tcc atg ccc aat ccc gag ggc cgg tat aca ttc<br>Thr Asp Thr Phe Glu Ser Met Pro Asn Pro Glu Gly Arg Tyr Thr Phe<br>                 250                     255                     260 | 1303 | |
| ggc gcc agc tgt gtg act gcc tgt ccc tac aac tac ctt tct acg gac<br>Gly Ala Ser Cys Val Thr Ala Cys Pro Tyr Asn Tyr Leu Ser Thr Asp<br>         265                     270                     275 | 1351 | |
| gtg gga tcc tgc acc ctc gtc tgc ccc ctg cac aac caa gag gtg aca<br>Val Gly Ser Cys Thr Leu Val Cys Pro Leu His Asn Gln Glu Val Thr<br>             280                     285                     290 | 1399 | |
| gca gag gat gga aca cag cgg tgt gag aag tgc agc aag ccc tgt gcc<br>Ala Glu Asp Gly Thr Gln Arg Cys Glu Lys Cys Ser Lys Pro Cys Ala<br>295                     300                     305 | 1447 | |
| cga gtg tgc tat ggt ctg ggc atg gag cac ttg cga gag gtg agg gca<br>Arg Val Cys Tyr Gly Leu Gly Met Glu His Leu Arg Glu Val Arg Ala<br>310                     315                     320                 325 | 1495 | |
| gtt acc agt gcc aat atc cag gag ttt gct ggc tgc aag aag atc ttt<br>Val Thr Ser Ala Asn Ile Gln Glu Phe Ala Gly Cys Lys Lys Ile Phe<br>                 330                     335                     340 | 1543 | |
| ggg agc ctg gca ttt ctg ccg gag agc ttt gat ggg gac cca gcc tcc<br>Gly Ser Leu Ala Phe Leu Pro Glu Ser Phe Asp Gly Asp Pro Ala Ser<br>         345                     350                     355 | 1591 | |
| aac act gcc ccg ctc cag cca gag cag ctc caa gtg ttt gag act ctg<br>Asn Thr Ala Pro Leu Gln Pro Glu Gln Leu Gln Val Phe Glu Thr Leu<br>             360                     365                     370 | 1639 | |
| gaa gag atc aca ggt tac cta tac atc tca gca tgg ccg gac agc ctg<br>Glu Glu Ile Thr Gly Tyr Leu Tyr Ile Ser Ala Trp Pro Asp Ser Leu<br>375                     380                     385 | 1687 | |
| cct gac ctc agc gtc ttc cag aac ctg caa gta atc cgg gga cga att<br>Pro Asp Leu Ser Val Phe Gln Asn Leu Gln Val Ile Arg Gly Arg Ile<br>390                     395                     400                 405 | 1735 | |
| ctg cac aat ggc gcc tac tcg ctg acc ctg caa ggg ctg ggc atc agc<br>Leu His Asn Gly Ala Tyr Ser Leu Thr Leu Gln Gly Leu Gly Ile Ser<br>                 410                     415                     420 | 1783 | |

|  |  |
|---|---|
| tgg ctg ggg ctg cgc tca ctg agg gaa ctg ggc agt gga ctg gcc ctc<br>Trp Leu Gly Leu Arg Ser Leu Arg Glu Leu Gly Ser Gly Leu Ala Leu<br>425 430 435 | 1831 |
| atc cac cat aac acc cac ctc tgc ttc gtg cac acg gtg ccc tgg gac<br>Ile His His Asn Thr His Leu Cys Phe Val His Thr Val Pro Trp Asp<br>440 445 450 | 1879 |
| cag ctc ttt cgg aac ccg cac caa gct ctg ctc cac act gcc aac cgg<br>Gln Leu Phe Arg Asn Pro His Gln Ala Leu Leu His Thr Ala Asn Arg<br>455 460 465 | 1927 |
| cca gag gac gag tgt gtg ggc gag ggc ctg gcc tgc cac cag ctg tgc<br>Pro Glu Asp Glu Cys Val Gly Glu Gly Leu Ala Cys His Gln Leu Cys<br>470 475 480 485 | 1975 |
| gcc cga ggg cac tgc tgg ggt cca ggg ccc acc cag tgt gtc aac tgc<br>Ala Arg Gly His Cys Trp Gly Pro Gly Pro Thr Gln Cys Val Asn Cys<br>490 495 500 | 2023 |
| agc cag ttc ctt cgg ggc cag gag tgc gtg gag gaa tgc cga gta ctg<br>Ser Gln Phe Leu Arg Gly Gln Glu Cys Val Glu Glu Cys Arg Val Leu<br>505 510 515 | 2071 |
| cag ggg ctc ccc agg gag tat gtg aat gcc agg cac tgt ttg ccg tgc<br>Gln Gly Leu Pro Arg Glu Tyr Val Asn Ala Arg His Cys Leu Pro Cys<br>520 525 530 | 2119 |
| cac cct gag tgt cag ccc cag aat ggc tca gtg acc tgt ttt gga ccg<br>His Pro Glu Cys Gln Pro Gln Asn Gly Ser Val Thr Cys Phe Gly Pro<br>535 540 545 | 2167 |
| gag gct gac cag tgt gtg gcc tgt gcc cac tat aag gac cct ccc ttc<br>Glu Ala Asp Gln Cys Val Ala Cys Ala His Tyr Lys Asp Pro Pro Phe<br>550 555 560 565 | 2215 |
| tgc gtg gcc cgc tgc ccc agc ggt gtg aaa cct gac ctc tcc tac atg<br>Cys Val Ala Arg Cys Pro Ser Gly Val Lys Pro Asp Leu Ser Tyr Met<br>570 575 580 | 2263 |
| ccc atc tgg aag ttt cca gat gag gag ggc gca tgc cag cct tgc ccc<br>Pro Ile Trp Lys Phe Pro Asp Glu Glu Gly Ala Cys Gln Pro Cys Pro<br>585 590 595 | 2311 |
| atc aac tgc acc cac tcc tgt gtg gac ctg gat gac aag ggc tgc ccc<br>Ile Asn Cys Thr His Ser Cys Val Asp Leu Asp Asp Lys Gly Cys Pro<br>600 605 610 | 2359 |
| gcc gag cag aga gcc agc cct ctg acg tcc atc atc tct gcg gtg gtt<br>Ala Glu Gln Arg Ala Ser Pro Leu Thr Ser Ile Ile Ser Ala Val Val<br>615 620 625 | 2407 |
| ggc att ctg ctg gtc gtg gtc ttg ggg gtg gtc ttt ggg atc ctc atc<br>Gly Ile Leu Leu Val Val Val Leu Gly Val Val Phe Gly Ile Leu Ile<br>630 635 640 645 | 2455 |
| aag cga cgg cag cag aag atc cgg aag tac acg atg cgg aga ctg ctg<br>Lys Arg Arg Gln Gln Lys Ile Arg Lys Tyr Thr Met Arg Arg Leu Leu<br>650 655 660 | 2503 |
| cag gaa acg gag ctg gtg gag ccg ctg aca cct agc gga gcg atg ccc<br>Gln Glu Thr Glu Leu Val Glu Pro Leu Thr Pro Ser Gly Ala Met Pro<br>665 670 675 | 2551 |
| aac cag gcg cag atg cgg atc ctg aaa gag acg gag ctg agg aag gtg<br>Asn Gln Ala Gln Met Arg Ile Leu Lys Glu Thr Glu Leu Arg Lys Val<br>680 685 690 | 2599 |
| aag gtg ctt gga tct ggc gct ttt ggc aca gtc tac aag ggc atc tgg<br>Lys Val Leu Gly Ser Gly Ala Phe Gly Thr Val Tyr Lys Gly Ile Trp<br>695 700 705 | 2647 |
| atc cct gat ggg gag aat gtg aaa att cca gtg gcc atc aaa gtg ttg<br>Ile Pro Asp Gly Glu Asn Val Lys Ile Pro Val Ala Ile Lys Val Leu<br>710 715 720 725 | 2695 |
| agg gaa aac aca tcc ccc aaa gcc aac aaa gaa atc tta gac gaa gca<br>Arg Glu Asn Thr Ser Pro Lys Ala Asn Lys Glu Ile Leu Asp Glu Ala | 2743 |

-continued

```
              730                 735                 740
tac gtg atg gct ggt gtg ggc tcc cca tat gtc tcc cgc ctt ctg ggc    2791
Tyr Val Met Ala Gly Val Gly Ser Pro Tyr Val Ser Arg Leu Leu Gly
                745                 750                 755 atc tgc ctg aca tcc acg gtg cag ctg gtg aca cag ctt atg ccc tat    2839
Ile Cys Leu Thr Ser Thr Val Gln Leu Val Thr Gln Leu Met Pro Tyr
            760                 765                 770 ggc tgc ctc tta gac cat gtc cgg gaa aac cgc gga cgc ctg ggc tcc    2887
Gly Cys Leu Leu Asp His Val Arg Glu Asn Arg Gly Arg Leu Gly Ser
775                 780                 785 cag gac ctg ctg aac tgg tgt atg cag att gcc aag ggg atg agc tac    2935
Gln Asp Leu Leu Asn Trp Cys Met Gln Ile Ala Lys Gly Met Ser Tyr
790                 795                 800                 805 ctg gag gat gtg cgg ctc gta cac agg gac ttg gcc gct cgg aac gtg    2983
Leu Glu Asp Val Arg Leu Val His Arg Asp Leu Ala Ala Arg Asn Val
                810                 815                 820 ctg gtc aag agt ccc aac cat gtc aaa att aca gac ttc ggg ctg gct    3031
Leu Val Lys Ser Pro Asn His Val Lys Ile Thr Asp Phe Gly Leu Ala
            825                 830                 835 cgg ctg ctg gac att gac gag aca gag tac cat gca gat ggg ggc aag    3079
Arg Leu Leu Asp Ile Asp Glu Thr Glu Tyr His Ala Asp Gly Gly Lys
        840                 845                 850 gtg ccc atc aag tgg atg gcg ctg gag tcc att ctc cgc cgg cgg ttc    3127
Val Pro Ile Lys Trp Met Ala Leu Glu Ser Ile Leu Arg Arg Arg Phe
855                 860                 865 acc cac cag agt gat gtg tgg agt tat ggt gtg act gtg tgg gag ctg    3175
Thr His Gln Ser Asp Val Trp Ser Tyr Gly Val Thr Val Trp Glu Leu
870                 875                 880                 885 atg act ttt ggg gcc aaa cct tac gat ggg atc cca gcc cgg gag atc    3223
Met Thr Phe Gly Ala Lys Pro Tyr Asp Gly Ile Pro Ala Arg Glu Ile
                890                 895                 900 cct gac ctg ctg gaa aag ggg gag cgg ctg ccc cag ccc ccc atc tgc    3271
Pro Asp Leu Leu Glu Lys Gly Glu Arg Leu Pro Gln Pro Pro Ile Cys
            905                 910                 915 acc att gat gtc tac atg atc atg gtc aaa tgt tgg atg att gac tct    3319
Thr Ile Asp Val Tyr Met Ile Met Val Lys Cys Trp Met Ile Asp Ser
        920                 925                 930 gaa tgt cgg cca aga ttc cgg gag ttg gtg tct gaa ttc tcc cgc atg    3367
Glu Cys Arg Pro Arg Phe Arg Glu Leu Val Ser Glu Phe Ser Arg Met
935                 940                 945 gcc agg gac ccc cag cgc ttt gtg gtc atc cag aat gag gac ttg ggc    3415
Ala Arg Asp Pro Gln Arg Phe Val Val Ile Gln Asn Glu Asp Leu Gly
950                 955                 960                 965 cca gcc agt ccc ttg gac agc acc ttc tac cgc tca ctg ctg gag gac    3463
Pro Ala Ser Pro Leu Asp Ser Thr Phe Tyr Arg Ser Leu Leu Glu Asp
                970                 975                 980 gat gac atg ggg gac ctg gtg gat gct gag gag tat ctg gta ccc cag    3511
Asp Asp Met Gly Asp Leu Val Asp Ala Glu Glu Tyr Leu Val Pro Gln
            985                 990                 995 cag ggc ttc  ttc tgt cca gac cct  gcc ccg ggc gct ggg  ggc atg     3556
Gln Gly Phe Phe Cys Pro Asp Pro Ala Pro Gly Ala Gly Gly Met
            1000                1005                1010 gtc cac cac  agg cac cgc agc tca  tct acc agg agt ggc  ggt ggg     3601
Val His His Arg His Arg Ser Ser Ser Thr Arg Ser Gly Gly Gly
            1015                1020                1025 gac ctg aca  cta ggg ctg gag ccc  tct gaa gag gag gcc  ccc agg     3646
Asp Leu Thr Leu Gly Leu Glu Pro Ser Glu Glu Glu Ala Pro Arg
            1030                1035                1040 tct cca ctg gca ccc tcc gaa ggg  gct ggc tcc gat gta  ttt gat     3691
Ser Pro Leu Ala Pro Ser Glu Gly Ala Gly Ser Asp Val Phe Asp
```

```
Ser Pro Leu Ala Pro Ser Glu Gly Ala Gly Ser Asp Val Phe Asp
        1045                1050                1055 ggt gac ctg gga atg ggg gca gcc aag ggg ctg caa agc ctc ccc      3736
Gly Asp Leu Gly Met Gly Ala Ala Lys Gly Leu Gln Ser Leu Pro
        1060                1065                1070 aca cat gac ccc agc cct cta cag cgg tac agt gag gac ccc aca      3781
Thr His Asp Pro Ser Pro Leu Gln Arg Tyr Ser Glu Asp Pro Thr
        1075                1080                1085 gta ccc ctg ccc tct gag act gat ggc tac gtt gcc ccc ctg acc      3826
Val Pro Leu Pro Ser Glu Thr Asp Gly Tyr Val Ala Pro Leu Thr
        1090                1095                1100 tgc agc ccc cag cct gaa tat gtg aac cag cca gat gtt cgg ccc      3871
Cys Ser Pro Gln Pro Glu Tyr Val Asn Gln Pro Asp Val Arg Pro
        1105                1110                1115 cag ccc cct tcg ccc cga gag ggc cct ctg cct gct gcc cga cct      3916
Gln Pro Pro Ser Pro Arg Glu Gly Pro Leu Pro Ala Ala Arg Pro
        1120                1125                1130 gct ggt gcc act ctg gaa agg ccc aag act ctc tcc cca ggg aag      3961
Ala Gly Ala Thr Leu Glu Arg Pro Lys Thr Leu Ser Pro Gly Lys
        1135                1140                1145 aat ggg gtc gtc aaa gac gtt ttt gcc ttt ggg ggt gcc gtg gag      4006
Asn Gly Val Val Lys Asp Val Phe Ala Phe Gly Gly Ala Val Glu
        1150                1155                1160 aac ccc gag tac ttg aca ccc cag gga gga gct gcc cct cag ccc      4051
Asn Pro Glu Tyr Leu Thr Pro Gln Gly Gly Ala Ala Pro Gln Pro
        1165                1170                1175 cac cct cct cct gcc ttc agc cca gcc ttc gac aac ctc tat tac      4096
His Pro Pro Pro Ala Phe Ser Pro Ala Phe Asp Asn Leu Tyr Tyr
        1180                1185                1190 tgg gac cag gac cca cca gag cgg ggg gct cca ccc agc acc ttc      4141
Trp Asp Gln Asp Pro Pro Glu Arg Gly Ala Pro Pro Ser Thr Phe
        1195                1200                1205 aaa ggg aca cct acg gca gag aac cca gag tac ctg ggt ctg gac      4186
Lys Gly Thr Pro Thr Ala Glu Asn Pro Glu Tyr Leu Gly Leu Asp
        1210                1215                1220 gtg cca gtg tga accagaaggc caagtccgca gaagccctga tgtgtcctca      4238
Val Pro Val
        1225 gggagcaggg aaggcctgac ttctgctggc atcaagaggt gggagggccc tccgaccact      4298 tccaggggaa cctgccatgc caggaacctg tcctaaggaa ccttccttcc tgcttgagtt      4358 cccagatggc tggaaggggt ccagcctcgt tggaagagga acagcactgg ggagtctttg      4418 tggattctga ggccctgccc aatgagactc tagggtccag tggatgccac agcccagctt      4478 ggcccttttcc ttccagatcc tgggtactga aagccttagg gaagctggcc tgagagggga      4538 agcggcccta agggagtgtc taagaacaaa agcgacccat tcagagactg tccctgaaac      4598 ctagtactgc cccccatgag gaaggaacag caatggtgtc agtatccagg ctttgtacag      4658 agtgcttttc tgtttagttt ttactttttt tgttttgttt tttaaagat gaaataaga      4718 cccaggggga gaatgggtgt tgtatgggga ggcaagtgtg gggggtcctt ctccacaccc      4778 actttgtcca tttgcaaata tattttggaa aacagcta      4816

<210> SEQ ID NO 8
<211> LENGTH: 1225
<212> TYPE: PRT
<213> ORGANISM: Homo sapiens

<400> SEQUENCE: 8
```

```
Met Lys Leu Arg Leu Pro Ala Ser Pro Glu Thr His Leu Asp Met Leu
1               5                   10                  15

Arg His Leu Tyr Gln Gly Cys Gln Val Val Gln Gly Asn Leu Glu Leu
            20                  25                  30

Thr Tyr Leu Pro Thr Asn Ala Ser Leu Ser Phe Leu Gln Asp Ile Gln
            35                  40                  45

Glu Val Gln Gly Tyr Val Leu Ile Ala His Asn Gln Val Arg Gln Val
        50                  55                  60

Pro Leu Gln Arg Leu Arg Ile Val Arg Gly Thr Gln Leu Phe Glu Asp
65                  70                  75                  80

Asn Tyr Ala Leu Ala Val Leu Asp Asn Gly Asp Pro Leu Asn Asn Thr
                85                  90                  95

Thr Pro Val Thr Gly Ala Ser Pro Gly Gly Leu Arg Glu Leu Gln Leu
            100                 105                 110

Arg Ser Leu Thr Glu Ile Leu Lys Gly Gly Val Leu Ile Gln Arg Asn
            115                 120                 125

Pro Gln Leu Cys Tyr Gln Asp Thr Ile Leu Trp Lys Asp Ile Phe His
        130                 135                 140

Lys Asn Asn Gln Leu Ala Leu Thr Leu Ile Asp Thr Asn Arg Ser Arg
145                 150                 155                 160

Ala Cys His Pro Cys Ser Pro Met Cys Lys Gly Ser Arg Cys Trp Gly
                165                 170                 175

Glu Ser Ser Glu Asp Cys Gln Ser Leu Thr Arg Thr Val Cys Ala Gly
            180                 185                 190

Gly Cys Ala Arg Cys Lys Gly Pro Leu Pro Thr Asp Cys Cys His Glu
        195                 200                 205

Gln Cys Ala Ala Gly Cys Thr Gly Pro Lys His Ser Asp Cys Leu Ala
    210                 215                 220

Cys Leu His Phe Asn His Ser Gly Ile Cys Glu Leu His Cys Pro Ala
225                 230                 235                 240

Leu Val Thr Tyr Asn Thr Asp Thr Phe Glu Ser Met Pro Asn Pro Glu
                245                 250                 255

Gly Arg Tyr Thr Phe Gly Ala Ser Cys Val Thr Ala Cys Pro Tyr Asn
            260                 265                 270

Tyr Leu Ser Thr Asp Val Gly Ser Cys Thr Leu Val Cys Pro Leu His
        275                 280                 285

Asn Gln Glu Val Thr Ala Glu Asp Gly Thr Gln Arg Cys Glu Lys Cys
    290                 295                 300

Ser Lys Pro Cys Ala Arg Val Cys Tyr Gly Leu Gly Met Glu His Leu
305                 310                 315                 320

Arg Glu Val Arg Ala Val Thr Ser Ala Asn Ile Gln Glu Phe Ala Gly
                325                 330                 335

Cys Lys Lys Ile Phe Gly Ser Leu Ala Phe Leu Pro Glu Ser Phe Asp
            340                 345                 350

Gly Asp Pro Ala Ser Asn Thr Ala Pro Leu Gln Pro Glu Gln Leu Gln
        355                 360                 365

Val Phe Glu Thr Leu Glu Glu Ile Thr Gly Tyr Leu Tyr Ile Ser Ala
    370                 375                 380

Trp Pro Asp Ser Leu Pro Asp Leu Ser Val Phe Gln Asn Leu Gln Val
385                 390                 395                 400

Ile Arg Gly Arg Ile Leu His Asn Gly Ala Tyr Ser Leu Thr Leu Gln
                405                 410                 415

Gly Leu Gly Ile Ser Trp Leu Gly Leu Arg Ser Leu Arg Glu Leu Gly
```

```
              420               425               430
    Ser Gly Leu Ala Leu Ile His His Asn Thr His Leu Cys Phe Val His
                    435               440               445
    Thr Val Pro Trp Asp Gln Leu Phe Arg Asn Pro His Gln Ala Leu Leu
            450               455               460
    His Thr Ala Asn Arg Pro Glu Asp Glu Cys Val Gly Glu Gly Leu Ala
    465               470               475               480
    Cys His Gln Leu Cys Ala Arg Gly His Cys Trp Gly Pro Gly Pro Thr
                        485               490               495
    Gln Cys Val Asn Cys Ser Gln Phe Leu Arg Gly Gln Glu Cys Val Glu
                    500               505               510
    Glu Cys Arg Val Leu Gln Gly Leu Pro Arg Glu Tyr Val Asn Ala Arg
                515               520               525
    His Cys Leu Pro Cys His Pro Glu Cys Gln Pro Gln Asn Gly Ser Val
                530               535               540
    Thr Cys Phe Gly Pro Glu Ala Asp Gln Cys Val Ala Cys Ala His Tyr
    545               550               555               560
    Lys Asp Pro Pro Phe Cys Val Ala Arg Cys Pro Ser Gly Val Lys Pro
                        565               570               575
    Asp Leu Ser Tyr Met Pro Ile Trp Lys Phe Pro Asp Glu Glu Gly Ala
                    580               585               590
    Cys Gln Pro Cys Pro Ile Asn Cys Thr His Ser Cys Val Asp Leu Asp
                595               600               605
    Asp Lys Gly Cys Pro Ala Glu Gln Arg Ala Ser Pro Leu Thr Ser Ile
                610               615               620
    Ile Ser Ala Val Val Gly Ile Leu Leu Val Val Val Leu Gly Val Val
    625               630               635               640
    Phe Gly Ile Leu Ile Lys Arg Arg Gln Gln Lys Ile Arg Lys Tyr Thr
                        645               650               655
    Met Arg Arg Leu Leu Gln Glu Thr Glu Leu Val Glu Pro Leu Thr Pro
                    660               665               670
    Ser Gly Ala Met Pro Asn Gln Ala Gln Met Arg Ile Leu Lys Glu Thr
                675               680               685
    Glu Leu Arg Lys Val Lys Val Leu Gly Ser Gly Ala Phe Gly Thr Val
                690               695               700
    Tyr Lys Gly Ile Trp Ile Pro Asp Gly Glu Asn Val Lys Ile Pro Val
    705               710               715               720
    Ala Ile Lys Val Leu Arg Glu Asn Thr Ser Pro Lys Ala Asn Lys Glu
                        725               730               735
    Ile Leu Asp Glu Ala Tyr Val Met Ala Gly Val Gly Ser Pro Tyr Val
                    740               745               750
    Ser Arg Leu Leu Gly Ile Cys Leu Thr Ser Thr Val Gln Leu Val Thr
                755               760               765
    Gln Leu Met Pro Tyr Gly Cys Leu Leu Asp His Val Arg Glu Asn Arg
                770               775               780
    Gly Arg Leu Gly Ser Gln Asp Leu Leu Asn Trp Cys Met Gln Ile Ala
    785               790               795               800
    Lys Gly Met Ser Tyr Leu Glu Asp Val Arg Leu Val His Arg Asp Leu
                        805               810               815
    Ala Ala Arg Asn Val Leu Val Lys Ser Pro Asn His Val Lys Ile Thr
                    820               825               830
    Asp Phe Gly Leu Ala Arg Leu Leu Asp Ile Asp Glu Thr Glu Tyr His
                835               840               845
```

-continued

Ala Asp Gly Gly Lys Val Pro Ile Lys Trp Met Ala Leu Glu Ser Ile
850                 855                 860

Leu Arg Arg Arg Phe Thr His Gln Ser Asp Val Trp Ser Tyr Gly Val
865                 870                 875                 880

Thr Val Trp Glu Leu Met Thr Phe Gly Ala Lys Pro Tyr Asp Gly Ile
            885                 890                 895

Pro Ala Arg Glu Ile Pro Asp Leu Leu Glu Lys Gly Glu Arg Leu Pro
            900                 905                 910

Gln Pro Pro Ile Cys Thr Ile Asp Val Tyr Met Ile Met Val Lys Cys
        915                 920                 925

Trp Met Ile Asp Ser Glu Cys Arg Pro Arg Phe Arg Glu Leu Val Ser
930                 935                 940

Glu Phe Ser Arg Met Ala Arg Asp Pro Gln Arg Phe Val Val Ile Gln
945                 950                 955                 960

Asn Glu Asp Leu Gly Pro Ala Ser Pro Leu Asp Ser Thr Phe Tyr Arg
                965                 970                 975

Ser Leu Leu Glu Asp Asp Asp Met Gly Asp Leu Val Asp Ala Glu Glu
            980                 985                 990

Tyr Leu Val Pro Gln Gln Gly Phe  Phe Cys Pro Asp Pro  Ala Pro Gly
            995                 1000                1005

Ala Gly  Gly Met Val His  His Arg His Arg Ser  Ser  Ser Thr Arg
    1010                1015                1020

Ser Gly  Gly Gly Asp Leu  Thr Leu Gly Leu Glu  Pro  Ser Glu Glu
    1025                1030                1035

Glu Ala  Pro Arg Ser Pro  Leu Ala Pro Ser Glu  Gly  Ala Gly Ser
    1040                1045                1050

Asp Val  Phe Asp Gly Asp  Leu Gly Met Gly Ala Ala  Lys Gly Leu
    1055                1060                1065

Gln Ser  Leu Pro Thr His  Asp Pro Ser Pro Leu Gln  Arg Tyr Ser
    1070                1075                1080

Glu Asp  Pro Thr Val Pro  Leu Pro Ser Glu Thr Asp  Gly Tyr Val
    1085                1090                1095

Ala Pro  Leu Thr Cys Ser  Pro Gln Pro Glu Tyr Val  Asn Gln Pro
    1100                1105                1110

Asp Val  Arg Pro Gln Pro  Pro Ser Pro Arg Glu Gly  Pro Leu Pro
    1115                1120                1125

Ala Ala  Arg Pro Ala Gly  Ala Thr Leu Glu Arg Pro  Lys Thr Leu
    1130                1135                1140

Ser Pro  Gly Lys Asn Gly  Val Val Lys Asp Val Phe  Ala Phe Gly
    1145                1150                1155

Gly Ala  Val Glu Asn Pro  Glu Tyr Leu Thr Pro Gln  Gly Gly Ala
    1160                1165                1170

Ala Pro  Gln Pro His Pro  Pro Pro Ala Phe Ser Pro  Ala Phe Asp
    1175                1180                1185

Asn Leu  Tyr Tyr Trp Asp  Gln Asp Pro Pro Glu Arg  Gly Ala Pro
    1190                1195                1200

Pro Ser  Thr Phe Lys Gly  Thr Pro Thr Ala Glu Asn  Pro Glu Tyr
    1205                1210                1215

Leu Gly  Leu Asp Val Pro  Val
    1220                1225

<210> SEQ ID NO 9
<211> LENGTH: 1321

<212> TYPE: DNA
<213> ORGANISM: Homo sapiens
<220> FEATURE:
<221> NAME/KEY: CDS
<222> LOCATION: (185)..(871)

<400> SEQUENCE: 9

```
cttttcccgg cacatgcgca ccgcagcggg tcgcgcgccc taaggagtgg cactttttaa      60
aagtgcagcc ggagaccagc ctacagccgc ctgcatctgt atccagcgcc aggtcccgcc     120
agtcccagct gcgcgcgccc cccagtcccg cacccgttcg gcccaggcta agttagccct     180 cacc atg ccg gtc aaa gga ggc acc aag tgc atc aaa tac ctg ctg ttc      229
     Met Pro Val Lys Gly Gly Thr Lys Cys Ile Lys Tyr Leu Leu Phe
     1               5                  10                  15 gga ttt aac ttc atc ttc tgg ctt gcc ggg att gct gtc ctt gcc att       277
Gly Phe Asn Phe Ile Phe Trp Leu Ala Gly Ile Ala Val Leu Ala Ile
                20                  25                  30 gga cta tgg ctc cga ttc gac tct cag acc aag agc atc ttc gag caa       325
Gly Leu Trp Leu Arg Phe Asp Ser Gln Thr Lys Ser Ile Phe Glu Gln
            35                  40                  45 gaa act aat aat aat aat tcc agc ttc tac aca gga gtc tat att ctg       373
Glu Thr Asn Asn Asn Asn Ser Ser Phe Tyr Thr Gly Val Tyr Ile Leu
        50                  55                  60 atc gga gcc ggc gcc ctc atg atg ctg gtg ggc ttc ctg ggc tgc tgc       421
Ile Gly Ala Gly Ala Leu Met Met Leu Val Gly Phe Leu Gly Cys Cys
65                  70                  75 ggg gct gtg cag gag tcc cag tgc atg ctg gga ctg ttc ttc ggc ttc       469
Gly Ala Val Gln Glu Ser Gln Cys Met Leu Gly Leu Phe Phe Gly Phe
80                  85                  90                  95 ctc ttg gtg ata ttc gcc att gaa ata gct gcg gcc atc tgg gga tat       517
Leu Leu Val Ile Phe Ala Ile Glu Ile Ala Ala Ala Ile Trp Gly Tyr
                100                 105                 110 tcc cac aag gat gag gtg att aag gaa gtc cag gag ttt tac aag gac       565
Ser His Lys Asp Glu Val Ile Lys Glu Val Gln Glu Phe Tyr Lys Asp
            115                 120                 125 acc tac aac aag ctg aaa acc aag gat gag ccc cag cgg gaa acg ctg       613
Thr Tyr Asn Lys Leu Lys Thr Lys Asp Glu Pro Gln Arg Glu Thr Leu
        130                 135                 140 aaa gcc atc cac tat gcg ttg aac tgc tgt ggt ttg gct ggg ggc gtg       661
Lys Ala Ile His Tyr Ala Leu Asn Cys Cys Gly Leu Ala Gly Gly Val
145                 150                 155 gaa cag ttt atc tca gac atc tgc ccc aag aag gac gta ctc gaa acc       709
Glu Gln Phe Ile Ser Asp Ile Cys Pro Lys Lys Asp Val Leu Glu Thr
160                 165                 170                 175 ttc acc gtg aag tcc tgt cct gat gcc atc aaa gag gtc ttc gac aat       757
Phe Thr Val Lys Ser Cys Pro Asp Ala Ile Lys Glu Val Phe Asp Asn
                180                 185                 190 aaa ttc cac atc atc ggc gca gtg ggc atc ggc att gcc gtg gtc atg       805
Lys Phe His Ile Ile Gly Ala Val Gly Ile Gly Ile Ala Val Val Met
            195                 200                 205 ata ttt ggc atg atc ttc agt atg atc ttg tgc tgt gct atc cgc agg       853
Ile Phe Gly Met Ile Phe Ser Met Ile Leu Cys Cys Ala Ile Arg Arg
        210                 215                 220 aac cgc gag atg gtc tag agtcagctta catccctgag caggaaagtt              901
Asn Arg Glu Met Val
            225 tacccatgaa gattggtggg atttttttgtt tgtttgtttt gttttgtttg ttgtttgttg    961 tttgttttt tgccactaat tttagtattc attctgcatt gctagataaa agctgaagtt     1021 actttatgtt tgtcttttaa tgcttcattc aatattgaca tttgtagttg agcgggggt     1081
```

```
ttggtttgct ttggtttata tttttttcagt tgtttgtttt tgcttgttat attaagcaga    1141
aatcctgcaa tgaaaggtac tatatttgct agactctaga caagatattg tacataaaag    1201
aatttttttg tctttaaata gatacaaatg tctatcaact ttaatcaagt tgtaacttat    1261
attgaagaca atttgataca taataaaaaa ttatgacaat gtcctggact ggtaaaaaaa    1321
```

```
<210> SEQ ID NO 10
<211> LENGTH: 228
<212> TYPE: PRT
<213> ORGANISM: Homo sapiens

<400> SEQUENCE: 10
```

```
Met Pro Val Lys Gly Gly Thr Lys Cys Ile Lys Tyr Leu Leu Phe Gly
 1               5                  10                  15

Phe Asn Phe Ile Phe Trp Leu Ala Gly Ile Ala Val Leu Ala Ile Gly
            20                  25                  30

Leu Trp Leu Arg Phe Asp Ser Gln Thr Lys Ser Ile Phe Glu Gln Glu
        35                  40                  45

Thr Asn Asn Asn Asn Ser Ser Phe Tyr Thr Gly Val Tyr Ile Leu Ile
    50                  55                  60

Gly Ala Gly Ala Leu Met Met Leu Val Gly Phe Leu Gly Cys Cys Gly
65                  70                  75                  80

Ala Val Gln Glu Ser Gln Cys Met Leu Gly Leu Phe Phe Gly Phe Leu
                85                  90                  95

Leu Val Ile Phe Ala Ile Glu Ile Ala Ala Ala Ile Trp Gly Tyr Ser
            100                 105                 110

His Lys Asp Glu Val Ile Lys Glu Val Gln Glu Phe Tyr Lys Asp Thr
        115                 120                 125

Tyr Asn Lys Leu Lys Thr Lys Asp Glu Pro Gln Arg Glu Thr Leu Lys
    130                 135                 140

Ala Ile His Tyr Ala Leu Asn Cys Cys Gly Leu Ala Gly Gly Val Glu
145                 150                 155                 160

Gln Phe Ile Ser Asp Ile Cys Pro Lys Lys Asp Val Leu Glu Thr Phe
                165                 170                 175

Thr Val Lys Ser Cys Pro Asp Ala Ile Lys Glu Val Phe Asp Asn Lys
            180                 185                 190

Phe His Ile Ile Gly Ala Val Gly Ile Gly Ile Ala Val Val Met Ile
        195                 200                 205

Phe Gly Met Ile Phe Ser Met Ile Leu Cys Cys Ala Ile Arg Arg Asn
    210                 215                 220

Arg Glu Met Val
225
```

```
<210> SEQ ID NO 11
<211> LENGTH: 4267
<212> TYPE: DNA
<213> ORGANISM: Homo sapiens
<220> FEATURE:
<221> NAME/KEY: CDS
<222> LOCATION: (69)..(3218)

<400> SEQUENCE: 11
```

```
attcgcctct gggaggttta ggaagcggct ccgggtcggt ggccccagga cagggaagag    60 cgggcgct atg ggg agc cgg acg cca gag tcc cct ctc cac gcc gtg cag    110
         Met Gly Ser Arg Thr Pro Glu Ser Pro Leu His Ala Val Gln
          1               5                  10
```

-continued

| | |
|---|---|
| ctg cgc tgg ggc ccc cgg cgc cga ccc ccg ctg ctg ccg ctg ctg ttg<br>Leu Arg Trp Gly Pro Arg Arg Arg Pro Pro Leu Leu Pro Leu Leu Leu<br>15                  20                       25                 30 | 158 |
| ctg ctg ctg ccg ccg cca ccc agg gtc ggg ggc ttc aac tta gac gcg<br>Leu Leu Leu Pro Pro Pro Pro Arg Val Gly Gly Phe Asn Leu Asp Ala<br>35                   40                       45 | 206 |
| gag gcc cca gca gta ctc tcg ggc ccg ggc tcc ttc ttc gga ttc<br>Glu Ala Pro Ala Val Leu Ser Gly Pro Gly Ser Phe Phe Gly Phe<br>50                 55                   60 | 254 |
| tca gtg gag ttt tac cgg ccg gga aca gac ggg gtc agt gtg ctg gtg<br>Ser Val Glu Phe Tyr Arg Pro Gly Thr Asp Gly Val Ser Val Leu Val<br>65                  70                    75 | 302 |
| gga gca ccc aag gct aat acc agc cag cca gga gtg ctg cag ggt ggt<br>Gly Ala Pro Lys Ala Asn Thr Ser Gln Pro Gly Val Leu Gln Gly Gly<br>80                    85                    90 | 350 |
| gct gtc tac ctc tgt cct tgg ggt gcc agc ccc aca cag tgc acc ccc<br>Ala Val Tyr Leu Cys Pro Trp Gly Ala Ser Pro Thr Gln Cys Thr Pro<br>95                  100                105              110 | 398 |
| att gaa ttt gac agc aaa ggc tct cgg ctc ctg gag tcc tca ctg tcc<br>Ile Glu Phe Asp Ser Lys Gly Ser Arg Leu Leu Glu Ser Ser Leu Ser<br>              115                120              125 | 446 |
| agc tca gag gga gag gag cct gtg gag tac aag tcc ttg cag tgg ttc<br>Ser Ser Glu Gly Glu Glu Pro Val Glu Tyr Lys Ser Leu Gln Trp Phe<br>130                  135              140 | 494 |
| ggg gca aca gtt cga gcc cat ggc tcc tcc atc ttg gca tgc gct cca<br>Gly Ala Thr Val Arg Ala His Gly Ser Ser Ile Leu Ala Cys Ala Pro<br>            145                150              155 | 542 |
| ctg tac agc tgg cgc aca gag aag gag cca ctg agc gac ccc gtg ggc<br>Leu Tyr Ser Trp Arg Thr Glu Lys Glu Pro Leu Ser Asp Pro Val Gly<br>160                  165              170 | 590 |
| acc tgc tac ctc tcc aca gat aac ttc acc cga att ctg gag tat gca<br>Thr Cys Tyr Leu Ser Thr Asp Asn Phe Thr Arg Ile Leu Glu Tyr Ala<br>175                  180              185              190 | 638 |
| ccc tgc cgc tca gat ttc agc tgg gca gca gga cag ggt tac tgc caa<br>Pro Cys Arg Ser Asp Phe Ser Trp Ala Ala Gly Gln Gly Tyr Cys Gln<br>            195                200              205 | 686 |
| gga ggc ttc agt gcc gag ttc acc aag act ggc cgt gtg gtt tta ggt<br>Gly Gly Phe Ser Ala Glu Phe Thr Lys Thr Gly Arg Val Val Leu Gly<br>210                  215              220 | 734 |
| gga cca gga agc tat ttc tgg caa ggc cag atc ctg tct gcc act cag<br>Gly Pro Gly Ser Tyr Phe Trp Gln Gly Gln Ile Leu Ser Ala Thr Gln<br>            225                230              235 | 782 |
| gag cag att gca gaa tct tat tac ccc gag tac ctg atc aac ctg gtt<br>Glu Gln Ile Ala Glu Ser Tyr Tyr Pro Glu Tyr Leu Ile Asn Leu Val<br>240                  245              250 | 830 |
| cag ggg cag ctg cag act cgc cag gcc agt tcc atc tat gat gac agc<br>Gln Gly Gln Leu Gln Thr Arg Gln Ala Ser Ser Ile Tyr Asp Asp Ser<br>255                  260              265              270 | 878 |
| tac cta gga tac tct gtg gct gtt ggt gaa ttc agt ggt gat gac aca<br>Tyr Leu Gly Tyr Ser Val Ala Val Gly Glu Phe Ser Gly Asp Asp Thr<br>            275                280              285 | 926 |
| gaa gac ttt gtt gct ggt gtg ccc aaa ggg aac ctc act tac ggc tat<br>Glu Asp Phe Val Ala Gly Val Pro Lys Gly Asn Leu Thr Tyr Gly Tyr<br>290                  295              300 | 974 |
| gtc acc atc ctt aat ggc tca gac att cga tcc ctc tac aac ttc tca<br>Val Thr Ile Leu Asn Gly Ser Asp Ile Arg Ser Leu Tyr Asn Phe Ser<br>305                  310              315 | 1022 |
| ggg gaa cag atg gcc tcc tac ttt ggc tat gca gtg gcc gcc aca gac<br>Gly Glu Gln Met Ala Ser Tyr Phe Gly Tyr Ala Val Ala Ala Thr Asp<br>320                  325              330 | 1070 |

-continued

```
gtc aat ggg gac ggg ctg gat gac ttg ctg gtg ggg gca ccc ctg ctc    1118
Val Asn Gly Asp Gly Leu Asp Asp Leu Leu Val Gly Ala Pro Leu Leu
335                 340                 345                 350 atg gat cgg acc cct gac ggg cgg cct cag gag gtg ggc agg gtc tac    1166
Met Asp Arg Thr Pro Asp Gly Arg Pro Gln Glu Val Gly Arg Val Tyr
            355                 360                 365 gtc tac ctg cag cac cca gcc ggc ata gag ccc acg ccc acc ctt acc    1214
Val Tyr Leu Gln His Pro Ala Gly Ile Glu Pro Thr Pro Thr Leu Thr
370                 375                 380 ctc act ggc cat gat gag ttt ggc cga ttt ggc agc tcc ttg acc ccc    1262
Leu Thr Gly His Asp Glu Phe Gly Arg Phe Gly Ser Ser Leu Thr Pro
            385                 390                 395 ctg ggg gac ctg gac cag gat ggc tac aat gat gtg gcc atc ggg gct    1310
Leu Gly Asp Leu Asp Gln Asp Gly Tyr Asn Asp Val Ala Ile Gly Ala
400                 405                 410 ccc ttt ggt ggg gag acc cag cag gga gta gtg ttt gta ttt cct ggg    1358
Pro Phe Gly Gly Glu Thr Gln Gln Gly Val Val Phe Val Phe Pro Gly
415                 420                 425                 430 ggc cca gga ggg ctg ggc tct aag cct tcc cag gtt ctg cag ccc ctg    1406
Gly Pro Gly Gly Leu Gly Ser Lys Pro Ser Gln Val Leu Gln Pro Leu
            435                 440                 445 tgg gca gcc agc cac acc cca gac ttc ttt ggc tct gcc ctt cga gga    1454
Trp Ala Ala Ser His Thr Pro Asp Phe Phe Gly Ser Ala Leu Arg Gly
            450                 455                 460 ggc cga gac ctg gat ggc aat gga tat cct gat ctg att gtg ggg tcc    1502
Gly Arg Asp Leu Asp Gly Asn Gly Tyr Pro Asp Leu Ile Val Gly Ser
465                 470                 475 ttt ggt gtg gac aag gct gtg gta tac agg ggc cgc ccc atc gtg tcc    1550
Phe Gly Val Asp Lys Ala Val Val Tyr Arg Gly Arg Pro Ile Val Ser
            480                 485                 490 gct agt gcc tcc ctc acc atc ttc ccc gcc atg ttc aac cca gag gag    1598
Ala Ser Ala Ser Leu Thr Ile Phe Pro Ala Met Phe Asn Pro Glu Glu
495                 500                 505                 510 cgg agc tgc agc tta gag ggg aac cct gtg gcc tgc atc aac ctt agc    1646
Arg Ser Cys Ser Leu Glu Gly Asn Pro Val Ala Cys Ile Asn Leu Ser
            515                 520                 525 ttc tgc ctc aat gct tct gga aaa cac gtt gct gac tcc att ggt ttc    1694
Phe Cys Leu Asn Ala Ser Gly Lys His Val Ala Asp Ser Ile Gly Phe
            530                 535                 540 aca gtg gaa ctt cag ctg gac tgg cag aag cag aag gga ggg gta cgg    1742
Thr Val Glu Leu Gln Leu Asp Trp Gln Lys Gln Lys Gly Gly Val Arg
            545                 550                 555 cgg gca ctg ttc ctg gcc tcc agg cag gca acc ctg acc cag acc ctg    1790
Arg Ala Leu Phe Leu Ala Ser Arg Gln Ala Thr Leu Thr Gln Thr Leu
560                 565                 570 ctc atc cag aat ggg gct cga gag gat tgc aga gag atg aag atc tac    1838
Leu Ile Gln Asn Gly Ala Arg Glu Asp Cys Arg Glu Met Lys Ile Tyr
575                 580                 585                 590 ctc agg aac gag tca gaa ttt cga gac aaa ctc tcg ccg att cac atc    1886
Leu Arg Asn Glu Ser Glu Phe Arg Asp Lys Leu Ser Pro Ile His Ile
            595                 600                 605 gct ctc aac ttc tcc ttg gac ccc caa gcc cca gtg gac agc cac ggc    1934
Ala Leu Asn Phe Ser Leu Asp Pro Gln Ala Pro Val Asp Ser His Gly
            610                 615                 620 ctc agg cca gcc cta cat tat cag agc aag agc cgg ata gag gac aag    1982
Leu Arg Pro Ala Leu His Tyr Gln Ser Lys Ser Arg Ile Glu Asp Lys
            625                 630                 635 gct cag atc ttg ctg gac tgt gga gaa gac aac atc tgt gtg cct gac    2030
Ala Gln Ile Leu Leu Asp Cys Gly Glu Asp Asn Ile Cys Val Pro Asp
```

```
ctg cag ctg gaa gtg ttt ggg gag cag aac cat gtg tac ctg ggt gac       2078
Leu Gln Leu Glu Val Phe Gly Glu Gln Asn His Val Tyr Leu Gly Asp
655                 660                 665                 670 aag aat gcc ctg aac ctc act ttc cat gcc cag aat gtg ggt gag ggt       2126
Lys Asn Ala Leu Asn Leu Thr Phe His Ala Gln Asn Val Gly Glu Gly
            675                 680                 685 ggc gcc tat gag gct gag ctt cgg gtc acc gcc cct cca gag gct gag       2174
Gly Ala Tyr Glu Ala Glu Leu Arg Val Thr Ala Pro Pro Glu Ala Glu
        690                 695                 700 tac tca gga ctc gtc aga cac cca ggg aac ttc tcc agc ctg agc tgt       2222
Tyr Ser Gly Leu Val Arg His Pro Gly Asn Phe Ser Ser Leu Ser Cys
    705                 710                 715 gac tac ttt gcc gtg aac cag agc cgc ctg ctg gtg tgt gac ctg ggc       2270
Asp Tyr Phe Ala Val Asn Gln Ser Arg Leu Leu Val Cys Asp Leu Gly
720                 725                 730 aac ccc atg aag gca gga gcc agt ctg tgg ggt ggc ctt cgg ttt aca       2318
Asn Pro Met Lys Ala Gly Ala Ser Leu Trp Gly Gly Leu Arg Phe Thr
735                 740                 745                 750 gtc cct cat ctc cgg gac act aag aaa acc atc cag ttt gac ttc cag       2366
Val Pro His Leu Arg Asp Thr Lys Lys Thr Ile Gln Phe Asp Phe Gln
            755                 760                 765 atc ctc agc aag aat ctc aac aac tcg caa agc gac gtg gtt tcc ttt       2414
Ile Leu Ser Lys Asn Leu Asn Asn Ser Gln Ser Asp Val Val Ser Phe
        770                 775                 780 cgg ctc tcc gtg gag gct cag gcc cag gtc acc ctg aac ggt gtc tcc       2462
Arg Leu Ser Val Glu Ala Gln Ala Gln Val Thr Leu Asn Gly Val Ser
    785                 790                 795 aag cct gag gca gtg cta ttc cca gta agc gac tgg cat ccc cga gac       2510
Lys Pro Glu Ala Val Leu Phe Pro Val Ser Asp Trp His Pro Arg Asp
800                 805                 810 cag cct cag aag gag gag gac ctg gga cct gct gtc cac cat gtc tat       2558
Gln Pro Gln Lys Glu Glu Asp Leu Gly Pro Ala Val His His Val Tyr
815                 820                 825                 830 gag ctc atc aac caa ggc ccc agc tcc att agc cag ggt gtg ctg gaa       2606
Glu Leu Ile Asn Gln Gly Pro Ser Ser Ile Ser Gln Gly Val Leu Glu
            835                 840                 845 ctc agc tgt ccc cag gct ctg gaa ggt cag cag ctc cta tat gtg acc       2654
Leu Ser Cys Pro Gln Ala Leu Glu Gly Gln Gln Leu Leu Tyr Val Thr
        850                 855                 860 aga gtt acg gga ctc aac tgc acc acc aat cac ccc att aac cca aag       2702
Arg Val Thr Gly Leu Asn Cys Thr Thr Asn His Pro Ile Asn Pro Lys
    865                 870                 875 ggc ctg gag ttg gat ccc gag ggt tcc ctg cac cac cag caa aaa cgg       2750
Gly Leu Glu Leu Asp Pro Glu Gly Ser Leu His His Gln Gln Lys Arg
880                 885                 890 gaa gct cca agc cgc agc tct gct tcc tcg gga cct cag atc ctg aaa       2798
Glu Ala Pro Ser Arg Ser Ser Ala Ser Ser Gly Pro Gln Ile Leu Lys
895                 900                 905                 910 tgc ccg gag gct gag tgt ttc agg ctg cgc tgt gag ctc ggg ccc ctg       2846
Cys Pro Glu Ala Glu Cys Phe Arg Leu Arg Cys Glu Leu Gly Pro Leu
            915                 920                 925 cac caa caa gag agc caa agt ctg cag ttg cat ttc cga gtc tgg gcc       2894
His Gln Gln Glu Ser Gln Ser Leu Gln Leu His Phe Arg Val Trp Ala
        930                 935                 940 aag act ttc ttg cag cgg gag cac cag cca ttt agc ctg cag tgt gag       2942
Lys Thr Phe Leu Gln Arg Glu His Gln Pro Phe Ser Leu Gln Cys Glu
945                 950                 955 gct gtg tac aaa gcc ctg aag atg ccc tac cga atc ctg cct cgg cag       2990
Ala Val Tyr Lys Ala Leu Lys Met Pro Tyr Arg Ile Leu Pro Arg Gln
```

```
Ala Val Tyr Lys Ala Leu Lys Met Pro Tyr Arg Ile Leu Pro Arg Gln
    960                 965                 970 ctg ccc caa aaa gag cgt cag gtg gcc aca gct gtg caa tgg acc aag         3038
Leu Pro Gln Lys Glu Arg Gln Val Ala Thr Ala Val Gln Trp Thr Lys
975                 980                 985                 990 gca gaa ggc agc tat ggc gtc cca ctg tgg atc atc atc cta gcc atc         3086
Ala Glu Gly Ser Tyr Gly Val Pro Leu Trp Ile Ile Ile Leu Ala Ile
                    995                 1000                1005 ctg ttt ggc ctc ctg ctc cta ggt cta ctc atc tac atc ctc tac             3131
Leu Phe Gly Leu Leu Leu Leu Gly Leu Leu Ile Tyr Ile Leu Tyr
        1010                1015                1020 aag ctt gga ttc ttc aaa cgc tcc ctc cca tat ggc acc gcc atg             3176
Lys Leu Gly Phe Phe Lys Arg Ser Leu Pro Tyr Gly Thr Ala Met
        1025                1030                1035 gaa aaa gct cag ctc aag cct cca gcc acc tct gat gcc tga                 3218
Glu Lys Ala Gln Leu Lys Pro Pro Ala Thr Ser Asp Ala
        1040                1045 gtcctcccaa tttcagactc ccattcctga agaaccagtc cccccaccct cattctactg       3278
aaaaggaggg gtctgggtac ttcttgaagg tgctgacggc agggagaag ctcctctccc        3338 cagcccagag acatacttga agggccagag ccagggggt gaggagctgg ggatccctcc        3398
cccccatgca ctgtgaagga cccttgttta cacatacccct cttcatggat ggggaactc      3458 agatccaggg acagaggccc cagcctccct gaagcctttg catttggag agttcctga        3518 aacaacttgg aaagataact aggaaatcca ttcacagttc tttgggccag acatgccaca       3578
aggacttcct gtccagctcc aacctgcaaa gatctgtcct cagccttgcc agagatccaa       3638
aagaagcccc cagctaagaa cctggaactt ggggagttaa gacctggcag ctctggacag       3698
ccccaccctg gtgggccaac aaagaacact aactatgcat ggtgcccag gaccagctca       3758 ggacagatgc cacacaagga tagatgctgg cccagggccc agagcccagc tcaaggga       3818 atcagaactc aaatgggccc agatccagcc tggggtctgg agttgatctg gaacccagac      3878
tcagacattg gcacctaatc caggcagatc caggactata tttgggcctg ctccagacct      3938
gatcctggag gcccagttca ccctgattta ggagaagcca ggaatttccc aggacccttga     3998 aggggccatg atggcaacag atctggaacc tcagcctggc cagacacagg ccctccctgt      4058
tccccagaga aagggagcc cactgtcctg ggcctgcaga atttggttc tgcctgccag        4118 ctgcactgat gctgccctc atctctctgc ccaacccttc cctcacttgg caccagaca       4178 cccaggactt atttaaactc tgttgcaagt gcaataaatc tgacccagtg ccccactga       4238 ccagaactag aaaaaaaaaa aaaaaaaaa                                         4267

<210> SEQ ID NO 12
<211> LENGTH: 1049
<212> TYPE: PRT
<213> ORGANISM: Homo sapiens

<400> SEQUENCE: 12

Met Gly Ser Arg Thr Pro Glu Ser Pro Leu His Ala Val Gln Leu Arg
1               5                   10                  15

Trp Gly Pro Arg Arg Pro Pro Leu Leu Pro Leu Leu Leu Leu Leu
            20                  25                  30

Leu Pro Pro Pro Arg Val Gly Gly Phe Asn Leu Asp Ala Glu Ala
        35                  40                  45

Pro Ala Val Leu Ser Gly Pro Pro Gly Ser Phe Phe Gly Phe Ser Val
    50                  55                  60
```

```
Glu Phe Tyr Arg Pro Gly Thr Asp Gly Val Ser Val Leu Val Gly Ala
 65                  70                  75                  80

Pro Lys Ala Asn Thr Ser Gln Pro Gly Val Leu Gln Gly Gly Ala Val
                 85                  90                  95

Tyr Leu Cys Pro Trp Gly Ala Ser Pro Thr Gln Cys Thr Pro Ile Glu
            100                 105                 110

Phe Asp Ser Lys Gly Ser Arg Leu Leu Glu Ser Ser Leu Ser Ser Ser
        115                 120                 125

Glu Gly Glu Glu Pro Val Glu Tyr Lys Ser Leu Gln Trp Phe Gly Ala
    130                 135                 140

Thr Val Arg Ala His Gly Ser Ser Ile Leu Ala Cys Ala Pro Leu Tyr
145                 150                 155                 160

Ser Trp Arg Thr Glu Lys Glu Pro Leu Ser Asp Pro Val Gly Thr Cys
                165                 170                 175

Tyr Leu Ser Thr Asp Asn Phe Thr Arg Ile Leu Glu Tyr Ala Pro Cys
            180                 185                 190

Arg Ser Asp Phe Ser Trp Ala Ala Gly Gln Gly Tyr Cys Gln Gly Gly
        195                 200                 205

Phe Ser Ala Glu Phe Thr Lys Thr Gly Arg Val Val Leu Gly Gly Pro
210                 215                 220

Gly Ser Tyr Phe Trp Gln Gly Gln Ile Leu Ser Ala Thr Gln Glu Gln
225                 230                 235                 240

Ile Ala Glu Ser Tyr Tyr Pro Glu Tyr Leu Ile Asn Leu Val Gln Gly
                245                 250                 255

Gln Leu Gln Thr Arg Gln Ala Ser Ser Ile Tyr Asp Asp Ser Tyr Leu
            260                 265                 270

Gly Tyr Ser Val Ala Val Gly Glu Phe Ser Gly Asp Asp Thr Glu Asp
        275                 280                 285

Phe Val Ala Gly Val Pro Lys Gly Asn Leu Thr Tyr Gly Tyr Val Thr
290                 295                 300

Ile Leu Asn Gly Ser Asp Ile Arg Ser Leu Tyr Asn Phe Ser Gly Glu
305                 310                 315                 320

Gln Met Ala Ser Tyr Phe Gly Tyr Ala Val Ala Ala Thr Asp Val Asn
                325                 330                 335

Gly Asp Gly Leu Asp Asp Leu Leu Val Gly Ala Pro Leu Leu Met Asp
            340                 345                 350

Arg Thr Pro Asp Gly Arg Pro Gln Glu Val Gly Arg Val Tyr Val Tyr
        355                 360                 365

Leu Gln His Pro Ala Gly Ile Glu Pro Thr Pro Thr Leu Thr Leu Thr
370                 375                 380

Gly His Asp Glu Phe Gly Arg Phe Gly Ser Ser Leu Thr Pro Leu Gly
385                 390                 395                 400

Asp Leu Asp Gln Asp Gly Tyr Asn Asp Val Ala Ile Gly Ala Pro Phe
                405                 410                 415

Gly Gly Glu Thr Gln Gln Gly Val Val Phe Val Phe Pro Gly Gly Pro
            420                 425                 430

Gly Gly Leu Gly Ser Lys Pro Ser Gln Val Leu Gln Pro Leu Trp Ala
        435                 440                 445

Ala Ser His Thr Pro Asp Phe Phe Gly Ser Ala Leu Arg Gly Gly Arg
450                 455                 460

Asp Leu Asp Gly Asn Gly Tyr Pro Asp Leu Ile Val Gly Ser Phe Gly
465                 470                 475                 480

Val Asp Lys Ala Val Val Tyr Arg Gly Arg Pro Ile Val Ser Ala Ser
```

```
                    485                 490                 495
Ala Ser Leu Thr Ile Phe Pro Ala Met Phe Asn Pro Glu Glu Arg Ser
                500                 505                 510

Cys Ser Leu Glu Gly Asn Pro Val Ala Cys Ile Asn Leu Ser Phe Cys
                515                 520                 525

Leu Asn Ala Ser Gly Lys His Val Ala Asp Ser Ile Gly Phe Thr Val
                530                 535                 540

Glu Leu Gln Leu Asp Trp Gln Lys Gln Lys Gly Gly Val Arg Arg Ala
545                 550                 555                 560

Leu Phe Leu Ala Ser Arg Gln Ala Thr Leu Thr Gln Thr Leu Leu Ile
                565                 570                 575

Gln Asn Gly Ala Arg Glu Asp Cys Arg Glu Met Lys Ile Tyr Leu Arg
                580                 585                 590

Asn Glu Ser Glu Phe Arg Asp Lys Leu Ser Pro Ile His Ile Ala Leu
                595                 600                 605

Asn Phe Ser Leu Asp Pro Gln Ala Pro Val Asp Ser His Gly Leu Arg
                610                 615                 620

Pro Ala Leu His Tyr Gln Ser Lys Ser Arg Ile Glu Asp Lys Ala Gln
625                 630                 635                 640

Ile Leu Leu Asp Cys Gly Glu Asp Asn Ile Cys Val Pro Asp Leu Gln
                645                 650                 655

Leu Glu Val Phe Gly Glu Gln Asn His Val Tyr Leu Gly Asp Lys Asn
                660                 665                 670

Ala Leu Asn Leu Thr Phe His Ala Gln Asn Val Gly Glu Gly Gly Ala
                675                 680                 685

Tyr Glu Ala Glu Leu Arg Val Thr Ala Pro Pro Glu Ala Glu Tyr Ser
690                 695                 700

Gly Leu Val Arg His Pro Gly Asn Phe Ser Ser Leu Ser Cys Asp Tyr
705                 710                 715                 720

Phe Ala Val Asn Gln Ser Arg Leu Leu Val Cys Asp Leu Gly Asn Pro
                725                 730                 735

Met Lys Ala Gly Ala Ser Leu Trp Gly Gly Leu Arg Phe Thr Val Pro
                740                 745                 750

His Leu Arg Asp Thr Lys Lys Thr Ile Gln Phe Asp Phe Gln Ile Leu
                755                 760                 765

Ser Lys Asn Leu Asn Asn Ser Gln Ser Asp Val Val Ser Phe Arg Leu
                770                 775                 780

Ser Val Glu Ala Gln Ala Gln Val Thr Leu Asn Gly Val Ser Lys Pro
785                 790                 795                 800

Glu Ala Val Leu Phe Pro Val Ser Asp Trp His Pro Arg Asp Gln Pro
                805                 810                 815

Gln Lys Glu Glu Asp Leu Gly Pro Ala Val His His Val Tyr Glu Leu
                820                 825                 830

Ile Asn Gln Gly Pro Ser Ser Ile Ser Gln Gly Val Leu Glu Leu Ser
                835                 840                 845

Cys Pro Gln Ala Leu Glu Gly Gln Gln Leu Leu Tyr Val Thr Arg Val
                850                 855                 860

Thr Gly Leu Asn Cys Thr Thr Asn His Pro Ile Asn Pro Lys Gly Leu
865                 870                 875                 880

Glu Leu Asp Pro Glu Gly Ser Leu His His Gln Gln Lys Arg Glu Ala
                885                 890                 895

Pro Ser Arg Ser Ser Ala Ser Ser Gly Pro Gln Ile Leu Lys Cys Pro
                900                 905                 910
```

```
Glu Ala Glu Cys Phe Arg Leu Arg Cys Glu Leu Gly Pro Leu His Gln
            915                 920                 925

Gln Glu Ser Gln Ser Leu Gln Leu His Phe Arg Val Trp Ala Lys Thr
    930                 935                 940

Phe Leu Gln Arg Glu His Gln Pro Phe Ser Leu Gln Cys Glu Ala Val
945                 950                 955                 960

Tyr Lys Ala Leu Lys Met Pro Tyr Arg Ile Leu Pro Arg Gln Leu Pro
            965                 970                 975

Gln Lys Glu Arg Gln Val Ala Thr Ala Val Gln Trp Thr Lys Ala Glu
        980                 985                 990

Gly Ser Tyr Gly Val Pro Leu Trp Ile Ile Ile Leu Ala Ile Leu Phe
        995                 1000                1005

Gly Leu Leu Leu Leu Gly Leu Leu Ile Tyr Ile Leu Tyr Lys Leu
    1010                1015                1020

Gly Phe Phe Lys Arg Ser Leu Pro Tyr Gly Thr Ala Met Glu Lys
    1025                1030                1035

Ala Gln Leu Lys Pro Pro Ala Thr Ser Asp Ala
    1040                1045

<210> SEQ ID NO 13
<211> LENGTH: 5748
<212> TYPE: DNA
<213> ORGANISM: Homo sapiens
<220> FEATURE:
<221> NAME/KEY: CDS
<222> LOCATION: (435)..(2663)

<400> SEQUENCE: 13
gagaagaaag ccagtgcgtc tctgggcgca ggggccagtg gggctcggag gcacaggcac    60
cccgcgacac tccaggttcc ccgacccacg tccctggcag ccccgattat ttacagcctc   120
agcagagcac ggggcggggg cagaggggcc cgcccgggag ggctgctact tcttaaaacc   180
tctgcgggct gcttagtcac agccccccctt gcttgggtgt gtccttcgct cgctccctcc   240
ctccgtctta ggtcactgtt ttcaacctcg aataaaaact gcagccaact tccgaggcag   300
cctcattgcc cagcggaccc cagcctctgc caggttcggt ccgccatcct cgtcccgtcc   360
tccgccggcc cctgccccgc gcccagggat cctccagctc ctttcgcccg cgccctccgt   420
tcgctccgga cacc atg gac aag ttt tgg tgg cac gca gcc tgg gga ctc   470
              Met Asp Lys Phe Trp Trp His Ala Ala Trp Gly Leu
                1               5                  10 tgc ctc gtg ccg ctg agc ctg gcg cag atc gat ttg aat ata acc tgc   518
Cys Leu Val Pro Leu Ser Leu Ala Gln Ile Asp Leu Asn Ile Thr Cys
         15                  20                  25 cgc ttt gca ggt gta ttc cac gtg gag aaa aat ggt cgc tac agc atc   566
Arg Phe Ala Gly Val Phe His Val Glu Lys Asn Gly Arg Tyr Ser Ile
     30                  35                  40 tct cgg acg gag gcc gct gac ctc tgc aag gct ttc aat agc acc ttg   614
Ser Arg Thr Glu Ala Ala Asp Leu Cys Lys Ala Phe Asn Ser Thr Leu
 45                  50                  55                  60 ccc aca atg gcc cag atg gag aaa gct ctg agc atc gga ttt gag acc   662
Pro Thr Met Ala Gln Met Glu Lys Ala Leu Ser Ile Gly Phe Glu Thr
                 65                  70                  75 tgc agg tat ggg ttc ata gaa ggg cac gtg gtg att ccc cgg atc cac   710
Cys Arg Tyr Gly Phe Ile Glu Gly His Val Val Ile Pro Arg Ile His
             80                  85                  90 ccc aac tcc atc tgt gca gca aac aac aca ggg gtg tac atc ctc aca   758
Pro Asn Ser Ile Cys Ala Ala Asn Asn Thr Gly Val Tyr Ile Leu Thr
```

-continued

```
                95                  100                 105
tcc aac acc tcc cag tat gac aca tat tgc ttc aat gct tca gct cca      806
Ser Asn Thr Ser Gln Tyr Asp Thr Tyr Cys Phe Asn Ala Ser Ala Pro
    110                 115                 120 cct gaa gaa gat tgt aca tca gtc aca gac ctg ccc aat gcc ttt gat      854
Pro Glu Glu Asp Cys Thr Ser Val Thr Asp Leu Pro Asn Ala Phe Asp
125                 130                 135                 140 gga cca att acc ata act att gtt aac cgt gat ggc acc cgc tat gtc      902
Gly Pro Ile Thr Ile Thr Ile Val Asn Arg Asp Gly Thr Arg Tyr Val
                145                 150                 155 cag aaa gga gaa tac aga acg aat cct gaa gac atc tac ccc agc aac      950
Gln Lys Gly Glu Tyr Arg Thr Asn Pro Glu Asp Ile Tyr Pro Ser Asn
            160                 165                 170 cct act gat gat gac gtg agc agc ggc tcc tcc agt gaa agg agc agc      998
Pro Thr Asp Asp Asp Val Ser Ser Gly Ser Ser Ser Glu Arg Ser Ser
        175                 180                 185 act tca gga ggt tac atc ttt tac acc ttt tct act gta cac ccc atc     1046
Thr Ser Gly Gly Tyr Ile Phe Tyr Thr Phe Ser Thr Val His Pro Ile
    190                 195                 200 cca gac gaa gac agt ccc tgg atc acc gac agc aca gac aga atc cct     1094
Pro Asp Glu Asp Ser Pro Trp Ile Thr Asp Ser Thr Asp Arg Ile Pro
205                 210                 215                 220 gct acc act ttg atg agc act agt gct aca gca act gag aca gca acc     1142
Ala Thr Thr Leu Met Ser Thr Ser Ala Thr Ala Thr Glu Thr Ala Thr
                225                 230                 235 aag agg caa gaa acc tgg gat tgg ttt tca tgg ttg ttt cta cca tca     1190
Lys Arg Gln Glu Thr Trp Asp Trp Phe Ser Trp Leu Phe Leu Pro Ser
            240                 245                 250 gag tca aag aat cat ctt cac aca aca aca caa atg gct ggt acg tct     1238
Glu Ser Lys Asn His Leu His Thr Thr Thr Gln Met Ala Gly Thr Ser
        255                 260                 265 tca aat acc atc tca gca ggc tgg gag cca aat gaa gaa aat gaa gat     1286
Ser Asn Thr Ile Ser Ala Gly Trp Glu Pro Asn Glu Glu Asn Glu Asp
    270                 275                 280 gaa aga gac aga cac ctc agt ttt tct gga tca ggc att gat gat gat     1334
Glu Arg Asp Arg His Leu Ser Phe Ser Gly Ser Gly Ile Asp Asp Asp
285                 290                 295                 300 gaa gat ttt atc tcc agc acc att tca acc aca cca cgg gct ttt gac     1382
Glu Asp Phe Ile Ser Ser Thr Ile Ser Thr Thr Pro Arg Ala Phe Asp
                305                 310                 315 cac aca aaa cag aac cag gac tgg acc cag tgg aac cca agc cat tca     1430
His Thr Lys Gln Asn Gln Asp Trp Thr Gln Trp Asn Pro Ser His Ser
            320                 325                 330 aat ccg gaa gtg cta ctt cag aca acc aca agg atg act gat gta gac     1478
Asn Pro Glu Val Leu Leu Gln Thr Thr Thr Arg Met Thr Asp Val Asp
        335                 340                 345 aga aat ggc acc act gct tat gaa gga aac tgg aac cca gaa gca cac     1526
Arg Asn Gly Thr Thr Ala Tyr Glu Gly Asn Trp Asn Pro Glu Ala His
    350                 355                 360 cct ccc ctc att cac cat gag cat cat gag gaa gaa gag acc cca cat     1574
Pro Pro Leu Ile His His Glu His His Glu Glu Glu Glu Thr Pro His
365                 370                 375                 380 tct aca agc aca atc cag gca act cct agt agt aca acg gaa gaa aca     1622
Ser Thr Ser Thr Ile Gln Ala Thr Pro Ser Ser Thr Thr Glu Glu Thr
                385                 390                 395 gct acc cag aag gaa cag tgg ttt ggc aac aga tgg cat gag gga tat     1670
Ala Thr Gln Lys Glu Gln Trp Phe Gly Asn Arg Trp His Glu Gly Tyr
            400                 405                 410 cgc caa aca ccc aaa gaa gac tcc cat tcg aca aca ggg aca gct gca     1718
```

```
                Arg Gln Thr Pro Lys Glu Asp Ser His Ser Thr Thr Gly Thr Ala Ala
                            415                 420                 425 gcc tca gct cat acc agc cat cca atg caa gga agg aca aca cca agc           1766
Ala Ser Ala His Thr Ser His Pro Met Gln Gly Arg Thr Thr Pro Ser
430                 435                 440 cca gag gac agt tcc tgg act gat ttc ttc aac cca atc tca cac ccc           1814
Pro Glu Asp Ser Ser Trp Thr Asp Phe Phe Asn Pro Ile Ser His Pro
445                 450                 455                 460 atg gga cga ggt cat caa gca gga aga agg atg gat atg gac tcc agt           1862
Met Gly Arg Gly His Gln Ala Gly Arg Arg Met Asp Met Asp Ser Ser
                465                 470                 475 cat agt ata acg ctt cag cct act gca aat cca aac aca ggt ttg gtg           1910
His Ser Ile Thr Leu Gln Pro Thr Ala Asn Pro Asn Thr Gly Leu Val
                480                 485                 490 gaa gat ttg gac agg aca gga cct ctt tca atg aca acg cag cag agt           1958
Glu Asp Leu Asp Arg Thr Gly Pro Leu Ser Met Thr Thr Gln Gln Ser
            495                 500                 505 aat tct cag agc ttc tct aca tca cat gaa ggc ttg gaa gaa gat aaa           2006
Asn Ser Gln Ser Phe Ser Thr Ser His Glu Gly Leu Glu Glu Asp Lys
        510                 515                 520 gac cat cca aca act tct act ctg aca tca agc aat agg aat gat gtc           2054
Asp His Pro Thr Thr Ser Thr Leu Thr Ser Ser Asn Arg Asn Asp Val
525                 530                 535                 540 aca ggt gga aga aga gac cca aat cat tct gaa ggc tca act act tta           2102
Thr Gly Gly Arg Arg Asp Pro Asn His Ser Glu Gly Ser Thr Thr Leu
                545                 550                 555 ctg gaa ggt tat acc tct cat tac cca cac acg aag gaa agc agg acc           2150
Leu Glu Gly Tyr Thr Ser His Tyr Pro His Thr Lys Glu Ser Arg Thr
                560                 565                 570 ttc atc cca gtg acc tca gct aag act ggg tcc ttt gga gtt act gca           2198
Phe Ile Pro Val Thr Ser Ala Lys Thr Gly Ser Phe Gly Val Thr Ala
            575                 580                 585 gtt act gtt gga gat tcc aac tct aat gtc aat cgt tcc tta tca gga           2246
Val Thr Val Gly Asp Ser Asn Ser Asn Val Asn Arg Ser Leu Ser Gly
        590                 595                 600 gac caa gac aca ttc cac ccc agt ggg ggg tcc cat acc act cat gga           2294
Asp Gln Asp Thr Phe His Pro Ser Gly Gly Ser His Thr Thr His Gly
605                 610                 615                 620 tct gaa tca gat gga cac tca cat ggg agt caa gaa ggt gga gca aac           2342
Ser Glu Ser Asp Gly His Ser His Gly Ser Gln Glu Gly Gly Ala Asn
                625                 630                 635 aca acc tct ggt cct ata agg aca ccc caa att cca gaa tgg ctg atc           2390
Thr Thr Ser Gly Pro Ile Arg Thr Pro Gln Ile Pro Glu Trp Leu Ile
                640                 645                 650 atc ttg gca tcc ctc ttg gcc ttg gct ttg att ctt gca gtt tgc att           2438
Ile Leu Ala Ser Leu Leu Ala Leu Ala Leu Ile Leu Ala Val Cys Ile
            655                 660                 665 gca gtc aac agt cga aga agg tgt ggg cag aag aaa aag cta gtg atc           2486
Ala Val Asn Ser Arg Arg Arg Cys Gly Gln Lys Lys Lys Leu Val Ile
670                 675                 680 aac agt ggc aat gga gct gtg gag gac aga aag cca agt gga ctc aac           2534
Asn Ser Gly Asn Gly Ala Val Glu Asp Arg Lys Pro Ser Gly Leu Asn
685                 690                 695                 700 gga gag gcc agc aag tct cag gaa atg gtg cat ttg gtg aac aag gag           2582
Gly Glu Ala Ser Lys Ser Gln Glu Met Val His Leu Val Asn Lys Glu
                705                 710                 715 tcg tca gaa act cca gac cag ttt atg aca gct gat gag aca agg aac           2630
Ser Ser Glu Thr Pro Asp Gln Phe Met Thr Ala Asp Glu Thr Arg Asn
                720                 725                 730
```

```
ctg cag aat gtg gac atg aag att ggg gtg taa cacctacacc attatcttgg    2683
Leu Gln Asn Val Asp Met Lys Ile Gly Val
    735                 740 aaagaaacaa ccgttggaaa cataaccatt acagggagct gggacactta acagatgcaa    2743
tgtgctactg attgtttcat tgcgaatctt ttttagcata aaattttcta ctcttttgt     2803 tttttgtgtt ttgttcttta aagtcaggtc caatttgtaa aaacagcatt gctttctgaa    2863
attagggccc aattaataat cagcaagaat ttgatcgttc cagttcccac ttggaggcct    2923
ttcatccctc gggtgtgcta tggatggctt ctaacaaaaa ctacacatat gtattcctga    2983
tcgccaacct ttcccccacc agctaaggac atttcccagg gttaataggg cctggtccct    3043
gggaggaaat ttgaatgggt ccatttttgcc cttccatagc ctaatccctg ggcattgctt   3103
tccactgagg ttgggggttg gggtgtacta gttacacatc ttcaacagac ccctctaga    3163 aatttttcag atgcttctgg gagacaccca aagggtgaag ctatttatct gtagtaaact    3223
atttatctgt gttttttgaaa tattaaaccc tggatcagtc ctttgatcag tataattttt   3283
taaagttact ttgtcagagg cacaaaaggg tttaaactga ttcataataa atatctgtac    3343
ttcttcgatc ttcaccttt gtgctgtgat tcttcagttt ctaaaccagc actgtctggg     3403
tccctacaat gtatcaggaa gagctgagaa tggtaaggag actcttctaa gtcttcatct    3463
cagagaccct gagttcccac tcagacccac tcagccaaat ctcatggaag accaaggagg    3523
gcagcactgt ttttgttttt tgttttttgt tttttttttt tgacactgtc caaaggtttt    3583
ccatcctgtc ctggaatcag agttggaagc tgaggagctt cagcctcttt tatggtttaa    3643
tggccacctg ttctctcctg tgaaaggctt tgcaaagtca cattaagttt gcatgacctg    3703
ttatccctgg ggccctattt catagaggct ggccctatta gtgatttcca aaaacaatat    3763
ggaagtgcct tttgatgtct tacaataaga gaagaagcca atggaaatga aagagattgg    3823
caaaggggaa ggatgatgcc atgtagatcc tgtttgacat ttttatggct gtatttgtaa    3883
acttaaacac accagtgtct gttcttgatg cagttgctat ttaggatgag ttaagtgcct    3943
ggggagtccc tcaaaaggtt aaagggattc ccatcattgg aatcttatca ccagatagge    4003 aagtttatga ccaaacaaga gagtactggc tttatcctct aacctcatat tttctcccac    4063
ttggcaagtc ctttgtggca tttattcatc agtcagggtg tccgattggt cctagaactt    4123
ccaaaggctg cttgtcatag aagccattgc atctataaag caacggctcc tgttaaatgg    4183
tatctccttt ctgaggctcc tactaaaagt catttgttac ctaaacttat gtgcttaaca    4243
ggcaatgctt ctcagaccac aaagcagaaa gaagaagaaa agctcctgac taaatcaggg    4303
ctgggcttag acagagttga tctgtagaat atctttaaag gagagatgtc aactttctgc    4363
actattccca gcctctgctc ctccctgtct accctctccc ctccctctct ccctccactt    4423 cacccccacaa tcttgaaaaa cttcctttct cttctgtgaa catcattggc cagatccatt    4483
ttcagtggtc tggatttctt tttattttct tttcaacttg aaagaaactg acattaggc    4543 cactatgtgt tgttactgcc actagtgttc aagtgcctct tgttttccca gagatttcct    4603
gggtctgcca gaggcccaga caggctcact caagctcttt aactgaaaag caacaagcca    4663
ctccaggaca aggttcaaaa tggttacaac agcctctacc tgtcgcccca gggagaaagg    4723
ggtagtgata caagtctcat agccagagat ggttttccac tccttctaga tattcccaaa    4783
aagaggctga gacaggaggt tattttcaat tttattttgg aattaaatac tttttttccct   4843 ttattactgt tgtagtccct cacttggata tacctctgtt ttcacgatag aaataaggga    4903
ggtctagagc ttctattcct tggccattgt caacggagag ctggccaagt cttcacaaac    4963
```

| | | |
|---|---|---|
| ccttgcaaca ttgcctgaag tttatggaat aagatgtatt ctcactccct tgatctcaag | 5023 |
| ggcgtaactc tggaagcaca gcttgactac acgtcatttt taccaatgat tttcaggtga | 5083 |
| cctgggctaa gtcatttaaa ctgggtcttt ataaaagtaa aaggccaaca tttaattatt | 5143 |
| ttgcaaagca acctaagagc taaagatgta attttcttg caattgtaaa tcttttgtgt | 5203 |
| ctcctgaaga cttcccttaa aattagctct gagtgaaaaa tcaaaagaga caaaagacat | 5263 |
| cttcgaatcc atatttcaag cctggtagaa ttggcttttc tagcagaacc tttccaaaag | 5323 |
| ttttatattg agattcataa caacaccaag aattgatttt gtagccaaca ttcattcaat | 5383 |
| actgttatat cagaggagta ggagagagga aacatttgac ttatctggaa aagcaaaatg | 5443 |
| tacttaagaa taagaataac atggtccatt caccttatg ttatagatat gtctttgtgt | 5503 |
| aaatcatttg ttttgagttt tcaaagaata gcccattgtt cattcttgtg ctgtacaatg | 5563 |
| accactgtta ttgttacttt gacttttcag agcacaccct tcctctggtt tttgtatatt | 5623 |
| tattgatgga tcaataataa tgaggaaagc atgatatgta tattgctgag ttgaaagcac | 5683 |
| ttattggaaa atattaaaag gctaacatta aaagactaaa ggaaacagaa aaaaaaaaa | 5743 |
| aaaaa | 5748 |

```
<210> SEQ ID NO 14
<211> LENGTH: 742
<212> TYPE: PRT
<213> ORGANISM: Homo sapiens

<400> SEQUENCE: 14

Met Asp Lys Phe Trp Trp His Ala Ala Trp Gly Leu Cys Leu Val Pro
1               5                  10                  15

Leu Ser Leu Ala Gln Ile Asp Leu Asn Ile Thr Cys Arg Phe Ala Gly
            20                  25                  30

Val Phe His Val Glu Lys Asn Gly Arg Tyr Ser Ile Ser Arg Thr Glu
        35                  40                  45

Ala Ala Asp Leu Cys Lys Ala Phe Asn Ser Thr Leu Pro Thr Met Ala
    50                  55                  60

Gln Met Glu Lys Ala Leu Ser Ile Gly Phe Glu Thr Cys Arg Tyr Gly
65                  70                  75                  80

Phe Ile Glu Gly His Val Val Ile Pro Arg Ile His Pro Asn Ser Ile
                85                  90                  95

Cys Ala Ala Asn Asn Thr Gly Val Tyr Ile Leu Thr Ser Asn Thr Ser
            100                 105                 110

Gln Tyr Asp Thr Tyr Cys Phe Asn Ala Ser Ala Pro Pro Glu Glu Asp
        115                 120                 125

Cys Thr Ser Val Thr Asp Leu Pro Asn Ala Phe Asp Gly Pro Ile Thr
    130                 135                 140

Ile Thr Ile Val Asn Arg Asp Gly Thr Arg Tyr Val Gln Lys Gly Glu
145                 150                 155                 160

Tyr Arg Thr Asn Pro Glu Asp Ile Tyr Pro Ser Asn Pro Thr Asp Asp
                165                 170                 175

Asp Val Ser Ser Gly Ser Ser Glu Arg Ser Thr Ser Gly Gly
            180                 185                 190

Tyr Ile Phe Tyr Thr Phe Ser Thr Val His Pro Ile Pro Asp Glu Asp
        195                 200                 205

Ser Pro Trp Ile Thr Asp Ser Thr Asp Arg Ile Pro Ala Thr Thr Leu
    210                 215                 220
```

```
Met Ser Thr Ser Ala Thr Ala Thr Glu Thr Ala Lys Arg Gln Glu
225                 230                 235                 240

Thr Trp Asp Trp Phe Ser Trp Leu Phe Leu Pro Ser Glu Ser Lys Asn
                245                 250                 255

His Leu His Thr Thr Thr Gln Met Ala Gly Thr Ser Ser Asn Thr Ile
                260                 265                 270

Ser Ala Gly Trp Glu Pro Asn Glu Glu Asn Glu Asp Glu Arg Asp Arg
                275                 280                 285

His Leu Ser Phe Ser Gly Ser Gly Ile Asp Asp Glu Asp Phe Ile
    290                 295                 300

Ser Ser Thr Ile Ser Thr Thr Pro Arg Ala Phe Asp His Thr Lys Gln
305                 310                 315                 320

Asn Gln Asp Trp Thr Gln Trp Asn Pro Ser His Ser Asn Pro Glu Val
                325                 330                 335

Leu Leu Gln Thr Thr Thr Arg Met Thr Asp Val Asp Arg Asn Gly Thr
                340                 345                 350

Thr Ala Tyr Glu Gly Asn Trp Asn Pro Glu Ala His Pro Pro Leu Ile
                355                 360                 365

His His Glu His His Glu Glu Glu Thr Pro His Ser Thr Ser Thr
    370                 375                 380

Ile Gln Ala Thr Pro Ser Ser Thr Thr Glu Glu Thr Ala Thr Gln Lys
385                 390                 395                 400

Glu Gln Trp Phe Gly Asn Arg Trp His Glu Gly Tyr Arg Gln Thr Pro
                405                 410                 415

Lys Glu Asp Ser His Ser Thr Thr Gly Thr Ala Ala Ala Ser Ala His
                420                 425                 430

Thr Ser His Pro Met Gln Gly Arg Thr Thr Pro Ser Pro Glu Asp Ser
                435                 440                 445

Ser Trp Thr Asp Phe Phe Asn Pro Ile Ser His Pro Met Gly Arg Gly
                450                 455                 460

His Gln Ala Gly Arg Arg Met Asp Met Asp Ser Ser His Ser Ile Thr
465                 470                 475                 480

Leu Gln Pro Thr Ala Asn Pro Asn Thr Gly Leu Val Glu Asp Leu Asp
                485                 490                 495

Arg Thr Gly Pro Leu Ser Met Thr Thr Gln Gln Ser Asn Ser Gln Ser
                500                 505                 510

Phe Ser Thr Ser His Glu Gly Leu Glu Glu Asp Lys Asp His Pro Thr
                515                 520                 525

Thr Ser Thr Leu Thr Ser Ser Asn Arg Asn Asp Val Thr Gly Gly Arg
530                 535                 540

Arg Asp Pro Asn His Ser Glu Gly Ser Thr Thr Leu Leu Glu Gly Tyr
545                 550                 555                 560

Thr Ser His Tyr Pro His Thr Lys Glu Ser Arg Thr Phe Ile Pro Val
                565                 570                 575

Thr Ser Ala Lys Thr Gly Ser Phe Gly Val Thr Ala Val Thr Val Gly
                580                 585                 590

Asp Ser Asn Ser Asn Val Asn Arg Ser Leu Ser Gly Asp Gln Asp Thr
                595                 600                 605

Phe His Pro Ser Gly Gly Ser His Thr Thr His Gly Ser Glu Ser Asp
                610                 615                 620

Gly His Ser His Gly Ser Gln Glu Gly Gly Ala Asn Thr Thr Ser Gly
625                 630                 635                 640

Pro Ile Arg Thr Pro Gln Ile Pro Glu Trp Leu Ile Ile Leu Ala Ser
```

```
                    645                 650                 655
Leu Leu Ala Leu Ala Leu Ile Leu Ala Val Cys Ile Ala Val Asn Ser
            660                 665                 670

Arg Arg Arg Cys Gly Gln Lys Lys Leu Val Ile Asn Ser Gly Asn
        675                 680                 685

Gly Ala Val Glu Asp Arg Lys Pro Ser Gly Leu Asn Gly Glu Ala Ser
    690                 695                 700

Lys Ser Gln Glu Met Val His Leu Val Asn Lys Glu Ser Ser Glu Thr
705                 710                 715                 720

Pro Asp Gln Phe Met Thr Ala Asp Glu Thr Arg Asn Leu Gln Asn Val
                725                 730                 735

Asp Met Lys Ile Gly Val
            740

<210> SEQ ID NO 15
<211> LENGTH: 3936
<212> TYPE: DNA
<213> ORGANISM: Homo sapiens
<220> FEATURE:
<221> NAME/KEY: CDS
<222> LOCATION: (557)..(2131)

<400> SEQUENCE: 15
actcctcctc tctgcccctc agctcgctca tctttcttcc cgccccctct cttttccttc     60
tttggttctt tgaagtgatg agctagcgca accacaaacc atacattcct tttgtagaaa    120
aacccgtgcc tcgaatgagg cgagactcag agaggaccca ggcgcggggc ggacccctcc    180
aattccttcc tcgcgccccc gaaagagcgg cgcaccagca gccgaactgc ggcgcccag     240 gctcctggt ccggccggga tgcggccggt accgctcccc gccgggaac aacctctcca     300 ctcttcctgc agggagctgg tgccagccga cagccgcgcc agggccgctc cgggtaccag    360
ggtcggatcg ggtgacgtcg cgaacttgcg cctggccgcc aagccggcct ccaggctgaa    420
gaaggacccg ccccggcctt gacccgggcc ccgcccctcc agcggggca ccgagccccg     480 gccctagctg ctcgccccta ctcgccggca ctcgcccggc tcgcccgctt tcgcacccag    540
ttcacgcgcc acagct atg tgt ccc cga gcc gcg cgg gcg ccc gcg acg cta    592
              Met Cys Pro Arg Ala Ala Arg Ala Pro Ala Thr Leu
                1               5                   10 ctc ctc gcc ctg ggc gcg gtg ctg tgg cct gcg gct ggc gcc tgg gag      640
Leu Leu Ala Leu Gly Ala Val Leu Trp Pro Ala Ala Gly Ala Trp Glu
        15                  20                  25 ctt acg att ttg cac acc aac gac gtg cac agc cgg ctg gag cag acc      688
Leu Thr Ile Leu His Thr Asn Asp Val His Ser Arg Leu Glu Gln Thr
    30                  35                  40 agc gag gac tcc agc aag tgc gtc aac gcc agc cgc tgc atg ggt ggc      736
Ser Glu Asp Ser Ser Lys Cys Val Asn Ala Ser Arg Cys Met Gly Gly
45                  50                  55                  60 gtg gct cgg ctc ttc acc aag gtt cag cag atc cgc cgc gcc gaa ccc      784
Val Ala Arg Leu Phe Thr Lys Val Gln Gln Ile Arg Arg Ala Glu Pro
                65                  70                  75 aac gtg ctg ctg ctg gac gcc ggc gac cag tac cag ggc act atc tgg      832
Asn Val Leu Leu Leu Asp Ala Gly Asp Gln Tyr Gln Gly Thr Ile Trp
            80                  85                  90 ttc acc gtg tac aag ggc gcc gag gtg gcg cac ttc atg aac gcc ctg      880
Phe Thr Val Tyr Lys Gly Ala Glu Val Ala His Phe Met Asn Ala Leu
        95                  100                 105 cgc tac gat gcc atg gca ctg gga aat cat gaa ttt gat aat ggt gtg      928
Arg Tyr Asp Ala Met Ala Leu Gly Asn His Glu Phe Asp Asn Gly Val
```

```
                  110                 115                 120
gaa gga ctg atc gag cca ctc ctc aaa gag gcc aaa ttt cca att ctg        976
Glu Gly Leu Ile Glu Pro Leu Leu Lys Glu Ala Lys Phe Pro Ile Leu
125                 130                 135                 140 agt gca aac att aaa gca aag ggg cca cta gca tct caa ata tca gga       1024
Ser Ala Asn Ile Lys Ala Lys Gly Pro Leu Ala Ser Gln Ile Ser Gly
                145                 150                 155 ctt tat ttg cca tat aaa gtt ctt cct gtt ggt gat gaa gtt gtg gga       1072
Leu Tyr Leu Pro Tyr Lys Val Leu Pro Val Gly Asp Glu Val Val Gly
            160                 165                 170 atc gtt gga tac act tcc aaa gaa acc cct ttt ctc tca aat cca ggg       1120
Ile Val Gly Tyr Thr Ser Lys Glu Thr Pro Phe Leu Ser Asn Pro Gly
        175                 180                 185 aca aat tta gtg ttt gaa gat gaa atc act gca tta caa cct gaa gta       1168
Thr Asn Leu Val Phe Glu Asp Glu Ile Thr Ala Leu Gln Pro Glu Val
    190                 195                 200 gat aag tta aaa act cta aat gtg aac aaa att att gca ctg gga cat       1216
Asp Lys Leu Lys Thr Leu Asn Val Asn Lys Ile Ile Ala Leu Gly His
205                 210                 215                 220 tcg ggt ttt gaa atg gat aaa ctc atc gct cag aaa gtg agg ggt gtg       1264
Ser Gly Phe Glu Met Asp Lys Leu Ile Ala Gln Lys Val Arg Gly Val
                225                 230                 235 gac gtc gtg gtg gga gga cac tcc aac aca ttt ctt tac aca ggc aat       1312
Asp Val Val Val Gly Gly His Ser Asn Thr Phe Leu Tyr Thr Gly Asn
            240                 245                 250 cca cct tcc aaa gag gtg cct gct ggg aag tac cca ttc ata gtc act       1360
Pro Pro Ser Lys Glu Val Pro Ala Gly Lys Tyr Pro Phe Ile Val Thr
        255                 260                 265 tct gat gat ggg cgg aag gtt cct gta gtc cag gcc tat gct ttt ggc       1408
Ser Asp Asp Gly Arg Lys Val Pro Val Val Gln Ala Tyr Ala Phe Gly
    270                 275                 280 aaa tac cta ggc tat ctg aag atc gag ttt gat gaa aga gga aac gtc       1456
Lys Tyr Leu Gly Tyr Leu Lys Ile Glu Phe Asp Glu Arg Gly Asn Val
285                 290                 295                 300 atc tct tcc cat gga aat ccc att ctt cta aac agc agc att cct gaa       1504
Ile Ser Ser His Gly Asn Pro Ile Leu Leu Asn Ser Ser Ile Pro Glu
                305                 310                 315 gat cca agc ata aaa gca gac att aac aaa tgg agg ata aaa ttg gat       1552
Asp Pro Ser Ile Lys Ala Asp Ile Asn Lys Trp Arg Ile Lys Leu Asp
            320                 325                 330 aat tat tct acc cag gaa tta ggg aaa aca att gtc tat ctg gat ggc       1600
Asn Tyr Ser Thr Gln Glu Leu Gly Lys Thr Ile Val Tyr Leu Asp Gly
        335                 340                 345 tcc tct caa tca tgc cgc ttt aga gaa tgc aac atg ggc aac ctg att       1648
Ser Ser Gln Ser Cys Arg Phe Arg Glu Cys Asn Met Gly Asn Leu Ile
    350                 355                 360 tgt gat gca atg att aac aac aac ctg aga cac acg gat gaa atg ttc       1696
Cys Asp Ala Met Ile Asn Asn Asn Leu Arg His Thr Asp Glu Met Phe
365                 370                 375                 380 tgg aac cac gta tcc atg tgc att tta aat gga ggt ggt atc cgg tcg       1744
Trp Asn His Val Ser Met Cys Ile Leu Asn Gly Gly Gly Ile Arg Ser
                385                 390                 395 ccc att gat gaa cgc aac aat gga atc cat gtg gtg tat gat ctt tcc       1792
Pro Ile Asp Glu Arg Asn Asn Gly Ile His Val Val Tyr Asp Leu Ser
            400                 405                 410 cga aaa cct gga gac aga gta gtc aaa tta gat gtt ctt tgc acc aag       1840
Arg Lys Pro Gly Asp Arg Val Val Lys Leu Asp Val Leu Cys Thr Lys
        415                 420                 425 tgt cga gtg ccc agt tat gac cct ctc aaa atg gac gag gta tat aag       1888
```

```
                                                                          -continued Cys Arg Val Pro Ser Tyr Asp Pro Leu Lys Met Asp Glu Val Tyr Lys
    430             435             440 gtg atc ctc cca aac ttc ctg gcc aat ggt gga gat ggg ttc cag atg   1936
Val Ile Leu Pro Asn Phe Leu Ala Asn Gly Gly Asp Gly Phe Gln Met
445             450             455             460 ata aaa gat gaa tta tta aga cat gac tct ggt gac caa gat atc aac   1984
Ile Lys Asp Glu Leu Leu Arg His Asp Ser Gly Asp Gln Asp Ile Asn
            465             470             475 gtg gtt tct aca tat atc tcc aaa atg aaa gta att tat cca gca gtt   2032
Val Val Ser Thr Tyr Ile Ser Lys Met Lys Val Ile Tyr Pro Ala Val
            480             485             490 gaa ggt cgg atc aag ttt tcc aca gga agt cac tgc cat gga agc ttt   2080
Glu Gly Arg Ile Lys Phe Ser Thr Gly Ser His Cys His Gly Ser Phe
        495             500             505 tct tta ata ttt ctt tca ctt tgg gca gtg atc ttt gtt tta tac caa   2128
Ser Leu Ile Phe Leu Ser Leu Trp Ala Val Ile Phe Val Leu Tyr Gln
        510             515             520 tag ccaaaaattc tccttgcctt taatgtgtga aactgcattt tttcaagtga         2181
gattcaaatc tgccttttag gacctggctt tgtgacagca aaaccatct ttacaggctc   2241 ctagaagctg aaggttagag cattataaaa tgaagagaca gacatgatta ctcagggtca  2301
gcaacctagt gagttagaaa aaaaattaac atagggccct ataaggagaa agccaactat  2361
gttaagttta cgtgtccaaa ttttaatgaa attttactaa caattttaaa ccatatttt   2421 cttcttcata tccatttcta atccatcaaa cagcttatgt ttacataaaa ttttatcatt  2481
cacaaggaag ttttaagcac actgtctcat ttgatatcca caacttattt ttggtaggaa  2541
agagagatgt ttttcccacc tgtcagatga aaaaactgaa gctcaaaaag ggttgacttg  2601
accatacagc taatgctgac agatccaaga cctagaccta ggtcttttga actcaagtcc  2661
agcattctca actatatcaa gttactgttc agaatactta atatctcctc tcttcataat  2721
tatcaatagc cccaagctca tggatgacaa atctctgctt tatttcttgt ctctattttt  2781
tcactttata gctcctgtta aatagcaag tttaatggta taaacacagg ataccatcct   2841
ctcttgcaac acccatgtgc ctttgatgag tcaggtagca agctgtagta gataatgaga  2901
aaggccagag gctgcaaaag acagtcaaag gacacgagag aaaggaaggg gaagaacagg  2961
actccaggac tgttttatat tatagaaaag caagagctaa agagcattta cacatgttaa  3021
acagatactt gttaagcata gtgcctgaca cacggcatta gctgttattt tatgagattc  3081
catcagctct gcctctgtcc tctttcttct aacatgaagg tatcatgaga agagaacctt  3141
ctaacataag ctgtaattct aaacctgcac ttgtccctct ccagcaagag gctagcactg  3201
aattcattct actcatacta cacacccagt tatggaatgt ccagagttct cgaagaaaat  3261
aaatgacttt aggaagaggt atacattttt taagtcgctc tgcctccaaa tctgaacagt  3321
cactgtaaat cattcttaag cccagatatg agaacttctg ctggaaagtg ggaccctctg  3381
agtgggtggt cagaaaatac ccatgctgat gaaatgacct atgcccaaag aacaaatact  3441
taacgtggga gtggaaccac atgagcctgc tcagctctgc ataagtaatt caagaaatgg  3501
gaggcttcac cttaaaaaca gtgtgcaaat ggcagctaga ggttttgata ggaagtatgt  3561
ttgtttctta gtgtttacaa atattaagta ctcttgatac aaaatatact tttaaacttc  3621
ataacctttt tataaaagtt gttgcagcaa aataatagcc tcggttctat gcatatatgg  3681
attagctata aaaatgtca ataagattgt acaggaaaa ttagagaaag tcacatttag    3741
ggtttatttt ttacacttgg ccagtaaaat agggtaaatc ctattagaat tttttaaaga  3801
```

```
acttttttta agtttcctaa atctgtgtgt gtattgtgaa gtggtataag aaatgacttt    3861
gaaccacttt gcaattgtag attcccaaca ataaaattga agataagctc tttggtcaaa    3921
aaaaaaaaaa aaaaa                                                     3936
```

<210> SEQ ID NO 16
<211> LENGTH: 524
<212> TYPE: PRT
<213> ORGANISM: Homo sapiens

<400> SEQUENCE: 16

```
Met Cys Pro Arg Ala Ala Arg Ala Pro Ala Thr Leu Leu Ala Leu
1               5                   10                  15

Gly Ala Val Leu Trp Pro Ala Ala Gly Ala Trp Glu Leu Thr Ile Leu
            20                  25                  30

His Thr Asn Asp Val His Ser Arg Leu Glu Gln Thr Ser Glu Asp Ser
        35                  40                  45

Ser Lys Cys Val Asn Ala Ser Arg Cys Met Gly Gly Val Ala Arg Leu
    50                  55                  60

Phe Thr Lys Val Gln Gln Ile Arg Arg Ala Glu Pro Asn Val Leu Leu
65                  70                  75                  80

Leu Asp Ala Gly Asp Gln Tyr Gln Gly Thr Ile Trp Phe Thr Val Tyr
                85                  90                  95

Lys Gly Ala Glu Val Ala His Phe Met Asn Ala Leu Arg Tyr Asp Ala
            100                 105                 110

Met Ala Leu Gly Asn His Glu Phe Asp Asn Gly Val Glu Gly Leu Ile
        115                 120                 125

Glu Pro Leu Leu Lys Glu Ala Lys Phe Pro Ile Leu Ser Ala Asn Ile
    130                 135                 140

Lys Ala Lys Gly Pro Leu Ala Ser Gln Ile Ser Gly Leu Tyr Leu Pro
145                 150                 155                 160

Tyr Lys Val Leu Pro Val Gly Asp Glu Val Val Gly Ile Val Gly Tyr
                165                 170                 175

Thr Ser Lys Glu Thr Pro Phe Leu Ser Asn Pro Gly Thr Asn Leu Val
            180                 185                 190

Phe Glu Asp Glu Ile Thr Ala Leu Gln Pro Glu Val Asp Lys Leu Lys
        195                 200                 205

Thr Leu Asn Val Asn Lys Ile Ile Ala Leu Gly His Ser Gly Phe Glu
    210                 215                 220

Met Asp Lys Leu Ile Ala Gln Lys Val Arg Gly Val Asp Val Val Val
225                 230                 235                 240

Gly Gly His Ser Asn Thr Phe Leu Tyr Thr Gly Asn Pro Pro Ser Lys
                245                 250                 255

Glu Val Pro Ala Gly Lys Tyr Pro Phe Ile Val Thr Ser Asp Asp Gly
            260                 265                 270

Arg Lys Val Pro Val Val Gln Ala Tyr Ala Phe Gly Lys Tyr Leu Gly
        275                 280                 285

Tyr Leu Lys Ile Glu Phe Asp Glu Arg Gly Asn Val Ile Ser Ser His
    290                 295                 300

Gly Asn Pro Ile Leu Leu Asn Ser Ser Ile Pro Glu Asp Pro Ser Ile
305                 310                 315                 320

Lys Ala Asp Ile Asn Lys Trp Arg Ile Lys Leu Asp Asn Tyr Ser Thr
                325                 330                 335

Gln Glu Leu Gly Lys Thr Ile Val Tyr Leu Asp Gly Ser Ser Gln Ser
            340                 345                 350
```

```
Cys Arg Phe Arg Glu Cys Asn Met Gly Asn Leu Ile Cys Asp Ala Met
            355                 360                 365

Ile Asn Asn Asn Leu Arg His Thr Asp Glu Met Phe Trp Asn His Val
    370                 375                 380

Ser Met Cys Ile Leu Asn Gly Gly Ile Arg Ser Pro Ile Asp Glu
385                 390                 395                 400

Arg Asn Asn Gly Ile His Val Val Tyr Asp Leu Ser Arg Lys Pro Gly
                405                 410                 415

Asp Arg Val Val Lys Leu Asp Val Leu Cys Thr Lys Cys Arg Val Pro
                420                 425                 430

Ser Tyr Asp Pro Leu Lys Met Asp Glu Val Tyr Lys Val Ile Leu Pro
            435                 440                 445

Asn Phe Leu Ala Asn Gly Gly Asp Gly Phe Gln Met Ile Lys Asp Glu
            450                 455                 460

Leu Leu Arg His Asp Ser Gly Asp Gln Asp Ile Asn Val Val Ser Thr
465                 470                 475                 480

Tyr Ile Ser Lys Met Lys Val Ile Tyr Pro Ala Val Glu Gly Arg Ile
                485                 490                 495

Lys Phe Ser Thr Gly Ser His Cys His Gly Ser Phe Ser Leu Ile Phe
            500                 505                 510

Leu Ser Leu Trp Ala Val Ile Phe Val Leu Tyr Gln
            515                 520

<210> SEQ ID NO 17
<211> LENGTH: 23
<212> TYPE: DNA
<213> ORGANISM: Artificial sequence
<220> FEATURE:
<223> OTHER INFORMATION: CD166-F primer

<400> SEQUENCE: 17
ccccagagga atttttgttt tac                                            23

<210> SEQ ID NO 18
<211> LENGTH: 23
<212> TYPE: DNA
<213> ORGANISM: Artificial sequence
<220> FEATURE:
<223> OTHER INFORMATION: CD166-R primer

<400> SEQUENCE: 18
agcctgatgt tatctttcat cca                                            23

<210> SEQ ID NO 19
<211> LENGTH: 22
<212> TYPE: DNA
<213> ORGANISM: Artificial sequence
<220> FEATURE:
<223> OTHER INFORMATION: CD73-F primer

<400> SEQUENCE: 19
gttcctgtag tccaggccta tg                                             22

<210> SEQ ID NO 20
<211> LENGTH: 22
<212> TYPE: DNA
<213> ORGANISM: Artificial sequence
<220> FEATURE:
<223> OTHER INFORMATION: CD73-R primer

<400> SEQUENCE: 20
```

```
acatttcatc cgtgtgtctc ag                                            22

<210> SEQ ID NO 21
<211> LENGTH: 20
<212> TYPE: DNA
<213> ORGANISM: Artificial sequence
<220> FEATURE:
<223> OTHER INFORMATION: GAPDH-F primer

<400> SEQUENCE: 21
gagtcaacgg atttggtcgt                                               20

<210> SEQ ID NO 22
<211> LENGTH: 20
<212> TYPE: DNA
<213> ORGANISM: Artificial sequence
<220> FEATURE:
<223> OTHER INFORMATION: GAPDH-R primer

<400> SEQUENCE: 22
ttgattttgg agggatctcg                                               20
```